United States Patent
Adams et al.

(10) Patent No.: US 8,044,075 B2
(45) Date of Patent: Oct. 25, 2011

(54) IL-8 RECEPTOR ANTAGONISTS

(75) Inventors: Gregory L. Adams, Collegeville, PA (US); James A. Brackley, III, Collegeville, PA (US); Jakob Busch-Petersen, King of Prussia, PA (US); Jianghe Deng, Collegeville, PA (US); Wei Fu, King of Prussia, PA (US); Huijie Li, King of Prussia, PA (US); Jack J. Taggart, King of Prussia, PA (US); Feng Wang, Collegeville, PA (US); Yonghui Wang, Collegeville, PA (US); Katherine Louisa Widdowson, Collegeville, PA (US); Hongyi Yu, Collegeville, PA (US)

(73) Assignee: GlaxoSmithKline, Philadelphia, PA (US)

( * ) Notice: Subject to any disclaimer, the term of this patent is extended or adjusted under 35 U.S.C. 154(b) by 260 days.

(21) Appl. No.: 12/517,878

(22) PCT Filed: Dec. 5, 2007

(86) PCT No.: PCT/US2007/086473
§ 371 (c)(1),
(2), (4) Date: Jun. 5, 2009

(87) PCT Pub. No.: WO2008/070707
PCT Pub. Date: Jun. 12, 2008

(65) Prior Publication Data
US 2010/0298387 A1 Nov. 25, 2010

Related U.S. Application Data

(60) Provisional application No. 60/868,599, filed on Dec. 5, 2006.

(51) Int. Cl.
*A01N 43/82* (2006.01)
*A61K 31/41* (2006.01)
(52) U.S. Cl. ........................................................ 514/363
(58) Field of Classification Search .................. 514/363
See application file for complete search history.

(56) References Cited

U.S. PATENT DOCUMENTS
2005/0143384 A1   6/2005   Sartori et al.

FOREIGN PATENT DOCUMENTS
WO   2006/088837   8/2006

OTHER PUBLICATIONS
Kolavi, et al., *Synthetic Communications*, vol. 36 pp. 1837-1843 (2006).

*Primary Examiner* — Yong Chong
(74) *Attorney, Agent, or Firm* — Robert H. Brink

(57) ABSTRACT

This invention relates to novel compounds, compositions and combinations thereof, useful in the treatment of disease states mediated by the chemokine, Interleukin-8 (IL-8).

16 Claims, No Drawings

IL-8 RECEPTOR ANTAGONISTS

This application is a §371 application of PCT/US2007/086473 filed 5 Dec. 2007, which claims the benefit of U.S. Provisional Application No. 60/868,599, filed 5 Dec. 2006.

FIELD OF THE INVENTION

This invention relates to IL-8 receptor antagonists, pharmaceutical compositions, processes for their preparation, and use thereof in treating IL-8, GROα, GROβ, GROγ, NAP-2, and ENA-78 mediated diseases.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell to lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP.

GROα, GROβ, GROγ and NAP-2 also belong to the chemokine family. Like IL-8 these chemokines have also been referred to by different names. For instance GROα, β, γ have been referred to as MGSAα, β and γ respectively (Melanoma Growth Stimulating Activity). All of the chemokines of the α-family which possess the ELR motif directly preceding the CXC motif bind to the IL-8 B receptor (CXCR2).

IL-8, GROα, GROβ, GROγ, NAP-2, and ENA-78 stimulate a number of functions in vitro. They have all been shown to have chemoattractant properties for neutrophils, while IL-8 and GROα have demonstrated T-lymphocytes, and basophilic chemotactic activity. In addition IL-8 can induce histamine release from basophils from both normal and atopic individuals. GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, GROα, GROβ, GROγ and NAP-2 promote the accumulation and activation of neutrophils, these chemokines have been implicated in a wide range of acute and chronic inflammatory disorders including psoriasis and rheumatoid arthritis. In addition, the ELR chemokines (those containing the amino acids ELR motif just prior to the CXC motif) have also been implicated in angiostasis.

In vitro, IL-8, GROα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the IL-8β receptor (CXCR2). The development of non-peptide small molecule antagonists for members of this receptor family has precedent. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GROα, GROβ, GROγ and NAP-2.

There remains a need for treatment, in this field, for compounds, which are capable of binding to the IL-8 α or β receptor. Therefore, conditions associated with an increase in IL-8 production (which is responsible for chemotaxis of neutrophil and T-cells subsets into the inflammatory site) would benefit by compounds, which are inhibitors of IL-8 receptor binding.

SUMMARY OF THE INVENTION

This invention provides for a method of treating a chemokine mediated disease, wherein the chemokine is one which binds to an IL-8 a or b receptor and which method comprises administering an effective amount of a compound of Formula (I), or a pharmaceutically acceptable salt thereof, as defined hereinbelow. In particular the chemokine is IL-8.

This invention also relates to a method of inhibiting the binding of IL-8 to its receptors in a mammal in need thereof which comprises administering to said mammal an effective amount of a compound of Formula (I).

The present invention also provides for the novel compounds of Formula (I), and pharmaceutical compositions comprising a compound of Formula (I), and a pharmaceutical carrier or diluent.

DETAILED DESCRIPTION OF THE INVENTION

Compounds useful in the present invention are represented by Formula (I):

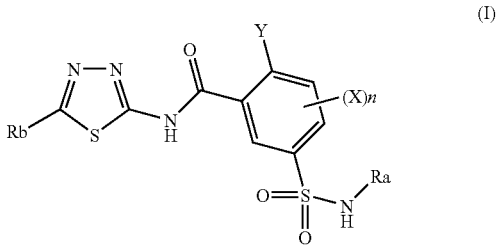

wherein:
Y is halogen;
n is 0, 1 or 2;
X is halogen;
Ra is selected from the group consisting of hydrogen, $C_{1-4}$alkyl, $C_{3-6}$cycloalkyl, $C_{3-6}$cycloalkyl$C_{1-4}$alkyl, and phenyl, wherein all moieties, except hydrogen, are optionally substituted, one to three times, by halogen, $CF_3$, OH or $C_{1-4}$alkyl; and
Rb is selected from the group consisting of phenyl, $C_{1-4}$alkyl, phenyl$C_{1-4}$alkyl, $C_{3-6}$cycloalkyl, phenyl$C_{3-6}$cycloalkyl and heteroaryl, wherein all moieties are optionally substituted, one to four times, by halogen, $CF_3$ or $C_{1-4}$alkyl;
or a pharmaceutically acceptable salt thereof.

As used herein, "alkyl" refers to a linear or branched saturated hydrocarbon group containing from 1 to 4 carbon atoms. Examples of such groups include methyl, ethyl, n-propyl, isopropyl, n-butyl, isobutyl, sec-butyl, tert butyl, and the like.

As used herein "cycloalkyl" refers to a saturated monocyclic hydrocarbon ring of 3 to 6 carbon atoms. Examples of such groups include cyclopropyl, cyclobutyl, cyclopentyl, cyclohexyl, and the like.

As used herein, "phenylalkyl" refers to a phenyl-$C_{1-4}$alkyl group wherein $C_{1-4}$alkyl is as defined above.

As used herein "heteroaryl" refers to a 5-6 membered monocyclic aromatic ring containing one heteroatom selected from oxygen and sulphur. Examples of such monocyclic aromatic rings include furanyl, thienyl and the like.

As used herein "phenylcycloalkyl" refers to a cycloalkyl linker substituted by an optionally substituted phenyl.

As used herein, "halogen" refers to F, Cl, Br or I.

As used herein, "optionally substituted," unless specifically defined, means substituted, independently, at each occurrence, one to three times, by such groups as halogen, $C_{1-4}$alkyl, and $CF_3$.

The compounds of the present invention may contain one or more asymmetric carbon atoms and may exist as racemates, racemic mixtures, individual enantiomers and diastereomers. Also, crystalline forms of the Formula (I) compounds may exist as polymorphs. All of these forms are contemplated to be within the scope of the present invention.

Additionally, those skilled in the art will appreciate that many organic compounds form complexes with solvents in which they are reacted or from which they are precipitated or crystallized. These complexes are known as "solvates." For example, a complex with water is known as a "hydrate." Solvates of Formula (I) compounds are within the scope of the invention.

Suitably, Y is halogen.
In one embodiment, Y is F, Cl, Br or I.
In another embodiment, Y is Cl.
In another embodiment, Y is Br.
In another embodiment, Y is F.
In one embodiment, X is halogen.
In another embodiment, X is F, Cl, Br or I.
In another embodiment, X is Cl.
In another embodiment, X is Br.
In another embodiment, X is F.
Suitably, n is 0, 1 or 2.
In one embodiment, n is 0.
In another embodiment, n is 1.
In another embodiment, n is 1, and there is an X substituent at the 3-, 4- or 6-position on the phenyl ring.
In another embodiment, n is 1 and there is an X substituent at the 3- or 4-position on the phenyl ring.
In another embodiment, n is 2.
In another embodiment, n is 2, and there is an X substituent at the 3- and 4-position on the phenyl ring.
In another embodiment, n is 2 and there is an X substituent at the 3- and 6-position on the phenyl ring.

Suitably, Ra is selected from the group consisting of hydrogen, $C_{1-4}$alkyl, $C_{3-6}$cycloalkyl, $C_{3-6}$cycloalkyl$C_{1-4}$alkyl, and phenyl, wherein all moieties, except hydrogen, are optionally substituted, one to three times, by halogen, $CF_3$ or $C_{1-4}$alkyl.

In one embodiment, Ra is hydrogen.
In another embodiment, Ra is $C_{1-4}$alkyl.
In another embodiment, Ra is selected from the group consisting of methyl, ethyl, propyl, and butyl.
In another embodiment, Ra is methyl, ethyl or propyl.
In another embodiment, Ra is ethyl.
In another embodiment, Ra is methylpropyl.
In another embodiment, Ra is methylethyl.
In another embodiment, Ra is $C_{1-4}$alkyl, substituted by $CF_3$ or F.
In another embodiment, Ra is trifluoroethyl.
In another embodiment, Ra is 2,2,2-trifluoroethyl.
In another embodiment, Ra is fluoroethyl.
In another embodiment, Ra is 2-fluoroethyl.
In another embodiment, Ra is trifluoropropyl.
In another embodiment, Ra is 3,3,3-trifluoropropyl.
In another embodiment, Ra is $C_{3-6}$cycloalkyl.
In another embodiment, Ra is cyclopropyl or cyclobutyl.
In another embodiment, Ra is cyclopropyl.
In another embodiment, Ra is $C_{3-6}$cycloalkyl$C_{1-4}$alkyl.
In another embodiment, Ra is cyclopropylmethyl.
In another embodiment, Ra is phenyl.

Suitably, Rb is selected from the group consisting of phenyl, $C_{1-4}$alkyl, phenyl$C_{1-4}$alkyl, $C_{3-6}$cycloalkyl, phenyl$C_{3-6}$cycloalkyl and heteroaryl, wherein all moieties are optionally substituted, independently, one to four times, by halogen, $CF_3$ or $C_{1-4}$alkyl.

In one embodiment, Rb is phenyl, substituted one to four times, independently, by halogen.
In one embodiment, Rb is phenyl, substituted once by F.
In one embodiment, Rb is 4-fluorophenyl.
In one embodiment, Rb is phenyl, substituted four times by F.
In another embodiment, Rb is 2,3,4,5-tetrafluorophenyl.
In one embodiment, Rb is phenyl, substituted twice, independently, by F or Cl.
In another embodiment, Rb is chlorofluorophenyl.
In another embodiment, Rb is 2-chloro-4-fluorophenyl or 4-chloro-2-fluorophenyl.
In another embodiment, Rb is chlorotrifluoromethylphenyl.
In another embodiment, Rb is 2-fluoro-4-trifluoromethylphenyl.
In another embodiment, Rb is $C_{1-4}$alkyl.
In another embodiment, Rb is 1,1-dimethylethyl.
In another embodiment, Rb is phenyl$C_{1-4}$alkyl, wherein the phenyl ring is optionally substituted once by halogen.
In another embodiment, Rb is phenyl$C_{1-4}$alkyl, wherein the phenyl ring is substituted at the 2-position or at the 4-position.
In another embodiment, Rb is fluorophenyl$C_{1-4}$alkyl.
In another embodiment, Rb is 2-fluorophenyl$C_{1-4}$alkyl.
In another embodiment, Rb is 4-fluorophenyl$C_{1-4}$alkyl.
In another embodiment, Rb is 1-(4-fluorophenyl)-1-methylethyl.
In another embodiment, Rb is bromophenyl$C_{1-4}$alkyl.
In another embodiment, Rb is 4-bromophenyl$C_{1-4}$alkyl.
In another embodiment, Rb is 1-(4-bromophenyl)-1-methylethyl.
In one embodiment, Rb is phenyl$C_{1-4}$alkyl.
In another embodiment, Rb is 1-methyl-1-phenylethyl.
In another embodiment, Rb is 1,1-dimethyl-2-phenylethyl.
In another embodiment, Rb is 1-phenylethyl.
In another embodiment, Rb is $C_{3-6}$cycloalkyl, optionally substituted once or twice, independently, by halogen, methyl or $CF_3$.
In another embodiment, Rb is cyclobutyl, cyclopentyl or cyclohexyl.
In another embodiment, Rb is cyclopentyl.
In another embodiment, Rb is methylcyclopentyl.
In another embodiment, Rb is 1-methylcyclopentyl.
In another embodiment, Rb is methylcyclohexyl.
In another embodiment, Rb is 1-methylcyclohexyl.
In another embodiment, Rb is 4,4-difluorocyclohexyl.
In another embodiment, Rb is trifluoromethylcyclopentyl.
In another embodiment, Rb is 1-trifluoromethylcyclopentyl.
In another embodiment, Rb is phenyl$C_{3-6}$cycloalkyl, wherein the phenyl ring is optionally substituted once or twice, independently, by methyl, halogen or $CF_3$.
In another embodiment, Rb is methylphenyl$C_{3-6}$cycloalkyl.
In another embodiment, Rb is methylphenylcyclobutyl.
In another embodiment, Rb is 3-methylphenylcyclobutyl.
In another embodiment, Rb is fluorophenylcyclobutyl.

In another embodiment, Rb is 2-,3-or 4-fluorophenylcyclobutyl.

In another embodiment, Rb is 4-fluorophenylcyclobutyl.
In another embodiment, Rb is chlorophenylcyclobutyl.
In another embodiment, Rb is 4-chlorophenylcyclobutyl.
In another embodiment, Rb is difluorophenylcyclobutyl.
In another embodiment, Rb is 2,4-difluorophenylcyclobutyl.
In another embodiment, Rb is phenylcyclobutyl.
In another embodiment, Rb is phenylcyclopropyl.
In another embodiment, Rb is phenylcyclopentyl.
In another embodiment, Rb is fluorophenylcyclopentyl.
In another embodiment, Rb is 4-fluorophenylcyclopentyl.
In another embodiment, Rb is trifluoromethylphenylcyclobutyl.
In another embodiment, Rb is 3-trifluoromethylphenylcyclobutyl.
In another embodiment, Rb is heteroaryl, optionally substituted once or twice by methyl.
In another embodiment, Rb is methylfuranyl.
In another embodiment, Rb is 2-methyl-3-furanyl.
In another embodiment, Rb is methylthienyl.
In another embodiment, Rb is 3-methyl-2-thienyl.
In another embodiment, Rb is dimethylfuranyl.
In another embodiment, Rb is 2,5-dimethyl-3-furanyl.

Illustrative compounds of the present invention include but are not limited to:

5-[(ethylamino)sulfonyl]-2-fluoro-N-[5-(1-methyl-1-phenylethyl)-1,3,4-thiadiazol-2-yl]benzamide;
5-(aminosulfonyl)-2-chloro-N-(5-cyclohexyl-1,3,4-thiadiazol-2-yl)benzamide;
2-fluoro-N-{5-[1-(4-fluorophenyl)-1-methylethyl]-1,3,4-thiadiazol-2-yl}-5-{[(2,2,2-trifluoroethyl)amino]sulfonyl}benzamide;
5-(aminosulfonyl)-2-chloro-N-[5-(4-fluorophenyl)-1,3,4-thiadiazol-2-yl]benzamide;
5-(aminosulfonyl)-2,3-dichloro-N-[5-(4-fluorophenyl)-1,3,4-thiadiazol-2-yl]benzamide;
5-[(ethylamino)sulfonyl]-2,3-difluoro-N-[5-(4-fluorophenyl)-1,3,4-thiadiazol-2-yl]benzamide;
5-[(ethylamino)sulfonyl]-2-fluoro-N-[5-(4-fluorophenyl)-1,3,4-thiadiazol-2-yl]benzamide;
5-(aminosulfonyl)-N-(5-cyclopentyl-1,3,4-thiadiazol-2-yl)-2-fluorobenzamide;
N-[5-(1,1-dimethylethyl)-1,3,4-thiadiazol-2-yl]-5-[(ethylamino)sulfonyl]-2-iodobenzamide;
3-chloro-5-[(ethylamino)sulfonyl]-2,4-difluoro-N-[5-(1-methyl-1-phenylethyl)-1,3,4-thiadiazol-2-yl]benzamide;
3-chloro-N-[5-(1,1-dimethylethyl)-1,3,4-thiadiazol-2-yl]-5-[(ethylamino)sulfonyl]-2,4-difluorobenzamide;
3-chloro-5-[(ethylamino)sulfonyl]-2,4-difluoro-N-[5-(4-fluorophenyl)-1,3,4-thiadiazol-2-yl]benzamide;
5-[(ethylamino)sulfonyl]-2,3,4-trifluoro-N-[5-(1-methyl-1-phenylethyl)-1,3,4-thiadiazol-2-yl]benzamide;
3-chloro-5-[(ethylamino)sulfonyl]-2-fluoro-N-[5-(1-methyl-1-phenylethyl)-1,3,4-thiadiazol-2-yl]benzamide;
3-chloro-N-[5-(1,1-dimethylethyl)-1,3,4-thiadiazol-2-yl]-5-[(ethylamino)sulfonyl]-2-fluorobenzamide;
N-(5-cyclopentyl-1,3,4-thiadiazol-2-yl)-5-[(ethylamino)sulfonyl]-2,4-difluorobenzamide;
3-[(ethylamino)sulfonyl]-2,6-difluoro-N-[5-(4-fluorophenyl)-1,3,4-thiadiazol-2-yl]benzamide;
2-fluoro-N-[5-(4-fluorophenyl)-1,3,4-thiadiazol-2-yl]-5-{[(2-methylpropyl)amino]sulfonyl}benzamide;
5-[(butylamino)sulfonyl]-2-fluoro-N-[5-(4-fluorophenyl)-1,3,4-thiadiazol-2-yl]benzamide;
2-fluoro-N-[5-(4-fluorophenyl)-1,3,4-thiadiazol-2-yl]-5-[(propylamino)sulfonyl]benzamide;
2-chloro-5-[(ethylamino)sulfonyl]-3-fluoro-N-[5-(4-fluorophenyl)-1,3,4-thiadiazol-2-yl]benzamide;
2,3-difluoro-N-[5-(4-fluorophenyl)-1,3,4-thiadiazol-2-yl]-5-[(propylamino)sulfonyl]benzamide;
3-chloro-5-[(ethylamino)sulfonyl]-2-fluoro-N-[5-(4-fluorophenyl)-1,3,4-thiadiazol-2-yl]benzamide;
N-[5-(1,1-dimethylethyl)-1,3,4-thiadiazol-2-yl]-2-fluoro-5-{[(2,2,2-trifluoroethyl)amino]sulfonyl}benzamide;
2-fluoro-N-[5-(4-fluorophenyl)-1,3,4-thiadiazol-2-yl]-5-{[(2,2,2-trifluoroethyl)amino]sulfonyl}benzamide;
N-[5-(1,1-dimethylethyl)-1,3,4-thiadiazol-2-yl]-5-[(ethylamino)sulfonyl]-2,3-difluorobenzamide;
N-[5-(1,1-dimethylethyl)-1,3,4-thiadiazol-2-yl]-5-[(ethylamino)sulfonyl]-2-fluorobenzamide;
5-[(ethylamino)sulfonyl]-2,3-difluoro-N-[5-(1-methyl-1-phenylethyl)-1,3,4-thiadiazol-2-yl]benzamide;
2-fluoro-N-[5-(4-fluorophenyl)-1,3,4-thiadiazol-2-yl]-5-[(phenylamino)sulfonyl]benzamide;
5-(aminosulfonyl)-4-chloro-2-fluoro-N-[5-(4-fluorophenyl)-1,3,4-thiadiazol-2-yl]benzamide;
2,3-dichloro-5-[(ethylamino)sulfonyl]-N-[5-(1-methyl-1-phenylethyl)-1,3,4-thiadiazol-2-yl]benzamide;
2,3-dichloro-N-[5-(1,1-dimethylethyl)-1,3,4-thiadiazol-2-yl]-5-[(ethylamino)sulfonyl]benzamide;
2,3-dichloro-5-[(ethylamino)sulfonyl]-N-[5-(4-fluorophenyl)-1,3,4-thiadiazol-2-yl]benzamide;
2-bromo-5-[(ethylamino)sulfonyl]-N-[5-(4-fluorophenyl)-1,3,4-thiadiazol-2-yl]benzamide;
2-bromo-N-[5-(4-fluorophenyl)-1,3,4-thiadiazol-2-yl]-5-[(propylamino)sulfonyl]benzamide;
5-(aminosulfonyl)-2,3-dichloro-N-[5-(1-methyl-1-phenylethyl)-1,3,4-thiadiazol-2-yl]benzamide;
5-(aminosulfonyl)-2-chloro-N-[5-(1-methyl-1-phenylethyl)-1,3,4-thiadiazol-2-yl]benzamide;
5-(aminosulfonyl)-4-chloro-2-fluoro-N-[5-(4-fluorophenyl)-1,3,4-thiadiazol-2-yl]benzamide;
5-(aminosulfonyl)-2,4-dichloro-N-[5-(4-fluorophenyl)-1,3,4-thiadiazol-2-yl]benzamide;
5-(aminosulfonyl)-N-[5-(1,1-dimethylethyl)-1,3,4-thiadiazol-2-yl]-2-fluorobenzamide;
N-[5-(1,1-dimethylethyl)-1,3,4-thiadiazol-2-yl]-2-fluoro-5-{[(1-methylethyl)amino]sulfonyl}benzamide;
5-[(cyclopropylamino)sulfonyl]-N-[5-(1,1-dimethylethyl)-1,3,4-thiadiazol-2-yl]-2-fluorobenzamide;
N-[5-(1,1-dimethylethyl)-1,3,4-thiadiazol-2-yl]-2-fluoro-5-[(methylamino)sulfonyl]benzamide;
2-bromo-N-[5-(1,1-dimethylethyl)-1,3,4-thiadiazol-2-yl]-5-[(methylamino)sulfonyl]benzamide;
5-(aminosulfonyl)-2-fluoro-N-[5-(4-fluorophenyl)-1,3,4-thiadiazol-2-yl]benzamide;
2-fluoro-N-[5-(4-fluorophenyl)-1,3,4-thiadiazol-2-yl]-5-{[(1-methylethyl)amino]sulfonyl}benzamide;
5-[(cyclopropylamino)sulfonyl]-2-fluoro-N-[5-(4-fluorophenyl)-1,3,4-thiadiazol-2-yl]benzamide;
2-fluoro-N-[5-(4-fluorophenyl)-1,3,4-thiadiazol-2-yl]-5-[(methylamino)sulfonyl]benzamide;
2-fluoro-N-[5-(1-methyl-1-phenylethyl)-1,3,4-thiadiazol-2-yl]-5-{[(3,3,3-trifluoropropyl)amino]sulfonyl}benzamide;
5-[(cyclopropylamino)sulfonyl]-2-fluoro-N-[5-(1-methyl-1-phenylethyl)-1,3,4-thiadiazol-2-yl]benzamide;
N-[5-(1,1-dimethyl-2-phenylethyl)-1,3,4-thiadiazol-2-yl]-5-[(ethylamino)sulfonyl]-2-fluorobenzamide;
5-[(ethylamino)sulfonyl]-2-fluoro-N-{5-[1-(4-fluorophenyl)cyclopentyl]-1,3,4-thiadiazol-2-yl}benzamide;

5-[(ethylamino)sulfonyl]-2-fluoro-N-[5-(1-phenylcyclopentyl)-1,3,4-thiadiazol-2-yl]benzamide;
5-[(ethylamino)sulfonyl]-2-fluoro-N-[5-(1-phenylcyclopropyl)-1,3,4-thiadiazol-2-yl]benzamide;
5-[(cyclopropylamino)sulfonyl]-2-fluoro-N-{5-[1-(4-fluorophenyl)cyclopentyl]-1,3,4-thiadiazol-2-yl}benzamide;
5-(aminosulfonyl)-2-chloro-N-{5-[1-(4-fluorophenyl)-1-methylethyl]-1,3,4-thiadiazol-2-yl}benzamide;
5-[(cyclopropylamino)sulfonyl]-N-[5-(1,1-dimethyl-2-phenylethyl)-1,3,4-thiadiazol-2-yl]-2-fluorobenzamide;
5-[(ethylamino)sulfonyl]-2-fluoro-N-[5-(1-methylcyclohexyl)-1,3,4-thiadiazol-2-yl]benzamide;
N-(5-cyclopentyl-1,3,4-thiadiazol-2-yl)-5-[(ethylamino)sulfonyl]-2-fluorobenzamide;
5-[(ethylamino)sulfonyl]-2-fluoro-N-[5-(1-methylcyclopentyl)-1,3,4-thiadiazol-2-yl]benzamide;
N-[5-(4,4-difluorocyclohexyl)-1,3,4-thiadiazol-2-yl]-5-[(ethylamino)sulfonyl]-2-fluorobenzamide;
5-(aminosulfonyl)-2-fluoro-N-[5-(1-methyl-1-phenylethyl)-1,3,4-thiadiazol-2-yl]benzamide;
5-[(ethylamino)sulfonyl]-2-fluoro-N-[5-(1-phenylethyl)-1,3,4-thiadiazol-2-yl]benzamide;
5-[(ethylamino)sulfonyl]-2-fluoro-N-{5-[1-(2-fluorophenyl)-1-methylethyl]-1,3,4-thiadiazol-2-yl}benzamide;
5-[(ethylamino)sulfonyl]-2,3-difluoro-N-{5-[1-(2-fluorophenyl)-1-methylethyl]-1,3,4-thiadiazol-2-yl}benzamide;
5-[(ethylamino)sulfonyl]-2,3-difluoro-N-[5-(1-phenylcyclopentyl)-1,3,4-thiadiazol-2-yl]benzamide;
5-[(ethylamino)sulfonyl]-2,3-difluoro-N-[5-(1-methylcyclopentyl)-1,3,4-thiadiazol-2-yl]benzamide;
5-(aminosulfonyl)-N-{5-[1-(4-bromophenyl)-1-methylethyl]-1,3,4-thiadiazol-2-yl}-2-fluorobenzamide;
5-(aminosulfonyl)-2-fluoro-N-{5-[2-fluoro-4-(trifluoromethyl)phenyl]-1,3,4-thiadiazol-2-yl}benzamide;
5-(aminosulfonyl)-N-[5-(2-chloro-4-fluorophenyl)-1,3,4-thiadiazol-2-yl]-2-fluorobenzamide;
N-[5-(2-chloro-4-fluorophenyl)-1,3,4-thiadiazol-2-yl]-2-fluoro-5-{[(2,2,2-trifluoroethyl)amino]sulfonyl}benzamide;
2-fluoro-N-[5-(2-methyl-3-furanyl)-1,3,4-thiadiazol-2-yl]-5-{[(2,2,2-trifluoroethyl)amino]sulfonyl}benzamide;
2-fluoro-N-{5-[1-(3-fluorophenyl)cyclobutyl]-1,3,4-thiadiazol-2-yl}-5-{[(2,2,2-trifluoroethyl)amino]sulfonyl}benzamide;
2-fluoro-5-{[(2,2,2-trifluoroethyl)amino]sulfonyl}-N-{5-[1-(trifluoromethyl)cyclopentyl]-1,3,4-thiadiazol-2-yl}benzamide;
5-[(ethylamino)sulfonyl]-2-fluoro-N-{5-[1-(trifluoromethyl)cyclopentyl]-1,3,4-thiadiazol-2-yl}benzamide;
5-{[(cyclopropylmethyl)amino]sulfonyl}-2-fluoro-N-{5-[1-(trifluoromethyl)cyclopentyl]-1,3,4-thiadiazol-2-yl}benzamide;
5-[(ethylamino)sulfonyl]-2-fluoro-N-{5-[1-(3-fluorophenyl)cyclobutyl]-1,3,4-thiadiazol-2-yl}benzamide;
5-{[(cyclopropylmethyl)amino]sulfonyl}-2-fluoro-N-{5-[1-(3-fluorophenyl)cyclobutyl]-1,3,4-thiadiazol-2-yl}benzamide;
5-(aminosulfonyl)-2-fluoro-N-{5-[1-(3-fluorophenyl)cyclobutyl]-1,3,4-thiadiazol-2-yl}benzamide;
5-{[(cyclopropylmethyl)amino]sulfonyl}-2-fluoro-N-[5-(2-methyl-3-furanyl)-1,3,4-thiadiazol-2-yl]benzamide;
5-{[(cyclopropylmethyl)amino]sulfonyl}-2-fluoro-N-[5-(3-methyl-2-thienyl)-1,3,4-thiadiazol-2-yl]benzamide;
N-[5-(2,5-dimethyl-3-furanyl)-1,3,4-thiadiazol-2-yl]-5-[(ethylamino)sulfonyl]-2-fluorobenzamide;
5-{[(cyclopropylmethyl)amino]sulfonyl}-N-[5-(2,5-dimethyl-3-furanyl)-1,3,4-thiadiazol-2-yl]-2-fluorobenzamide;
N-[5-(4-chloro-2-fluorophenyl)-1,3,4-thiadiazol-2-yl]-5-{[(cyclopropylmethyl)amino]sulfonyl}-2-fluorobenzamide;
5-{[(cyclopropylmethyl)amino]sulfonyl}-2-fluoro-N-{5-[2-fluoro-4-(trifluoromethyl)phenyl]-1,3,4-thiadiazol-2-yl}benzamide;
5-{[(cyclopropylmethyl)amino]sulfonyl}-2-fluoro-N-[5-(2,3,4,5-tetrafluorophenyl)-1,3,4-thiadiazol-2-yl]benzamide;
N-{5-[1-(4-bromophenyl)-1-methylethyl]-1,3,4-thiadiazol-2-yl}-5-{[(cyclopropylmethyl)amino]sulfonyl}-2-fluorobenzamide;
N-[5-(2-chloro-4-fluorophenyl)-1,3,4-thiadiazol-2-yl]-5-{[(cyclopropylmethyl)amino]sulfonyl}-2-fluorobenzamide;
2-fluoro-N-[5-(1-phenylcyclobutyl)-1,3,4-thiadiazol-2-yl]-5-{[(2,2,2-trifluoroethyl)amino]sulfonyl}benzamide;
5-(aminosulfonyl)-2-fluoro-N-[5-(1-phenylcyclobutyl)-1,3,4-thiadiazol-2-yl]benzamide;
5-(aminosulfonyl)-2-fluoro-N-{5-[1-(4-fluorophenyl)cyclobutyl]-1,3,4-thiadiazol-2-yl}benzamide;
5-(aminosulfonyl)-2-fluoro-N-{5-[1-(trifluoromethyl)cyclobutyl]-1,3,4-thiadiazol-2-yl}benzamide;
5-[(ethylamino)sulfonyl]-2-fluoro-N-[5-(1-phenylcyclobutyl)-1,3,4-thiadiazol-2-yl]benzamide;
5-[(ethylamino)sulfonyl]-2-fluoro-N-{5-[1-(4-fluorophenyl)cyclobutyl]-1,3,4-thiadiazol-2-yl}benzamide;
5-[(ethylamino)sulfonyl]-2-fluoro-N-(5-{1-[3-(trifluoromethyl)phenyl]cyclobutyl}-1,3,4-thiadiazol-2-yl)benzamide;
5-{[(cyclopropylmethyl)amino]sulfonyl}-2-fluoro-N-[5-(1-phenylcyclobutyl)-1,3,4-thiadiazol-2-yl]benzamide;
5-{[(cyclopropylmethyl)amino]sulfonyl}-N-{5-[1-(2,4-difluorophenyl)cyclobutyl]-1,3,4-thiadiazol-2-yl}-2-fluorobenzamide;
2-fluoro-N-{5-[1-(2-fluorophenyl)cyclobutyl]-1,3,4-thiadiazol-2-yl}-5-{[(2,2,2-trifluoroethyl)amino]sulfonyl}benzamide;
5-(aminosulfonyl)-N-{5-[1-(2,4-difluorophenyl)cyclobutyl]-1,3,4-thiadiazol-2-yl}-2-fluorobenzamide;
5-([(cyclopropylmethyl)amino]sulfonyl)-2-fluoro-N-(5-{1-[3-(trifluoromethyl)phenyl]cyclobutyl}-1,3,4-thiadiazol-2-yl)benzamide;
5-(aminosulfonyl)-2-fluoro-N-{5-[1-(3-methylphenyl)cyclobutyl]-1,3,4-thiadiazol-2-yl}benzamide;
2-fluoro-N-{5-[1-(3-methylphenyl)cyclobutyl]-1,3,4-thiadiazol-2-yl}-5-{[(2,2,2-trifluoroethyl)amino]sulfonyl}benzamide;
5-[(ethylamino)sulfonyl]-2-fluoro-N-{5-[1-(3-methylphenyl)cyclobutyl]-1,3,4-thiadiazol-2-yl}benzamide;
5-{[(cyclopropylmethyl)amino]sulfonyl}-2-fluoro-N-{5-[1-(3-methylphenyl)cyclobutyl]-1,3,4-thiadiazol-2-yl}benzamide;
N-(5-cyclobutyl-1,3,4-thiadiazol-2-yl)-2-fluoro-5-{[(2,2,2-trifluoroethyl)amino]sulfonyl}benzamide;
N-{5-[1-(4-chlorophenyl)cyclobutyl]-1,3,4-thiadiazol-2-yl}-2-fluoro-5-{[(2,2,2-trifluoroethyl)amino]sulfonyl}benzamide;
N-{5-[1-(4-chlorophenyl)cyclobutyl]-1,3,4-thiadiazol-2-yl}-5-[(ethylamino)sulfonyl]-2-fluorobenzamide;
2-fluoro-N-[5-(1-methyl-1-phenylethyl)-1,3,4-thiadiazol-2-yl]-5-{[(2,2,2-trifluoroethyl)amino]sulfonyl}benzamide;
2-fluoro-5-{[(2-fluoroethyl)amino]sulfonyl}-N-[5-(1-methyl-1-phenylethyl)-1,3,4-thiadiazol-2-yl]benzamide; and 5-[(cyclobutylamino)sulfonyl]-2-fluoro-N-[5-(4-fluorophenyl)-1,3,4-thiadiazol-2-yl]benzamide;
or a pharmaceutically acceptable salt thereof.

In one embodiment, the present compound is selected from the group consisting of:
N-[5-(2-chloro-4-fluorophenyl)-1,3,4-thiadiazol-2-yl]-5-{[(cyclopropylmethyl)amino]sulfonyl}-2-fluorobenzamide;
3-chloro-N-[5-(1,1-dimethylethyl)-1,3,4-thiadiazol-2-yl]-5-[(ethylamino)sulfonyl]-2-fluorobenzamide;
5-[(cyclopropylamino)sulfonyl]-2-fluoro-N-[5-(4-fluorophenyl)-1,3,4-thiadiazol-2-yl]benzamide;
N-(5-cyclopentyl-1,3,4-thiadiazol-2-yl)-5-[(ethylamino)sulfonyl]-2-fluorobenzamide;
5-[(ethylamino)sulfonyl]-2,3-difluoro-N-[5-(1-phenylcyclopentyl)-1,3,4-thiadiazol-2-yl]benzamide;
N-[5-(2-chloro-4-fluorophenyl)-1,3,4-thiadiazol-2-yl]-2-fluoro-5-{[(2,2,2-trifluoroethyl)amino]sulfonyl}benzamide;
5-{[(cyclopropylmethyl)amino]sulfonyl}-2-fluoro-N-[5-(1-phenylcyclobutyl)-1,3,4-thiadiazol-2-yl]benzamide;
5-[(ethylamino)sulfonyl]-2,3-difluoro-N-[5-(4-fluorophenyl)-1,3,4-thiadiazol-2-yl]benzamide;
2-fluoro-N-[5-(4-fluorophenyl)-1,3,4-thiadiazol-2-yl]-5-[(methylamino)sulfonyl]benzamide;
5-[(cyclopropylamino)sulfonyl]-2-fluoro-N-[5-(1-methyl-1-phenylethyl)-1,3,4-thiadiazol-2-yl]benzamide;
N-[5-(1,1-dimethyl-2-phenylethyl)-1,3,4-thiadiazol-2-yl]-5-[(ethylamino)sulfonyl]-2-fluorobenzamide;
5-[(ethylamino)sulfonyl]-2-fluoro-N-[5-(1-methylcyclopentyl)-1,3,4-thiadiazol-2-yl]benzamide;
5-[(ethylamino)sulfonyl]-2,3-difluoro-N-{5-[1-(2-fluorophenyl)-1-methylethyl]-1,3,4-thiadiazol-2-yl}benzamide;
5-[(ethylamino)sulfonyl]-2,3-difluoro-N-[5-(1-methylcyclopentyl)-1,3,4-thiadiazol-2-yl]benzamide;
5-[(butylamino)sulfonyl]-2-fluoro-N-[5-(4-fluorophenyl)-1,3,4-thiadiazol-2-yl]benzamide;
2-fluoro-N-[5-(1-methyl-1-phenylethyl)-1,3,4-thiadiazol-2-yl]-5-{[(3,3,3-trifluoropropyl)amino]sulfonyl}benzamide;
5-[(ethylamino)sulfonyl]-2-fluoro-N-[5-(1-phenylcyclopentyl)-1,3,4-thiadiazol-2-yl]benzamide;
5-[(cyclobutylamino)sulfonyl]-2-fluoro-N-[5-(4-fluorophenyl)-1,3,4-thiadiazol-2-yl]benzamide;
3-chloro-5-[(ethylamino)sulfonyl]-2,4-difluoro-N-[5-(4-fluorophenyl)-1,3,4-thiadiazol-2-yl]benzamide;
5-[(ethylamino)sulfonyl]-2,3,4-trifluoro-N-[5-(1-methyl-1-phenylethyl)-1,3,4-thiadiazol-2-yl]benzamide;
2-fluoro-N-[5-(4-fluorophenyl)-1,3,4-thiadiazol-2-yl]-5-{[(2-methylpropyl)amino]sulfonyl}benzamide;
2-fluoro-N-[5-(4-fluorophenyl)-1,3,4-thiadiazol-2-yl]-5-[(propylamino)sulfonyl]benzamide;
N-[5-(1,1-dimethylethyl)-1,3,4-thiadiazol-2-yl]-5-[(ethylamino)sulfonyl]-2,3-difluorobenzamide;
2-fluoro-N-{5-[1(3-fluorophenyl)cyclobutyl]-1,3,4-thiadiazol-2-yl}-5-{[(2,2,2-trifluoroethyl)amino]sulfonyl}benzamide; and
5-(aminosulfonyl)-2-fluoro-N-{5-[1-(3-methylphenyl)cyclobutyl]-1,4-thiadiazol-2-yl}benzamide;
or a pharmaceutically acceptable salt thereof.

Because of their potential use in medicine, the salts of the compounds of Formula (I) are pharmaceutically acceptable. Suitable pharmaceutically acceptable salts include acid or base addition salts.

A pharmaceutically acceptable acid addition salt may be formed by reaction of a compound of Formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic or hexanoic acid), optionally in a suitable solvent such as an organic solvent, to give the salt which is usually isolated for example by crystallization and filtration.

A pharmaceutically acceptable acid addition salt of a compound of Formula (I) may be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate or hexanoate salt.

A pharmaceutically acceptable base addition salt may be formed by reaction of a compound of Formula (I) with a suitable organic base (e.g. triethylamine, ethanolamine, triethanolamine, choline, arginine, lysine or histidine), optionally in a suitable solvent such as an organic solvent, to give the base addition salt which is usually isolated for example by crystallization and filtration. Other suitable pharmaceutically acceptable salts include pharmaceutically acceptable metal salts, for example pharmaceutically acceptable alkali-metal or alkaline-earth-metal salts such as sodium, potassium, calcium or magnesium salts.

Methods of Preparation

The present compounds may be synthesized by a method comprising the step of reacting a 5-substituted-1,3,4-thiadiazol-2-amines according to Formula (II):

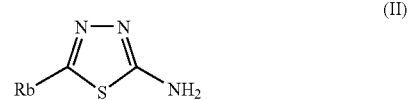

with a substituted aminosulfonyl benzoic acid according to Formula (III):

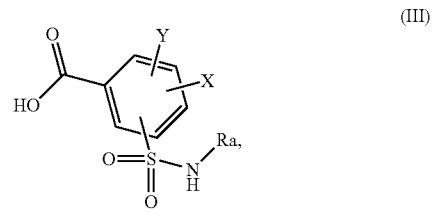

wherein Y, X, Ra and Rb are as defined in Formula (I), hereinabove, to yield the Formula (I) compound.

The following abbreviations are used in the examples and specification:
TLC—thin layer chromatography;
TEA—triethylamine;
TFA—trifluoroacetic acid;
TFAA—trifluoroacetic anhydride;
THF—tetrahydrofuran;
DMSO—dimethylsulfoxide;
AcOEt or EtOAc—ethyl acetate;
DME—1,2-dimethoxyethane;
DCM—dichloromethane;
DCE—dichloroethane;

DMF—N,N-dimethylformamide;
EDC—N-[3-(dimethylamino)propyl]-N'-ethylcarbodiimide hydrochloride;
HOBt—1H-1,2,3-benzotriazol-1-ol hydrate;
HOAt—1H-[1,2,3]triazolo[4,5-b]pyridin-1-ol;
PS-DCC—polymer-supported dicyclohexylcarbodiimide;
PS-HOBt—polymer-supported 1H-1,2,3-benzotriazol-1-ol
DIPEA—diisopropylethylamine; and
LiHMDS—lithium hexamethyldisilazide.

5-Substituted-1,3,4-thiadiazol-2-amines 1 are reacted with substituted aminosulfonyl benzoic acids 2 to yield aminosulfonyl benzamides 3 (Scheme 1).

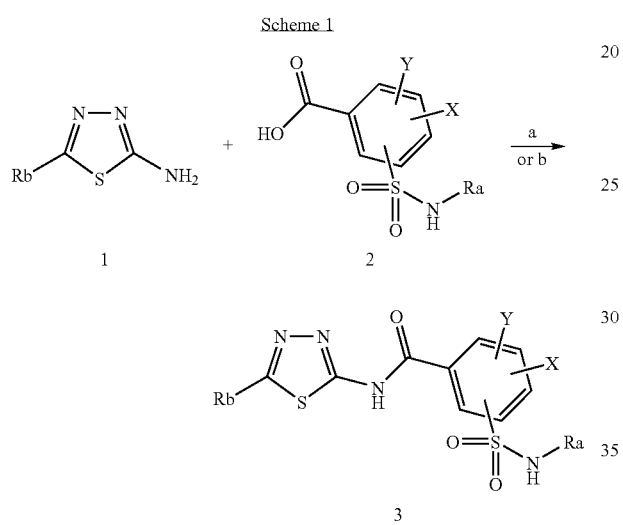

Conditions: a) EDC, HOAt, DCM/DMF, rt or heating; b) PS-DCC, PS-HOBt, THF, rt.

5-Substituted-1,3,4-thiadiazol-2-amines 1 are prepared from acids 4 and thiosemicarbarmate 5 by cyclization according to Scheme 2.

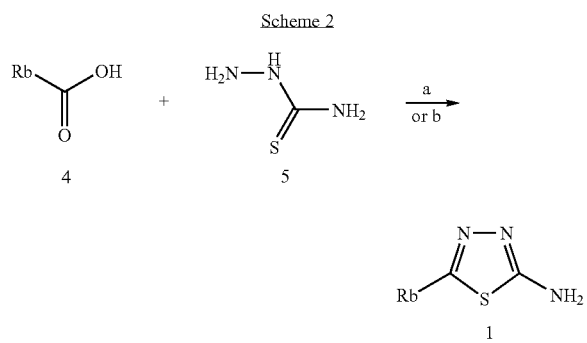

Conditions: a) POCl₃, 100° C.; b) conc. HCl, heating.

Alternatively, 5-substituted-1,3,4-thiadiazol-2-amines 1 are prepared from nitriles 6 and thiosemicarbarmate 5 by cyclization under acidic condition according to Scheme 2a.

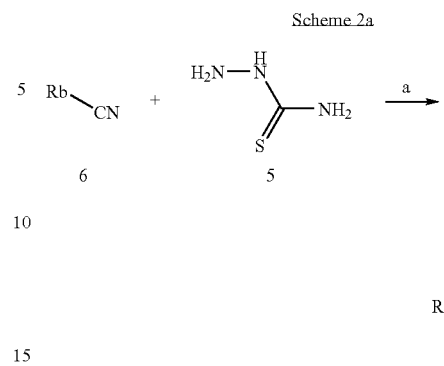

Conditions: a) TFA, heating

Commercially unavailable acids such as 4a can additionally be made from nitriles 6a according to Scheme 3.

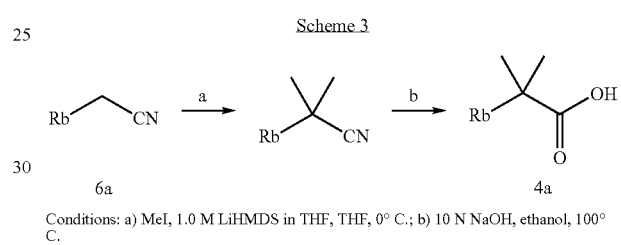

Conditions: a) MeI, 1.0 M LiHMDS in THF, THF, 0° C.; b) 10 N NaOH, ethanol, 100° C.

Substituted aminosulfonyl benzoic acids 2 can be prepared from sulfonyl chlorides 8, which can be prepared by converting the corresponding benzoic acids 7 (Scheme 4).

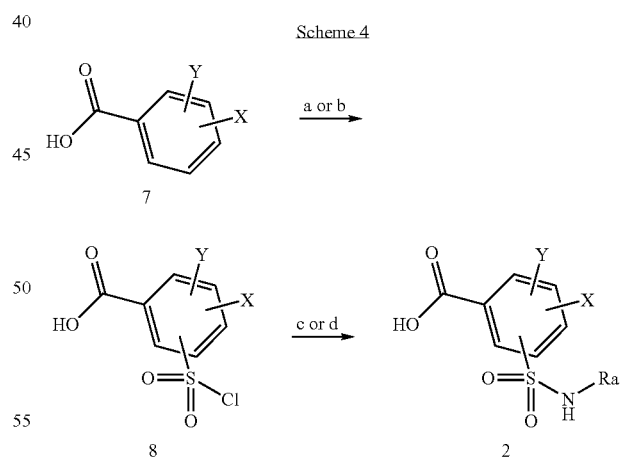

Conditions: a) HSO₃Cl, 160° C.; b) HSO₃Cl, 200° C., microwave; c) base, CHCl₃, THF, NH₂Rb, rt; d) base, THF, RaNH₂, rt or heating The aminosulfonyl benzamides 3, with Rb being non-aromatic, can be prepared by an alternative route shown in Scheme 5. 5-Substituted-1,3,4-thiadiazol-2-amines 1 react with substituted benzoic acids 7 to yield benzamides 9, which, upon chlorosulfonylation, give sulfonylchlorides 10. Sulfonamide formation of 10 occurs with a variety of amines to afford aminosulfonyl benzamide 3 (Scheme 5).

Scheme 5

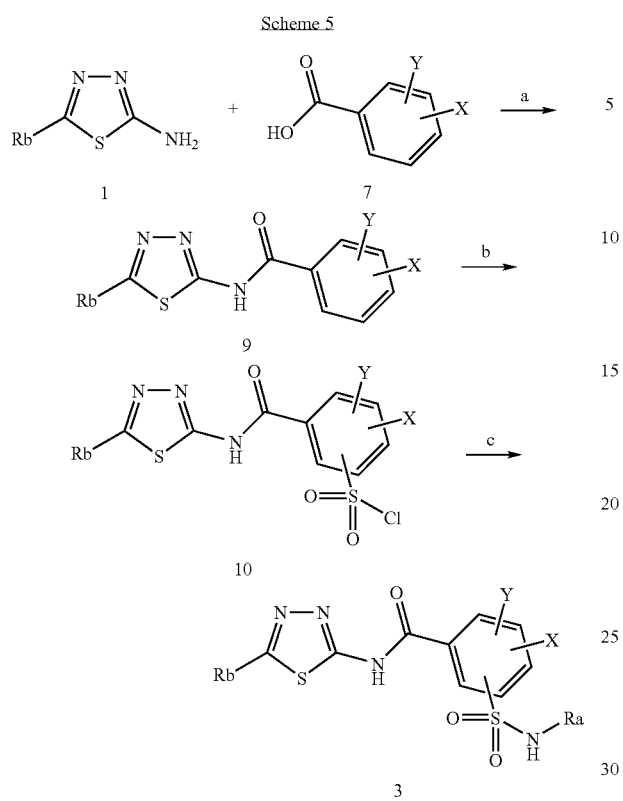

Conditions: a) EDC, HAOt, DCM/DMF, rt or heating; b) HSO₃Cl, 200° C., microwave; c) base, THF, RaNH₂, rt or heating.

Phenylcyclobutyl thiadiazolamine is prepared by the cyclization of dibromopropane followed by hydrolysis showed in Scheme 6.

Scheme 6

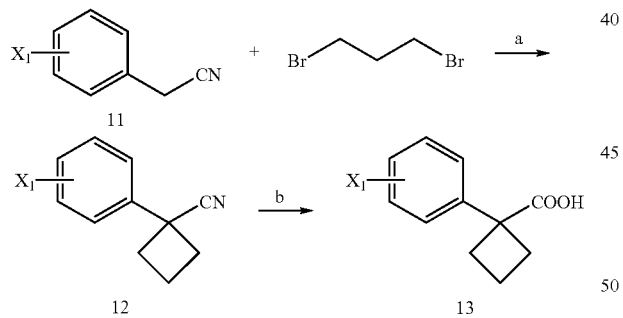

wherein $X_1$ represents halogen;
Conditions: a) NaH, DMF, 0° - rt; b) KOH, 160° C., microwave.

SYNTHETIC EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Unless otherwise noted, all starting materials were obtained from commercial suppliers and used without further purification. Unless otherwise indicated, all temperatures are expressed in ° C. (degrees Centigrade). Unless otherwise indicated, all reactions are conducted under an inert atmosphere at room temperature. For reverse phase HPLC purification (unless otherwise stated), a 50×20 mm I. D. Luna C18 5υ column using acetonitrile containing 0.1% TFA and water containing 0.1% TFA and UV detection at 215 nM and 254 nM was used.

Nuclear magnetic resonance spectra were recorded at 400 MHz using a Bruker AC 400 spectrometer. CDCl₃ is deuteriochloroform, DMSO-d₆ is hexadeuteriodimethylsulfoxide, and CD₃OD is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on a PE Sciex Single Quadrupole LC/MS API-150 using electrospray (ES) ionization techniques. Elemental analyses were obtained using a Perkin-Elmer 240C elemental analyzer.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel.

EXAMPLE 1

Preparation of 5-[(ethylamino)sulfonyl]-2-fluoro-N-[5-(1-methyl-1-phenylethyl)-1,3,4-thiadiazol-2-yl]benzamide

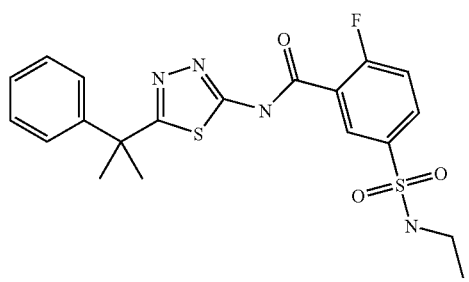

Intermediate 1

5-(Chlorosulfonyl)-2-fluorobenzoic acid (General Procedure 1)

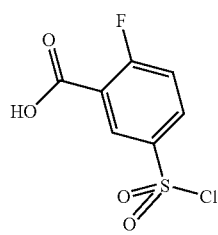

5-(Chlorosulfonyl)-2-fluorobenzoic acid was prepared from 2-fluorobenzoic acid using a Biotage Initiator 8 microwave set to high absorbance as follows. Using conditions described, the reaction typically reached a pressure of 12 barr. The pressure was reduced to 3 barr after cooling and was vented prior to decapping the reaction vessel. To a 5 ml Biotage microwave reaction tube was added 2-fluorobenzoic acid (0.5 g, 3.57 mmol) and a Teflon covered magnetic stir-bar. To this was added 2 ml of chlorosulfuric acid. The vessel was capped and heated to 200° C. for 3.25 min. After cooling to room temperature, the remaining pressure was vented into a 50 ml syringe and discharged into 30 ml 1M NaOH. Reaction was quenched by adding dropwise to 30 ml of crushed ice. The solid product was collected by vacuum filtration, washed with water (5 ml, 3×) and air-dried under vacuum for 2 h, yielding 5-(chlorosulfonyl)-2-fluorobenzoic acid as a light yellow solid.

MS (ESI): 238.9 $[M+H]^+$.

Intermediate 2

5-[(Ethylamino)sulfonyl]-2-fluorobenzoic acid
(General Procedure 2)

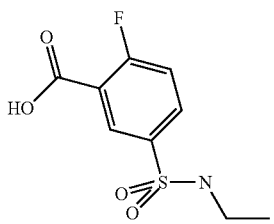

To a 5 ml Biotage microwave reaction tube was added 5-(chlorosulfonyl)-2-fluorobenzoic acid (0.4 g, 1.68 mmol) and a Teflon covered magnetic stir-bar followed by 2.5 ml of THF. To the resulting mixture was added 10N aqueous NaOH (0.369 ml, 3.38 mmol) with stirring. After formation of a cloudy suspension, ethylamine (0.838 ml, 1.68 mmol) was added as a 2M solution in THF. The reaction vessel was capped and heated to 110° C. for 1.1 min in a Biotage Initiator 8 microwave set at high absorbance. Reaction mixture was then diluted with 4 ml acetonitrile and acidified with 6M aqueous HCl (0.670 ml, 4.02 mmol). Water was removed from the mixture by adding excess anhydrous $Na_2SO_4$ and subsequent filtration. The filtered was washed with acetonitrile and DMF. The combined filtrates were concentrated with rotary evaporation, yielding the crude 5-[(ethylamino)sulfonyl]-2-fluorobenzoic acid.

MS (ESI): 247.8 $[M+H]^+$, Rt 0.70 min

Intermediate 3

5-(1-Methyl-1-phenylethyl)-1,3,4-thiadiazol-2-amine
(General Procedure 3)

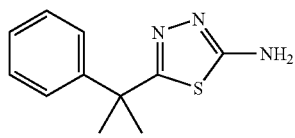

2-methyl-2-phenylpropanoic acid (164 mg, 1.0 mmol) and thiosemicarbamate (91 mg, 1.0 mmol) in a round bottom flask were added $POCl_3$ (154 mg, 1.0 mmol) dropwise. The reaction mixture was heated at 100° C. for three hours while being stirred vigorously. The progress of reaction was monitored by LCMS and TLC. After reaction was completed, the reaction mixture was concentrated in vacuo. Crude product of 5-(1-methyl-1-phenylethyl)-1,3,4-thiadiazol-2-amine with 82% of purity (by LC-MS) was carried on to next step without further purification.

5-[(Ethylamino)sulfonyl]-2-fluoro-N-[5-(1-methyl-1-phenylethyl)-1,3,4-thiadiazol-2-yl]benzamide
(General Procedure 4)

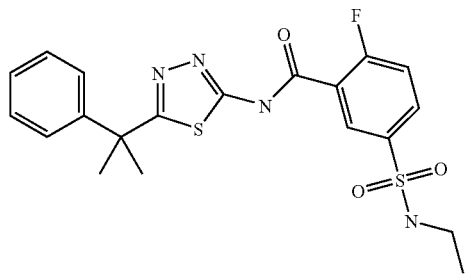

To the mixture of 5-[(ethylamino)sulfonyl]-2-fluorobenzoic acid (24.7 mg, 0.1 mmol), prepared according to Scheme 4, and above crude 5-(1-methyl-1-phenylethyl)-1,3,4-thiadiazol-2-amine (21.9 mg, 0.1 mmol) in 2.0 mL of mixed solvents (DCM:DMF=10:1) was added EDC (19.2 mg, 0.1 mmol) and HOAt (13.6 mg, 0.1 mmol). The resultant mixture was stirred at room temperature for overnight, and then concentrated in vacuo. The residue was purified by using a Gilson preparative HPLC system with a Waters Xterra (C-18) column 100 mm by 50 mm ID, eluting with 10% B to 90% B in 10 min, where $A=H_2O$ and $B=CH_3CN$ pumped at 150 mL/min to yield 5-[(ethylamino)sulfonyl]-2-fluoro-N-[5-(1-methyl-1-phenylethyl)-1,3,4-thiadiazol-2-yl]benzamide (7.0 mg).

MS (ESI): 449.1 $[M+H]^+$, Rt 2.02 min

EXAMPLE 2

Preparation of 5-(aminosulfonyl)-2-chloro-N-(5-cyclohexyl-1,3,4-thiadiazol-2-yl)benzamide

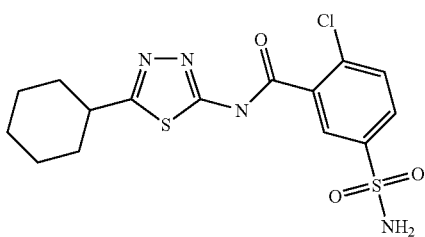

Intermediate 4

5-Cyclohexyl-1,3,4-thiadiazol-2-amine

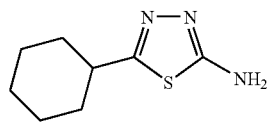

To a mixture of cyclohexanecarboxylic acid (1.28 g, 10 mmol) and thiosemicarbamate (0.91 g, 10 mmol) was added conc. HCl (20mmol). The reaction mixture was heated under reflux for three hours while being stirred vigorously. After reaction was completed, the mixture was cooled down to room temperature. The mixture was adjusted to pH=8~9 using 10N sodium hydroxide aqueous solution and cooled with ice-water for 15 minutes. The crude product of 5-cyclohexyl-1,3,4-thiadiazol-2-amine as precipitates was collected by vacuum filtration (1.05 g, 57%), and directly used for next reaction.

MS (ESI): 184 [M+H]+.

5-(aminosulfonyl)-2-chloro-N-(5-cyclohexyl-1,3,4-thiadiazol-2-yl)benzamide (General Procedure 5)

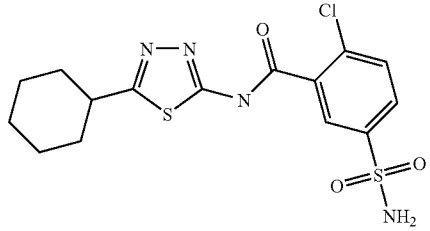

To a mixture of 5-(aminosulfonyl)-2-chlorobenzoic acid (33 mg, 0.14 mmol) in THF in a vial was added PS-DCC (0.1 g, 0.155 mmol), PS-HOBt (0.12 g, 0.159 mmol) and then above crude 5-cyclohexyl-1,3,4-thiadiazol-2-amine (30 mg, 0.16 mmol). The reaction mixture in the vial was shaken for overnight. The reaction slurry was diluted with more THF, and filtrated to remove polymer bound reagents. The filtrate was concentrated, and then the residue was purified by using a Gilson preparative HPLC system with a Water Xterra (C-18) column 100 mm by 50 mm ID, eluting with 2% B to 90% B in 10 minutes, where A=$H_2O$ and B=$CH_3CN$ pumped at 150 mL/min to yield 5-(aminosulfonyl)-2-chloro-N-(5-cyclohexyl-1,3,4-thiadiazol-2-yl)benzamide (2.75 mg).

MS (ESI): 401 [M+H]+

EXAMPLE 3

2-fluoro-N-{5-[1-(4-fluorophenyl)-1-methylethyl]-1,3,4-thiadiazol-2-yl}-5-{[(2,2,2-trifluoroethyl)amino]sulfonyl}benzamide

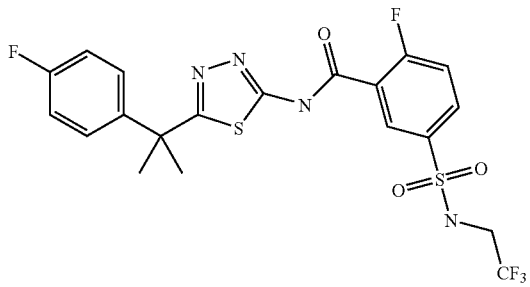

Intermediate 5

2-(4-Fluorophenyl)-2-methylpropanenitrile (General Procedure 6)

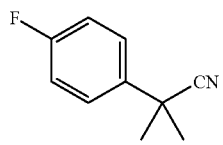

To a solution of commercially available 4-fluorophenylacetonitrile (2.71 g, 20 mmol) in 100 mL of THF at 0° C. was added 1.0 M lithium bis(trimethylsilyl) amide in THF (42 mL, 42 mmol). After the mixture was stirred at 0° C. for 30 minutes, methyl iodide (8.5 g, 60 mmol) was added, and reaction mixture was stirred at room temperature for overnight. Reaction was then quenched at 0° C. by adding saturated ammonium chloride solution (35 mL). The mixture was extracted with ether (50 mL×2). The combined organic layers were dried over sodium sulfate, and concentrated. Purification using column chromatography (hexane/ethyl acetate, 1/20, silica gel) led to 2-(4-fluorophenyl)-2-methylpropanenitrile (2.41 g, 74%).

MS (ESI): 164 [M+H]+.

Intermediate 6

2-(4-Fluorophenyl)-2-methylpropanoic acid (General Procedure 7)

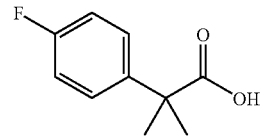

A solution of above 2-(4-fluorophenyl)-2-methylpropanenitrile (1.0 g, 6.1 mmol) in ethanol (1.5 mL) and 10N sodium hydroxide solution (1 mL) was stirred at 100° C. for overnight. After cooling, the reaction mixture was diluted with water (10 mL) and washed with ethyl acetate (10 mL). The aqueous layer was adjusted to pH=2-3 with concentrated HCl solution, and extracted with ethyl acetate (30 mL×2). The combined organic layers were then washed with brine, dried over sodium sulfate and concentrated in vacuo. Purification using column chromatography (dichloromethylene/methanol=10/1) to afford 2-(4-fluorophenyl)-2-methylpropanoic acid (0.37 g, 33%). 182.8 [M+H]+, rt 1.37 min.

Intermediate 7

5-[1-(4-Fluorophenyl)-1-methylethyl]-1,3,4-thiadiazol-2-amine

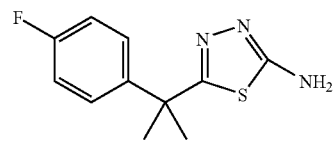

The above 2-(4-fluorophenyl)-2-methylpropanoic acid (273 mg, 1.5 mmol) and thiosemicarbarmate (136.5 mg, 1.5 mmol in a round bottom flask) were added to $POCl_3$ (231 mg, 1.5 mmol) dropwise. The mixture was heated at 100° C. for three hours while being stirred vigorously. The progress of reaction was monitored by LCMS and TLC. After reaction was completed, the reaction mixture was concentrated in vacco. Crude product of 5-[1-(4-fluorophenyl)-1-methylethyl]-1,3,4-thiadiazol-2-amine with 60% of purity (by LC- MS) was carried on to next step without further purification. MS (ESI): 237.6 [M+H]+, rt 1.46 min.

2-fluoro-N-{5-[1-(4-fluorophenyl)-1-methylethyl]-1,3,4-thiadiazol-2-yl}-5-{[(2,2,2-trifluoroethyl)amino]sulfonyl}benzamide

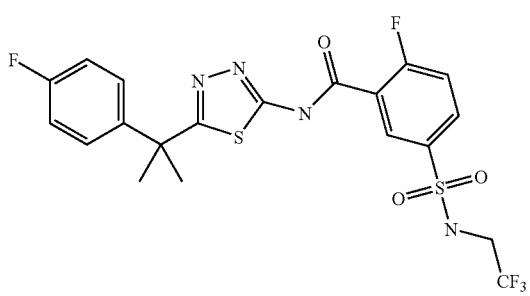

To 2-fluoro-5-{[(2,2,2-trifluoroethyl)amino]sulfonyl}benzoic acid (intermediate 25)(30.1 mg 0.1 mmol) and above 5-[1-(4-fluorophenyl)-1-methylethyl]-1,3,4-thiadiazol-2-amine (23.7 mg, 0.1 mmol) in 2.0 mL of mixed solvent (DCM:DMF=10:1) were added EDC (19.2 mg, 0.1 mmol) and HOAt (13.6 mg, 0.1 mmol). The resultant mixture was stirred at room temperature for overnight, and then concentrated in vacuo. The residue was purified by using a Gilson preparative HPLC system with a Waters Xterra (C-18) column 100 mm by 50 mm ID, eluting with 20% B to 99% B in 10 min, where A=H$_2$O and B=CH$_3$CN pumped at 150 mL/min to yield 5-[(ethylamino)sulfonyl]-2-fluoro-N-[5-(1-methyl-1-phenylethyl)-1,3,4-thiadiazol-2-yl]benzamide (2.6 mg).

MS (ESI): 521.4 [M+H]+, rt 2.29 min.

EXAMPLE 4

5-(aminosulfonyl)-2-chloro-N-[5-(4-fluorophenyl)-1,3,4-thiadiazol-2-yl]benzamide

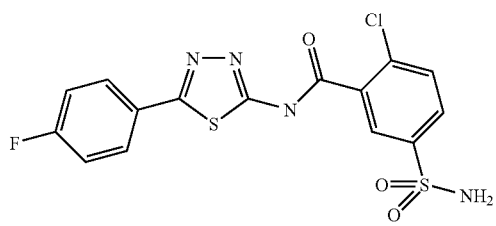

To a 20 ml scintillation vial containing a Teflon covered magnetic stir-bar was added commercially available 5-(4-fluorophenyl)-1,3,4-thiadiazol-2-amine (25 mg, 0.128 mmol) and 5-(aminosulfonyl)-2-chlorobenzoic acid (22.3 mg, 0.128 mmol). To this mixture was added EDC (25 mg, 0.128 mmol) and HOAt (18 mg, 0.128 mmol) followed by 3 ml of DCM. The resulting mixture was stirred at room temperature overnight. The product precipitated and was collected by vacuum filtration, washed with 3 ml of MeOH and air-dried under vacuum. Yield of 5-(aminosulfonyl)-2-chloro-N-[5-(4-fluorophenyl)-1,3,4-thiadiazol-2-yl]benzamide was (7 mg) as a white powder. MS (ESI): 413.1 [M+H]+, rt 1.80 min

EXAMPLE 5

5-(aminosulfonyl)-2,3-dichloro-N-[5-(4-fluorophenyl)-1,3,4-thiadiazol-2-yl]benzamide

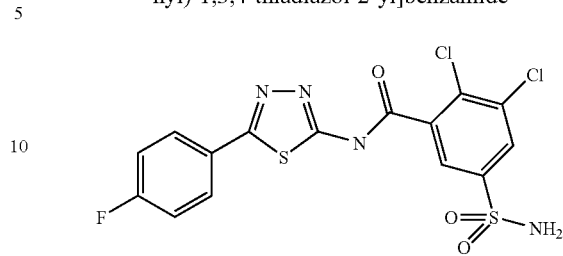

Intermediate 8

2,3-Dichloro-5-(chlorosulfonyl)benzoic acid

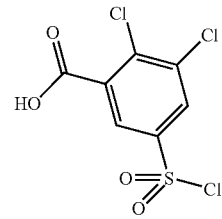

A 50 ml round bottom flask was purged with dry N$_2$ and kept under a low positive pressure of N$_2$ fed through a gas bubbler and chlorosulfuric acid (4 ml) was added via glass syringe. To this was added a Teflon covered magnetic stir-bar followed by 2,3-dichlorobenzoic acid (1 g, 5.2 mmol) in 3 portions over 1.5 minutes. The flask was equipped with a condenser and heated under N$_2$ to 155° C. in an aluminum heating block for 2.5 h with stirring. Reaction progress was monitored by LC-MS. After cooling in an ice bath, the reaction was quenched by adding to 210 ml of crushed ice dropwise. The product was collected by vacuum filtration, washed with 10 ml of water (3×), and air-dried under vacuum for 4 h. The yield of 2,3-dichloro-5-(chlorosulfonyl)benzoic acid was (982 mg, 65%) as a white solid.

MS (ESI): 288.8 [M+H]+.

Intermediate 9

5-(Aminosulfonyl)-2,3-dichlorobenzoic acid

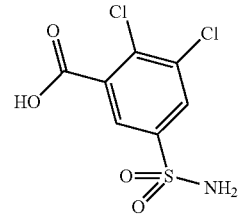

To a 20 ml scintillation vial was added 2,3-dichloro-5-(chlorosulfonyl)benzoic acid (170 mg, 0.587 mmol). To this was added 1.5 ml of DCM and 7 ml of 7M NH$_4$OH. The reaction mixture was stirred vigorously at room temperature overnight. After consumption of the starting material, the reaction solution was concentrated to half volume with a rotary evaporator and acidified with 6M HCl to ~pH 4.5. The resulting solution was left at room temperature until the product precipitated. The product was collected by vacuum filtration and air dried, yielding 5-(aminosulfonyl)-2,3-dichlorobenzoic acid (80 mg, 50%) as light yellow solid.

MS (ESI): 269.8 [M+H]$^+$, Rt 1.07 min 5-(Aminosulfonyl)-2,3-dichloro-N-[5-(4-fluorophenyl)-1,3,4-thiadiazol-2-yl]benzamide

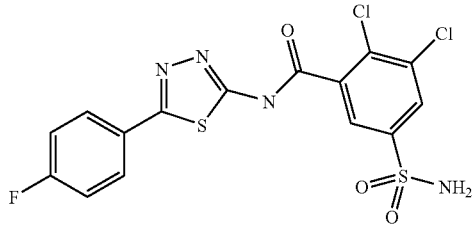

To a 20 ml scintillation vial was added 5-(aminosulfonyl)-2,3-dichlorobenzoic acid (40 mg, 0.148mmol) and commercially available 5-(4-fluorophenyl)-1,3,4-thiadiazol-2-amine (28.9 mg, 0.148 mmol). To this was added EDC (28 mg, 0.148 mmol) and HOAt (20 mg, 0.148 mmol) followed by 3 ml DCM. The reaction mixture was stirred with a Teflon covered magnetic stir-bar at room temperature for overnight. The product was collected by vacuum filtration and air dried, yielding 5-(aminosulfonyl)-2,3-dichloro-N-[5-(4-fluorophenyl)-1,3,4-thiadiazol-2-yl]benzamide (31 mg, 47%) as light tan solid.

MS (ESI): 446.8 [M+H]$^+$, Rt 2.00 min

EXAMPLE 6

5-[(ethylamino)sulfonyl]-2,3-difluoro-N-[5-(4-fluorophenyl)-1,3,4-thiadiazol-2-yl]benzamide

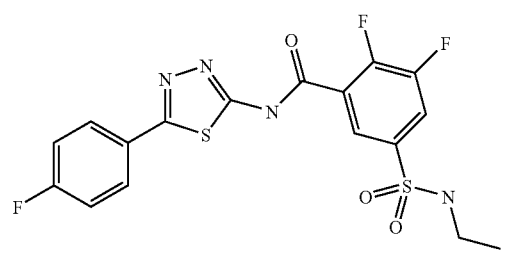

Intermediate 10

2,3-Difluro-5-(chlorosulfonyl)benzoic acid

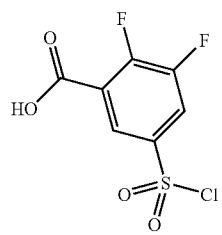

2,3-Difluro-5-(chlorosulfonyl)benzoic acid was prepared analogous to Example 5 beginning from 2,3-difluorobenzoic acid. 256.9 [M+H]$^+$.

Intermediate 11

5-[(Ethylamino)sulfonyl]-2,3-difluorobenzoic acid

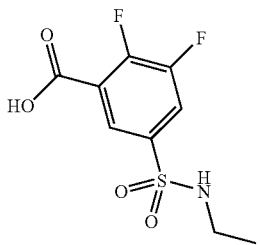

To a 5 ml Biotage microwave reaction tube was added 2,3-difluoro-5-(chlorosulfonyl)benzoic acid (100 mg, 0.390 mmol). To this was added 2 ml of THF followed with (0.08 ml, 0.818 mmol) 10M aqueous NaOH. To the resulting stirred mixture was added ethanamine (0.195 ml, 0.390 mmol) as a 2M solution in THF. The reaction mixture was heated with stirring to 110° C. for 1.1 minutes using a Biotage Initiator 8 microwave set for high absorbance. After reaction cooled to room temperature 6M aqueous HCl (0.150 ml, 0.896 mmol) was added with stirring. The water was removed from the mixture by adding excess anhydrous Na$_2$SO$_4$ and subsequent filtration. The filtered salts were washed with acetonitrile and DMF (19:1, 10 ml, 2×). The combined filtrates were concentrated with rotary evaporation, yielding a DMF solution of 5-[(ethylamino)sulfonyl]-2,3-difluorobenzoic acid (82% pure by LCMS, % purity used as stoichiometry for next step), which was carried forward without purification.

MS (EST): 266.0 [M+H]$^+$.

5-[(Ethylamino)sulfonyl]-2,3-difluoro-N-[5-(4-fluorophenyl)-1,3,4-thiadiazol-2-yl]benzamide

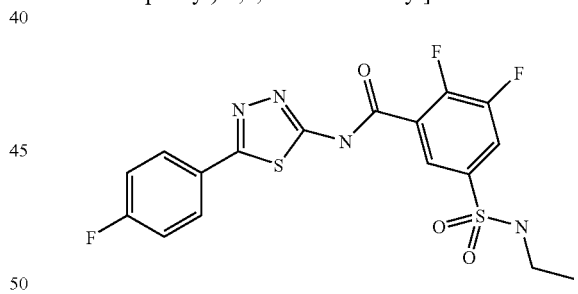

To a 20 ml scintillation vial was added EDC (54 mg, 0.283 mmol), HOAt (38 mg, 0.283 mmol) and commercially available 5-(4-fluorophenyl)-1,3,4-thiadiazol-2-amine (55 mg, 0.283 mmol). To this was added 5-[(ethylamino)sulfonyl]-2,3-difluorobenzoic acid as a solution in 2 ml DMF (75 mg, 0.283 mmol based on theoretical yield of preceding). The reaction mixture was stirred at room temperature overnight with a Teflon covered magnetic stir-bar. The reaction mixture was then concentrated to ~1 ml and the residue was purified using a Gilson preparative HPLC system with a Waters Xterra (C-18) column 100 mm by 50 mm ID, eluting with 30% B to 60% B in 10 min, where A=H$_2$O and B=CH$_3$CN pumped at 150 mL/min to yield 5-[(Ethylamino)sulfonyl]-2,3-difluoro-N-[5-(4-fluorophenyl)-1,3,4-thiadiazol-2-yl]benzamide as a white solid (12 mg, 19%).

MS (ESI): 443.0 [M+H]$^+$, Rt 2.10 min

EXAMPLE 7

5-[(ethylamino)sulfonyl]-2-fluoro-N-[5-(4-fluorophenyl)-1,3,4-thiadiazol-2-yl]benzamide

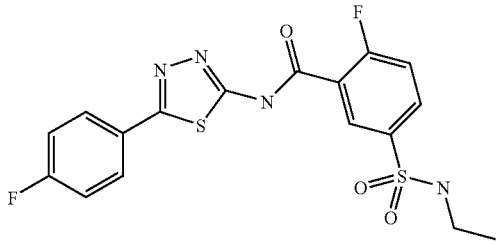

5-[(Ethylamino)sulfonyl]-2-fluoro-N-[5-(4-fluorophenyl)-1,3,4-thiadiazol-2-yl]benzamide was prepared from 5-[(ethylamino)sulfonyl]-2-fluorobenzoic acid in a manner analogous to Example 6 with the following exceptions. The 5-[(ethylamino)sulfonyl]-2-fluorobenzoic acid used was either obtained from the synthesis previously described.

MS (EST): 426.3 [M+H]$^+$, Rt 1.97 min

EXAMPLE 8

Preparation of 5-(aminosulfonyl)-N-(5-cyclopentyl-1,3,4-thiadiazol-2-yl)-2-fluorobenzamide

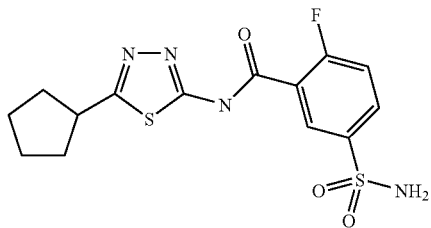

Intermediate 12

N-(5-cyclopentyl-1,3,4-thiadiazol-2-yl)-2-fluorobenzamide (General Procedure 8)

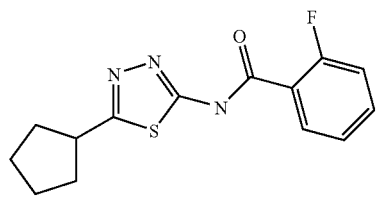

To a 20 ml scintillation vial was added 2-fluorobenzoic acid (845 mg, 5.0 mmol) and commercially available 5-cyclopentyl-1,3,4-thiadiazol-2-amine (intermediate 49) (700 mg, 5.0 mmol). To this was added EDC (960 mg, 5 0 mmol) and HOAt (675 mg, 5.0 mmol) followed by 25 ml DCM. The reaction mixture was stirred with a Teflon covered magnetic stir-bar at room temperature for overnight. The product was collected by ethyl acetate and 5% HCl solution work up, and then to purified by column (CH$_3$OH/DCM, 1-10% gradient system), yielding N-(5-cyclopentyl-1,3,4-thiadiazol-2-yl)-2-fluorobenzamide (0.61 g, 42%) as solid.

MS (ESI): 292 [M+H]$^+$.

Intermediate 13

3-{[(5-cyclopentyl-1,3,4-thiadiazol-2-yl)amino]carbonyl}-4-fluorobenzenesulfonyl chloride (General Procedure 9)

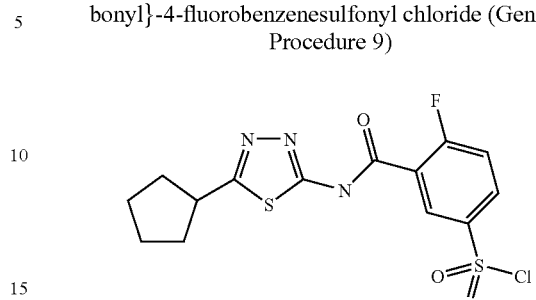

3-{[(5-cyclopentyl-1,3,4-thiadiazol-2-yl)amino]carbonyl}-4-fluorobenzenesulfonyl chloride was prepared from N-(5-cyclopentyl-1,3,4-thiadiazol-2-yl)-2-fluorobenzamide using a Biotage Initiator 8 microwave set to high absorbance as follows. Using conditions described, the reaction reached a pressure of 12 barr. The pressure was reduced to 3 barr after cooling and was vented prior to decapping the reaction vessel. To a 5 ml Biotage microwave reaction tube was added N-(5-cyclopentyl-1,3,4-thiadiazol-2-yl)-2-fluorobenzamide (0.305 g, 1.05 mmol) and a Teflon covered magnetic stir-bar. To this was added 2 ml of chlorosulfuric acid. The vessel was capped and heated to 200° C. for 3.25 min. After cooling to room temperature, the remaining pressure was vented into a 50 ml syringe and discharged into 30 ml 1M NaOH. Reaction was quenched by adding dropwise to 30 ml of crushed ice-water while stirring. The solid product was collected by vacuum filtration, washed with water (5 ml, 3×) and air-dried under vacuum, yielding 3-{[(5-cyclopentyl-1,3,4-thiadiazol-2-yl)amino]carbonyl}-4-fluorobenzenesulfonyl chloride as a off white solid (290 mg, 71%), Crude product was used to next step.

MS (ESI): 390.2 [M+H]$^+$, Rt 1.15 min.

5-(aminosulfonyl)-N-(5-cyclopentyl-1,3,4-thiadiazol-2-yl)-2-fluorobenzamide

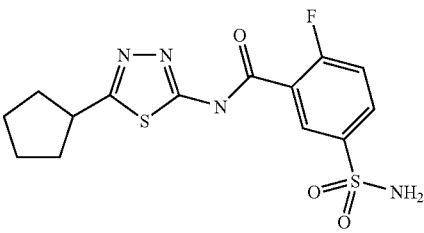

To a 20 ml scintillation vial was added 3-{[(5-cyclopentyl-1,3,4-thiadiazol-2-yl)amino]carbonyl}-4-fluorobenzene-sulfonyl chloride (190 mg, 0.488 mmol) in a mixed solvent (DCM/THF=3 mL/1 mL). To this was added 1 ml of 7M NH$_4$OH(NH$_3$ 28-30% w/w) . The reaction mixture was stirred vigorously at room temperature for two hours. After consumption of the starting material, the reaction solution was concentrated with a rotary evaporator. The product was dissolved with 1.0 mL of DMSO, was purified by using a Gilson preparative HPLC system with a Waters Xterra (C-18) column 100 mm by 50 mm ID, eluting with 1% B to 99% B in 8.5 min, where A=H$_2$O and B=CH$_3$CN pumped at 150 mL/min to yield 5-(aminosulfonyl)-N-(5-cyclopentyl-1,3,4-thiadiazol-2-yl)-2-fluorobenzamide (amount 33 mg, 18.2%). MS (ESI): 371.0 [M+H]+, Rt 0.92 min.

EXAMPLE 9

N-[5-(1,1-dimethylethyl)-1,3,4-thiadiazol-2-yl]-5-[(ethylamino)sulfonyl]-2-iodobenzamide

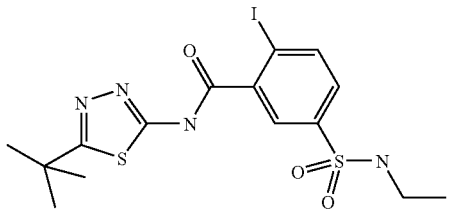

Intermediate 14

N-[5-(1,1-dimethylethyl)-1,3,4-thiadiazol-2-yl]-2-iodobenzamide

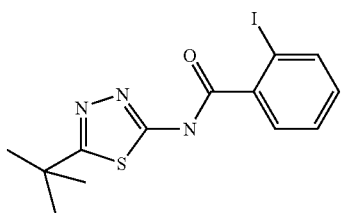

2-Iodobenzoic acid (2 mmol), EDC (2 mmol), and HOBt (4 mmol) were added to 6 ml DCM and stirred at rt for 1 hour. 5-(1,1-dimethylethyl)-1,3,4-thiadiazol-2-amine (2 mmol) was added as a solution in 4 ml DMF. The reaction was stirred at rt for 1 hour and then diluted with ethyl acetate. The solution was washed with 1N HCl, sat. sodium bicarbonate, and brine. The organic layer was dried over sodium sulfate and then evaporated to give N-[5-(1,1-dimethylethyl)-1,3,4-thiadiazol-2-yl]-2-iodobenzamide (750 mg) pure by LCMS. MS (ESI): 388 [M+H]+.

N-[5-(1,1-dimethylethyl)-1,3,4-thiadiazol-2-yl]-5-[(ethylamino)sulfonyl]-2-iodobenzamide

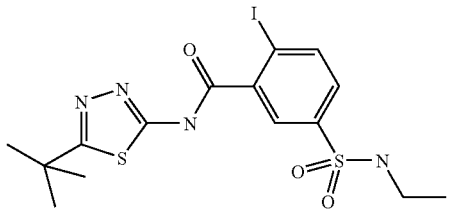

N-[5-(1,1-dimethylethyl)-1,3,4-thiadiazol-2-yl]-2-iodobenzamide (600 mg) was added to 2 ml chlorosulfonic acid and heated at 180 C in a microwave for 1 min. The reaction was cooled to rt and added dropwise to ice water. A solid resulted, was filtered off, and was vacuum dried to give 450 mg of crude 3-({[5-(1,1-dimethylethyl)-1,3,4-thiadiazol-2-yl]amino}carbonyl)-4-iodobenzenesulfonyl chloride which was add to 5 ml of a 2M ethyl amine solution in THF. The reaction was stirred at it for 15 min and then washed with water and evaporated to give 280 mg crude product. 50 mg of this solid was purified by HPLC to give 36 mg N-[5-(1,1-dimethylethyl)-1,3,4-thiadiazol-2-yl]-5-[(ethylamino)sulfonyl]-2-iodobenzamide which was pure by LCMS.

MS (ESI): 495 [M+H]+.

EXAMPLE 10

3-chloro-5-[(ethylamino)sulfonyl]-2,4-difluoro-N-[5-(1-methyl-1-phenylethyl)-1,3,4-thiadiazol-2-yl]benzamide

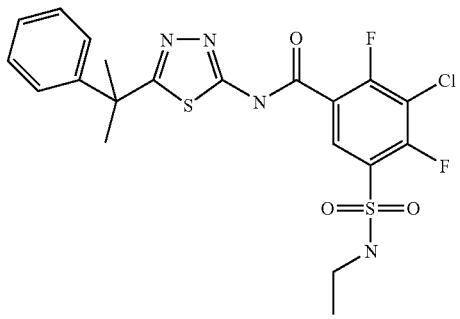

Intermediate 15

3-chloro-5-[(ethylamino)sulfonyl]-2,4-difluorobenzoic acid

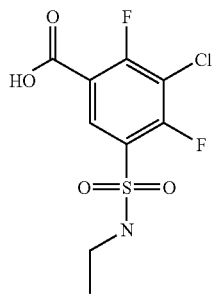

3-chloro-2,4-difluorobenzoic acid (200 mg) in chlorosulfonic acid (1.5 ml, 22.92 mmol) was stirred at room temperature for 30 seconds, then microwaved at 200 degrees for 10 mins. The reaction mixture was cooled to room temperature and dumped on ice (8 g) slowly. Ethyl acetate (50 ml) was added and extracted twice with ethyl acetate (10 mL X2). The combined organic phase was dried over MgSO4. Ethylamine (2.5 ml) in THF (2.0 M) was added, stirred at room temperature for 10 mins and washed with 1 N HCl (10 ml). The organic phase was dried over MgSO4 and concentrated to give crude 3-chloro-5-[(ethylamino)sulfonyl]-2,4-difluorobenzoic acid, which was carried to the next step without further purification.

3-chloro-5-[(ethylamino)sulfonyl]-2,4-difluoro-N-[5-(1-methyl-1-phenylethyl)-1,3,4-thiadiazol-2-yl]benzamide

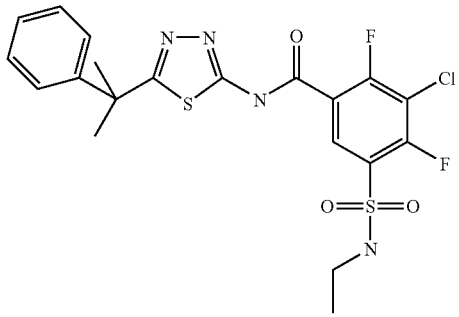

The crude 3-chloro-5-[(ethylamino)sulfonyl]-2,4-difluorobenzoic acid was split into three parts and dissolved in DMF (4 ml) and DCM (4 ml). EDC (81 mg) and HOBt (57 mg) were added to reaction mixture with 5-(1-methyl-1-phenylethyl)-1,3,4-thiadiazol-2-amine (70 mg). The reaction mixture was stirred at room temperature overnight, concentrated to get rid of DCM and purified by Gilson preparative HPLC system with a Water Xterra (C-18) column, eluting with 20% to 80% CH$_3$CN in H$_2$O with TFA (0.1%) to give the title compound (10 mg).

LC/MS: m/z 501.3 (M+H), Rt 2.22 min.

EXAMPLE 11

3-chloro-N-[5-(1,1-dimethylethyl)-1,3,4-thiadiazol-2-yl]-5-[(ethylamino)sulfonyl]-2,4-difluorobenzamide

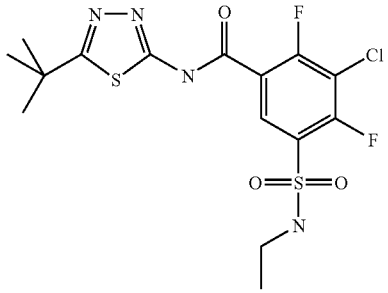

The crude 3-chloro-5-[(ethylamino)sulfonyl]-2,4-difluorobenzoic acid was split into three parts and dissolved in DMF(4 ml) and DCM (4 ml). EDC (81 mg) and HOBt (57 mg) were added to reaction mixture with 5-(1,1-dimethylethyl)-1,3,4-thiadiazol-2-amine (70 mg). The reaction mixture was stirred at room temperature overnight, concentrated to remove DCM and purified by Gilson preparative HPLC system with a Water Xterra (C-18) column, eluting with 20% to 80% CH$_3$CN in H$_2$O with TFA (0.1%) to give the title compound (10 mg).

LC/MS: m/z 439.0 (M+H), rt 2.02 min.

EXAMPLE 12

3-chloro-5-[(ethylamino)sulfonyl]-2,4-difluoro-N-[5-(4-fluorophenyl)-1,3,4-thiadiazol-2-yl]benzamide

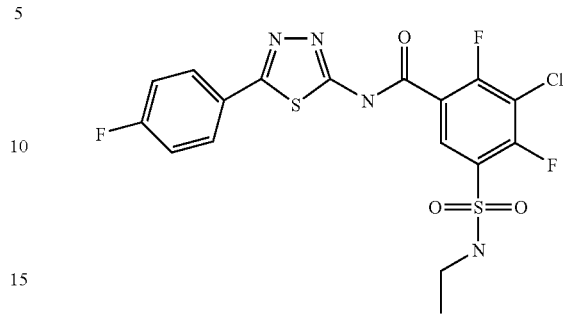

The crude 3-chloro-5-[(ethylamino)sulfonyl]-2,4-difluorobenzoic acid was split into three parts and dissolved in DMF(4 ml) and DCM (4 ml). EDC (81 mg) and HOBt (57 mg) were added to reaction mixture with 5-(4-fluorophenyl)-1,3,4-thiadiazol-2-amine (70 mg). The reaction mixture was stirred at room temperature overnight, concentrated to remove DCM and purified by Gilson preparative HPLC system with a Water Xterra (C-18) column, eluting with 20% to 80% CH$_3$CN in H$_2$O with TFA (0.1%) to give the title compound (10 mg).

LC/MS: m/z 476.9 (M+H), rt 2.15 min.

EXAMPLE 13

5-[(ethylamino)sulfonyl]-2,3,4-trifluoro-N-[5-(1-methyl-1-phenylethyl)-1,3,4-thiadiazol-2-yl]benzamide

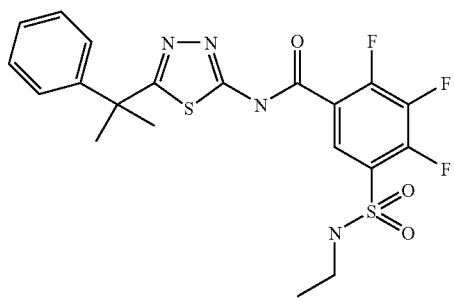

Intermediate 16

5-[(ethylamino)sulfonyl]-2,3,4-trifluorobenzoic acid

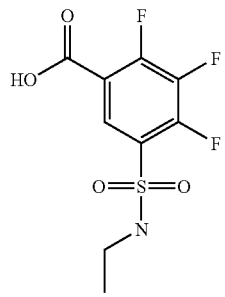

2,3,4-trifluorobenzoic acid (210 mg) in chlorosulfonic acid (1.5 ml, 22.92 mmol) was stirred at room temperature for 30 seconds, then microwave 200° C. for 10 min. The reaction mixture was cooled to room temperature and dumped on ice (10 g) slowly. Ethyl acetate (50 ml) was added and extracted twice with ethyl acetate (10 mL X2). The combined organic phase was dried over MgSO₄. Ethylamine (1.8 ml) in THF (2.0 M) was added, stirred at room temperature for 10 min and washed with 1 N HCl (10 ml). The organic phase was dried over MgSO₄ and concentrated to give crude 5-[(ethylamino) sulfonyl]-2,3,4-trifluorobenzoic acid, which was carried to the next step without further purification.

5-[(ethylamino)sulfonyl]-2,3,4-trifluoro-N-[5-(1-methyl-1-phenylethyl)-1,3,4-thiadiazol-2-yl]benzamide

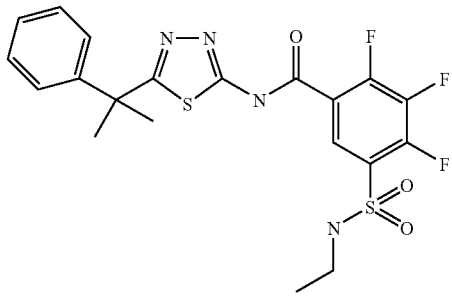

The crude 5-[(ethylamino)sulfonyl]-2,3,4-trifluorobenzoic acid was split into two parts and dissolved in DMF(2.5 ml) and DCM (3 ml). EDC (81 mg) and HOBt (57 mg) were added to reaction mixture with 5-(1-methyl-1-phenylethyl)-1,3,4-thiadiazol-2-amine (93 mg). The reaction mixture was stirred at room temperature overnight, concentrated to remove DCM and purified by Gilson preparative HPLC system with a Water Xterra (C-18) column, eluting with 20% to 80% CH₃CN in H₂O with TFA (0.1%) to give the title compound (15 mg).

LC/MS: m/z 485.0 (M+H), rt 2.14 min.

EXAMPLE 14

3-chloro-5-[(ethylamino)sulfonyl]-2-fluoro-N-[5-(1-methyl-1-phenylethyl)-1,3,4-thiadiazol-2-yl]benzamide

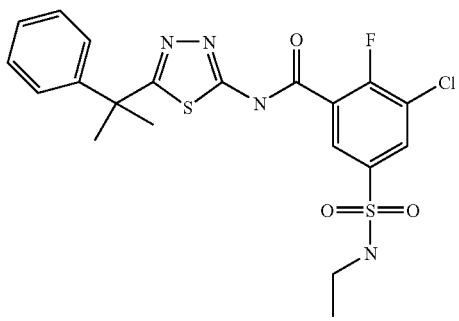

Intermediate 17

3-chloro-5-[(ethylamino)sulfonyl]-2-fluorobenzoic acid

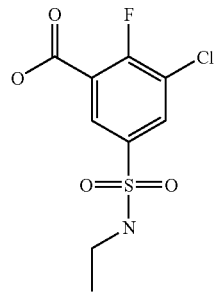

3-chloro-2-fluorobenzoic acid (200 mg, 1.146 mmol) in chlorosulfonic acid (1.535 ml, 22.92 mmol) was stirred at room temperature for 30 seconds, then microwaved at 200 degrees for 10 rains. The reaction mixture was cooled to room temperature and dumped on ice (10 g) slowly. Ethyl acetate (25 ml) was added and extracted twice with ethyl acetate (10 mL X2). The combined organic phase was dried over MgSO₄. Ethylamine (1833 µl, 3.67 mmol) in THF (2.0 M) was added, stirred at room temperature for 10 mins and washed with 1 N HCl (10 ml). The organic phase was dried over MgSO₄ and concentrated to give the title compound, which was carried to the next step without further purification.

3-chloro-5-[(ethylamino)sulfonyl]-2-fluoro-N-[5-(1-methyl-1-phenylethyl)-1,3,4-thiadiazol-2-yl]benzamide

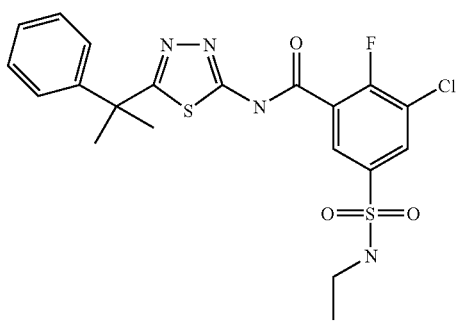

To 3-chloro-5-[(ethylamino)sulfonyl]-2-fluorobenzoic acid (60 mg, 0.213 mmol) in DMF (3 ml) and DCM (3 ml) was added EDC (40.8 mg, 0.213 mmol) and HOBt (32.6 mg, 0.213 mmol). After 10 mins, 5-(1-methyl-1-phenylethyl)-1,3,4-thiadiazol-2-amine (41.6 mg) was added. The reaction mixture was stirred at rt overnight, concentrated and purifed by HPLC to give the title compound (100 mg) LC/MS: m/z 482.8 (M+H), rt 2.05 min.

EXAMPLE 15

3-chloro-N-[3-(1,1-dimethylethyl)-1,3,4-thiadiazol-2-yl]-5-[(ethylamino)sulfonyl]-2-fluorobenzamide

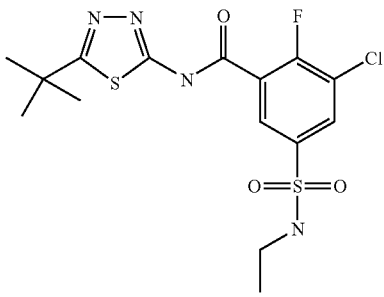

To 3-chloro-5-[(ethylamino)sulfonyl]-2-fluorobenzoic acid (60 mg, 0.213 mmol) in DMF (3 ml) and DCM (3 ml) was added EDC (40.8 mg, 0.213 mmol) and HOBt (32.6 mg, 0.213 mmol). After 10 mins, 5-(1,1-dimethylethyl)-1,3,4-thiadiazol-2-amine (46.7 mg) was added. The reaction mixture was stirred at rt overnight, concentrated and purifed by HPLC to give the title compound (14 mg), C/MS: m/z 421.0 (M+H), Rt 1.91 min.

EXAMPLE 16

N-(5-cyclopentyl-1,3,4-thiadiazol-2-yl)-5-[(ethylamino)sulfonyl]-2,4-difluorobenzamide

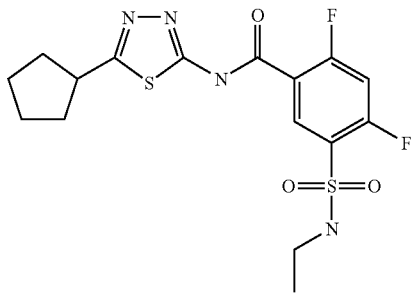

2,4-difluorobenzoic acid (200 mg, 0.765 mmol) in chlorosulfonic acid (1.535 ml, 22.92 mmol) was stirred at room temperature for 30 seconds, then microwave 200 degree for 10 mins. The reaction mixture was cooled to room temperature and dumped on ice (10 g) slowly. Ethyl acetate (25 ml) was added and extracted twice with ethyl acetate (10 mL X2). The combined organic phase was dried over $MgSO_4$. Ethylamine (1833 μl, 3.67 mmol) in THF (2.0 M) was added, stirred at room temperature for 10 mins and washed with 1 N HCl (10 ml). The organic phase was dried over $MgSO_4$ and concentrated to give 5-[(ethylamino)sulfonyl]-2,4-difluorobenzoic acid, which was purified by HPLC 5%-60% $CH_3CN/H_2O$ TFA (0.1%) to give 60 mg. To 5-[(ethylamino)sulfonyl]-2,4-difluorobenzoic acid in N,N-dimethylformamide (3 ml) and dichloromethane (3 ml) was added to EDC (32.5 mg, 0.170 mmol) and HOBt (26.0 mg, 0.170 mmol). After 10 mins, 5-cyclopentyl-1,3,4-thiadiazol-2-amine was added. The reaction mixture was stirred at rt overnight, concentrated and purifed by HPLC. The solvents were removed and purified by HPLC (30-70% with TFA 0.1% $CNCH_3$ and $H_2O$, 18 mins) to give the title compound (5 mg).

LC/MS: m/z 417.2 (M+H), rt 2.14 min.

The intermediates listed in Table 1 were prepared according to General Procedures 1 and 2 and were used without further purification or characterization.

TABLE 1

| Intermediate | Structure | LC/MS [M + H]+/ RT(min) |
|---|---|---|
| 18 | 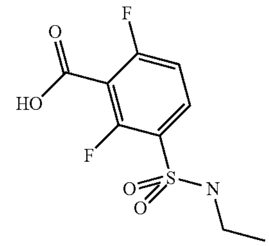 | 265.7/0.94 |
| 19 | 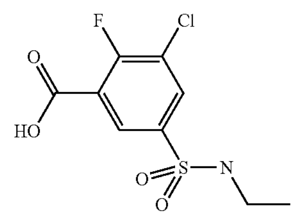 | 282.0/0.67 |
| 20 | 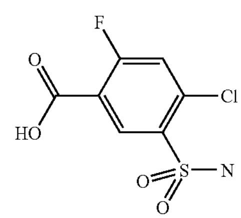 | 253.9 |
| 21 | 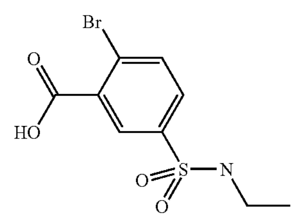 | 309.8/1.29 |
| 22 | 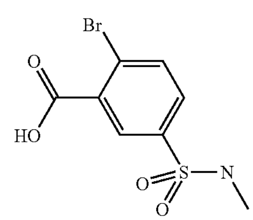 | 293.9 |
| 23 | 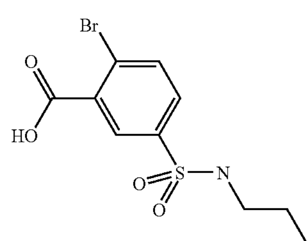 | 321.6/1.48 |

TABLE 1-continued

| Intermediate | Structure | LC/MS [M + H]+/ RT(min) |
|---|---|---|
| 24 | 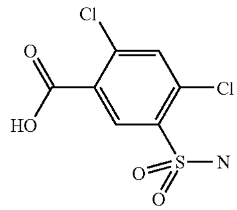 | 269.9 |

General Procedure 10a 2,2,2-trifluoroethanamine (12.57 mmol) and KOH (2.5 N, 3 mL) were added into a round bottom flask and was heated to 40 degree. Then 5-(chlorosulfonyl)-2-fluorobenzoic acid (3.0 g, 12.57 mmol) in toluene and KOH (2.5 N, 21 mL) were added once and the mixture was warmed to 80 degree for 30 min. The reaction was cooled to room temperature and the layers were separated. The organic layer was washed once with aqueous KOH (2.5 N, 7 mL). The combined water layer was put in ice bath and acidified with concentrated HCl (about 8 mL) to PH=1. The reaction was left in the ice bath for 15 to 30 mins until the solid appears. The solid was filtered and aired dry to give solid product, which was carried to the next step without purification.

The intermediates listed in Table 2 were prepared according to General Procedures 1 and 10a from Iintermediate 1:

TABLE 2

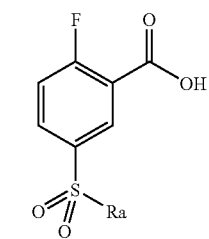

| Intermediate | Ra | LC/MS [M + H]+/ RT (min) |
|---|---|---|
| 25 | 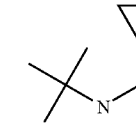 | 301.7/0.68 |
| 26 | 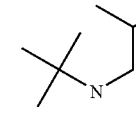 | 273.7/0.70 |

General Procedure 10b

To sulfonyl chloride (10 mmol, 1 eq) in ethyl acetate (25 ml) was added 1-cyclopropyl methenamine (30 mmol, 3 eq). The reaction mixture was stirred at room temperature for 10 mins and washed with 1 N HCl (10 ml). The organic phase was dried over MgSO$_4$ and concentrated to give sulfonamide benzoic acid, which was carried the next step without further purification.

The intermediates listed in Table 3 were prepared according to General Procedure 10b from Intermediate 1:

TABLE 3

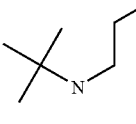

| Intermediate | Ra | LC/MS [M + H]+ |
|---|---|---|
| 27 | 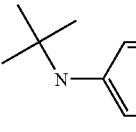 | 274 |
| 28 | 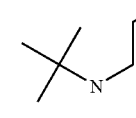 | 276 |
| 29 | 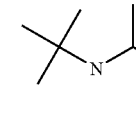 | 276 |
| 30 | 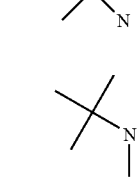 | 296 |
| 31 |  | 262 |
| 32 | 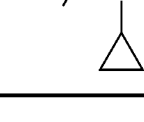 | 262 |
| 34 | | 220 |
| 35 | | 234 |
| 36 | | 260 |

The intermediates listed in Table 4 were prepared according to General Procedure 10b from intermediate 10:

TABLE 4

| Intermediate | Ra | LC/MS [M + H]+ |
|---|---|---|
| 37 | *t*-Bu-N-propyl | 280 |
| 38 | *t*-Bu-N-ethyl | 266 |

The intermediate listed in Table 5 were prepared according to General Procedures 1 and 10b from 2-chloro-3-fluorobenzoic acid:

TABLE 5

| Intermediate | Ra | LC/MS [M]+ |
|---|---|---|
| 39 | *t*-Bu-N-ethyl | 281.9 |

The intermediates listed in Table 6 were prepared according to General Procedures 1 and 10b from 2,3-dichlorobenzoic acid:

TABLE 6

| Intermediate | Ra | LC/MS [M + H]+ |
|---|---|---|
| 40 | *t*-Bu-N-ethyl | 297.9 |
| 41 | *t*-Bu-N | 267.9 |

General Procedure 11

To a T-vial containing 2,2-dimethyl-3-phenylpropanoic acid (0.954 mmol) and hydrazinecarbothioamide (87 mg, 0.954 mmol) was added phosphorus oxychloride (105 μl, 1.145 mmol) dropwise at room temperature. The mixture was heated to 100° C., kept for 2 hrs and cooled to room temperature. Then ethyl acetate and aq. saturated NaHCO₃ was added and the mixture was extracted with ethyl acetate twice, the combined the organic layers were dried with MgSO₄. After filtration, the solvent was removed in vacuo to give the product, which is used directly in the next step.

The following compounds (Table 7) were prepared according to general procedure 11 from the corresponding commercially available carboxylic acids.

TABLE 7

| Intermediate | structure | [M + H]+/ Rt (min) |
|---|---|---|
| 42 | 5-(1-benzyl-1-methyl-ethyl)-1,3,4-thiadiazol-2-amine | 233.7/1.45 |
| 43 | 5-[1-(4-fluorophenyl)cyclopentyl]-1,3,4-thiadiazol-2-amine | 263.7/1.61 |
| 44 | 5-(1-phenylcyclopentyl)-1,3,4-thiadiazol-2-amine | 246.0/1.61 |
| 45 | 5-(1-phenylcyclopropyl)-1,3,4-thiadiazol-2-amine | 218.0/1.36 |
| 46 | 5-[1-(4-fluorophenyl)-1-methyl-ethyl]-1,3,4-thiadiazol-2-amine | 263.7/1.61 |
| 47 | 5-(1-methylcyclohexyl)-1,3,4-thiadiazol-2-amine | 237.6/1.46 |

TABLE 7-continued

| Intermediate | structure | [M + H]+/Rt (min) |
|---|---|---|
| 48 | cyclopentyl-thiadiazole-NH2 | 197.8/1.41 |
| 49 | 1-methylcyclopentyl-thiadiazole-NH2 | 169.8/0.88 |
| 50 | 4,4-difluorocyclohexyl-thiadiazole-NH2 | 183.7/0.82 |
| 51 | 2-(2-fluorophenyl)propan-2-yl-thiadiazole-NH2 | 220.0/0.55 |
| 52 | 2-(4-bromophenyl)propan-2-yl-thiadiazole-NH2 | 297.0/1.64 |
| 53 | 2-fluoro-4-(trifluoromethyl)phenyl-thiadiazole-NH2 | 263.7/1.59 |
| 54 | 2-chloro-4-fluorophenyl-thiadiazole-NH2 | 229.9/1.52 |
| 55 | 2-methylfuran-3-yl-thiadiazole-NH2 | 181.7/0.54 |
| 56 | 1-(trifluoromethyl)cyclopentyl-thiadiazole-NH2 | 237.6/0/77 |
| 57 | 3-methylthiophen-2-yl-thiadiazole-NH2 | 197.7/0.64 |
| 58 | 2,5-dimethylfuran-3-yl-thiadiazole-NH2 | 195.8/1.20 |
| 59 | 2,3,4,5-tetrafluorophenyl-thiadiazole-NH2 | 249.8/1.50 |
| 60 | cyclobutyl-thiadiazole-NH2 | 155.7/0.40 |

5-(1-phenylcyclobutyl)-1,3,4-thiadiazol-2-amine (intermediate 62) (General Procedure 12)

To a round bottom flask containing NaH (2.5 eq) in DMF (10 mL) at zero degree was added a mixture of phenylacetonitrile (1 eq) and 1,3-dibromopropane (1 eq) in DMF (10 mL) dropwise. Then the mixture was warmed up gradually to rt. The reaction was left for 2 hrs. Then toluene and water were added, extracted with toluene twice, combined the organic layers, dried with MgSO4 and filtered and concentrated to give the desired crude product used directly in the next step.

To a round bottom flask containing phenyl cyclobutanecarbonitrile (1 eq) in ethyleneglycol (4 ml) was added KOH (6 eq) at rt. Then the mixture was heated to 160° C. for 2 hrs and cooled to rt. Toluene and water were added and separated the layers. The water layer was acidified to pH ~4, the water layer extracted with ethyl acetate twice, the organic layers combined, dried with MgSO4, filtered and concentrated to give the desired crude product which is used directly in the next step.

Method A:

To a T-vial containing carboxylic acid (1 eq) and hydrazinecarbothioamide (1 eq) was added phosphorus oxychloride (1.2 eq) dropwise at room temperature. The mixture was heated to 100° C., kept for 2 hrs and cooled to room temperature. Ethyl acetate and aq. saturated NaHCO₃ were added, extract with ethyl acetate twice, combined the organic layers, dried with MgSO₄, and concentrate to give the desired product, which is used directly in the next step.

Method B:

To a T-vial containing 1-[3-(trifluoromethyl)phenyl]cyclobutanecarbonitrile (1 eq) and hydrazinecarbothioamide (1 eq) was added TFA (1 eq) dropwise at rt. Then the mixture was heated to 60° C. for 2 hrs and cooled to rt. Ethyl acetate and aq. NaHCO₃ were added and extracted with ethyl acetate twice, the organic layers combined, dried with MgSO₄, and concentrated to give the desired product which was used directly in the next step.

The intermediates were prepared according to General Procedure 12:

TABLE 8

| Intermediate | Rb | LC/MS [M + H]⁺/ Rt (min) | Method |
|---|---|---|---|
| 62 | | 249.9/0.78 | 1-(3-fluorophenyl) cyclobutanecarboxylic acid is commercially available |
| 64 | | 231.9/0.75 | Method A |
| 65 | | 249.9/0.79 | 1-(4-fluorophenyl) cyclobutanecarboxylic acid is commercially available |
| 66 | | 299.9/0.90 | Method B |
| 67 | | 265.9/1.68 | 2-(4-chlorophenyl)-2-ethylbutanoic acid is commercially available |
| 68 | | 237.6/0.71 | Method A |
| 69 | | 299.9/0.92 | Method A |

TABLE 8-continued

| Intermediate | Rb | LC/MS [M + H]+/ Rt (min) | Method |
|---|---|---|---|
| 70 | 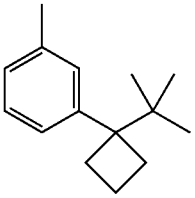 | 246.0/0.88 | Method A |
| 71 |  | 267.6/0.91 | Method B |

The examples listed in Table 9 were prepared by amide formation of the appropriate 5-substituted 1,3,4-thiadiazole-2-amines, selected from intermediates 3, 4, 7, 42-61 or the commercially available 5-(4-fluorophenyl)-2-amino-1,3,4-thiadiazole or 5-t-butyl-2-amino-1,3,4thiadiazole, and the appropriate benzoic acids selected from intermediates 2,9,11, 15-41 using General Procedure 4:

TABLE 9

| Example | Structure | Name | LC/MS [M + H]+ (RT, min) |
|---|---|---|---|
| 17 | 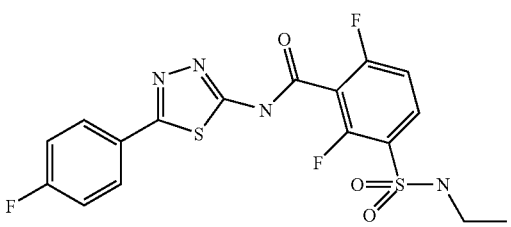 | 3-[(ethylamino)sulfonyl]-2,6-difluoro-N-[5-(4-fluorophenyl)-1,3,4-thiadiazol-2-yl]benzamide | 442.8 (2.03) |
| 18 | 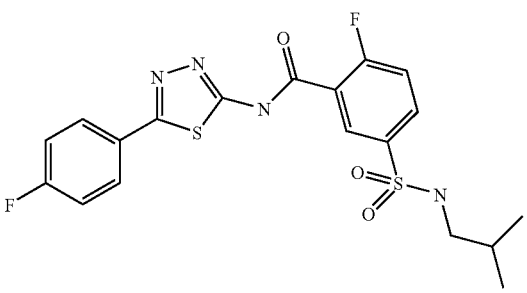 | 2-fluoro-N-[5-(4-fluorophenyl)-1,3,4-thiadiazol-2-yl]-5-{[(2-methylpropyl)amino]sulfonyl}benzamide | 452.8 (2.23) |
| 19 | 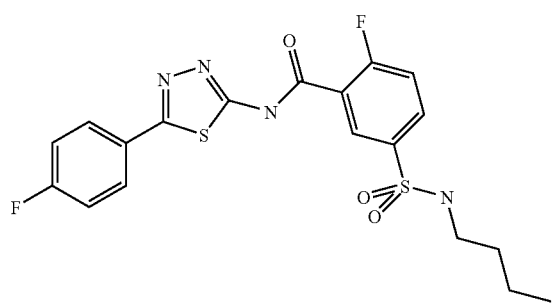 | 5-[(butylamino)sulfonyl]-2-fluoro-N-[5-(4-fluorophenyl)-1,3,4-thiadiazol-2-yl]benzamide | 452.9 (2.24) |

TABLE 9-continued

| Example | Structure | Name | LC/MS [M + H]+ (RT, min) |
|---|---|---|---|
| 20 | 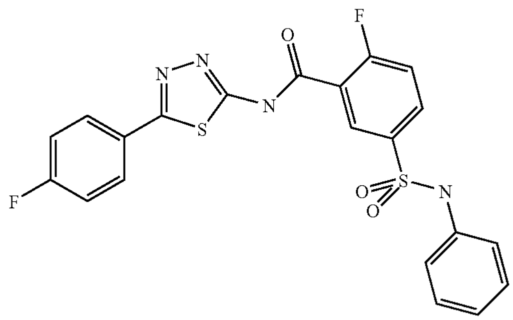 | 2-fluoro-N-[5-(4-fluorophenyl)-1,3,4-thiadiazol-2-yl]-5-[(phenylamino)sulfonyl]benzamide | 472.8 (2.22) |
| 21 | 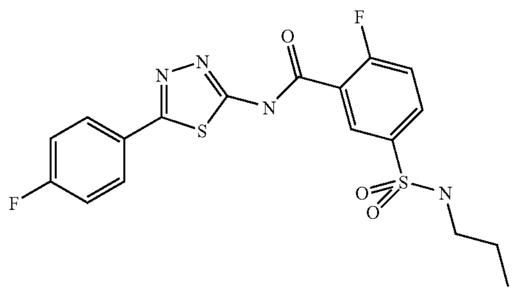 | 2-fluoro-N-[5-(4-fluorophenyl)-1,3,4-thiadiazol-2-yl]-5-[(propylamino)sulfonyl]benzamide | 438.8 (2.12) |
| 22 | 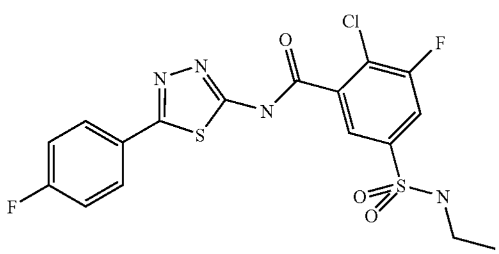 | 2-chloro-5-[(ethylamino)sulfonyl]-3-fluoro-N-[5-(4-fluorophenyl)-1,3,4-thiadiazol-2-yl]-benzamide | 458.8 (2.08) |
| 23 | 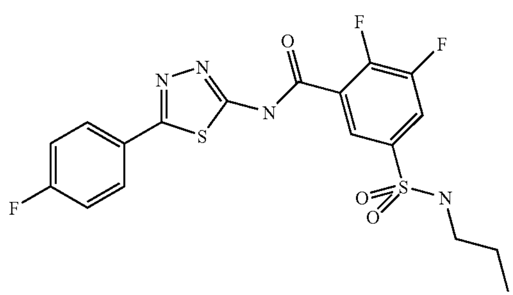 | 2,3-difluoro-N-[5-(4-fluorophenyl)-1,3,4-thiadiazol-2-yl]-5-[(propylamino)sulfonyl]-benzamide | 457.1 (2.14) |
| 24 | 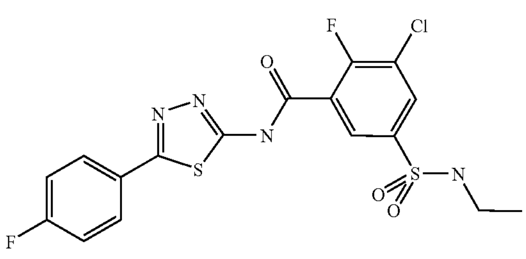 | 3-chloro-5-[(ethylamino)sulfonyl]-2-fluoro-N-[5-(4-fluorophenyl)-1,3,4-thiadiazol-2-yl]-benzamide | 459.1 (2.17) |

TABLE 9-continued

| Example | Structure | Name | LC/MS [M + H]+ (RT, min) |
|---------|-----------|------|--------------------------|
| 25 | 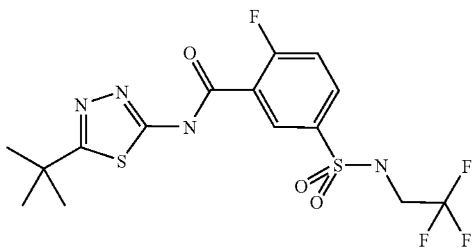 | N-[5-(1,1-dimethylethyl)-1,3,4-thiadiazol-2-yl]-2-fluoro-5-{[(2,2,2-trifluoroethyl)amino]sulfonyl}benzamide | 441.0 (1.9) |
| 26 | 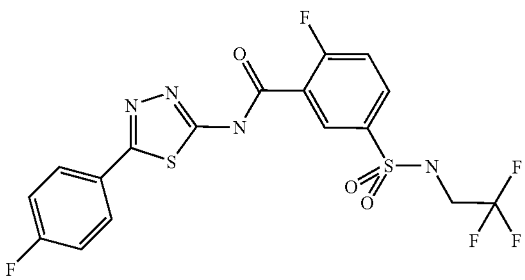 | 2-fluoro-N-[5-(4-fluorophenyl)-1,3,4-thiadiazol-2-yl]-5-{[(2,2,2-trifluoroethyl)amino]sulfonyl}benzamide | 478.9 (2.04) |
| 27 | 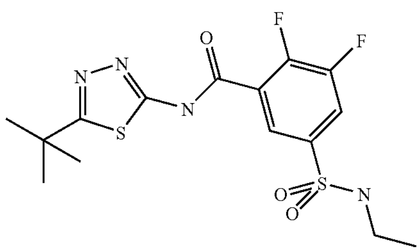 | N-[5-(1,1-dimethylethyl)-1,3,4-thiadiazol-2-yl]-5-[(ethylamino)sulfonyl]-2,3-difluorobenzamide | 405.0 (1.92) |
| 28 | 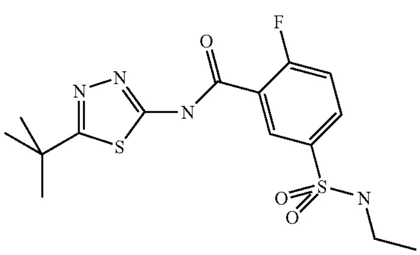 | N-[5-(1,1-dimethylethyl)-1,3,4-thiadiazol-2-yl]-5-[(ethylamino)sulfonyl]-2-fluorobenzamide | 386..8 (1.81) |
| 29 | 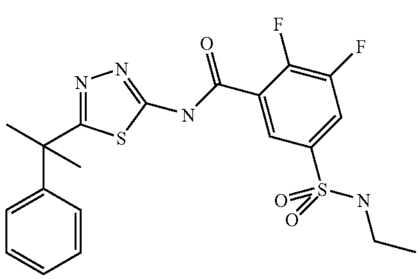 | 5-[(ethylamino)sulfonyl]-2,3-difluoro-N-[5-(1-methyl-1-phenylethyl)-1,3,4-thiadiazol-2-yl]benzamide | 467.0 (2.17) |
| 30 | 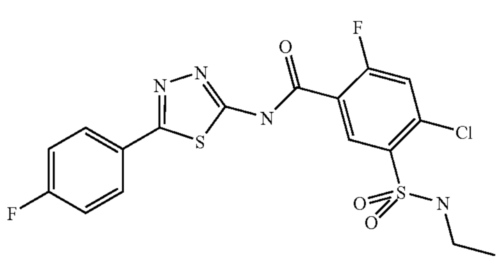 | 5-(aminosulfonyl)-4-chloro-2-fluoro-N-[5-(4-fluorophenyl)-1,3,4-thiadiazol-2-yl]-benzamide | 430.8 (1.88) |

TABLE 9-continued

| Example | Name | LC/MS [M + H]+ (RT, min) |
|---|---|---|
| 31 | 2,3-dichloro-5-[(ethylamino)sulfonyl]-N-[5-(1-methyl-1-phenylethyl)-1,3,4-thiadiazol-2-yl]-benzamide | 499.0 (2.3) |
| 32 | 2,3-dichloro-N-[5-(1,1-dimethylethyl)-1,3,4-thiadiazol-2-yl]-5-[(ethylamino)sulfonyl]-benzamide | 437.0 (2.09) |
| 33 | 2,3-dichloro-5-[(ethylamino)sulfonyl]-N-[5-(4-fluorophenyl)-1,3,4-thiadiazol-2-yl]benzamide | 474.9 (2.24) |
| 34 | 2-bromo-5-[(ethylamino)sulfonyl]-N-[5-(4-fluorophenyl)-1,3,4-thiadiazol-2-yl]benzamide | 484.9 (2.07) |
| 35 | 2-bromo-N-[5-(4-fluorophenyl)-1,3,4-thiadiazol-[(propylamino)sulfonyl]benzamide | 500.8 (2.18) |
| 36 | 5-(aminosulfonyl)-2,3-dichloro-N-[5-(1-methyl-1-phenylethyl)-1,3,4-thiadiazol-2-yl]benzamide | 471.2 (2.14) |

TABLE 9-continued

| Example | Structure | Name | LC/MS [M + H]+ (RT, min) |
|---|---|---|---|
| 37 | 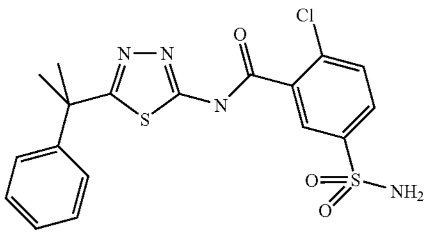 | 5-(aminosulfonyl)-2-chloro-N-[5-(1-methyl-1-phenylethyl) 1,3,4-thiadiazol-2-yl]-benzamide | 436.8 (1.92) |
| 38 | 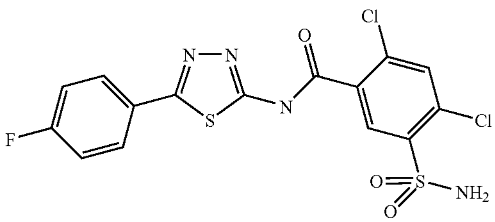 | 5-(aminosulfonyl)-2,4-dichloro-N-[5-(4-fluorophenyl)-1,3,4-thiadiazol-2-yl]benzamide | 446.8 (1.95) |
| 39 | 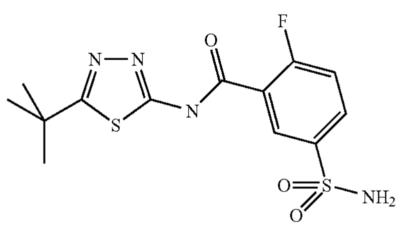 | 5-(aminosulfonyl)-N-[5-(1,1-dimethylethyl)-1,3,4-thiadiazol-2-yl]-2-fluorobenzamide | 358.8 (1.57) |
| 40 | 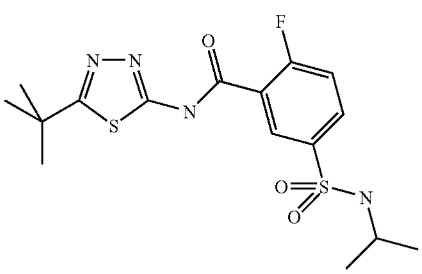 | N-[5-(1,1-dimethylethyl) 1,3,4-thiadiazol-2-yl]-2-fluoro-5-{[(1-methylethyl)amino]sulfonyl}-benzamide | 400.8 (1.91) |
| 41 | 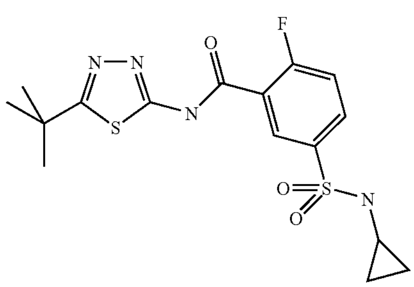 | 5-[(cyclopropylamino)sulfonyl] N-[5-(1,1-dimethylethyl)-1,3,4-thiadiazol-2-yl]-2-fluorobenzamide | 398.8 (1.88) |
| 42 | 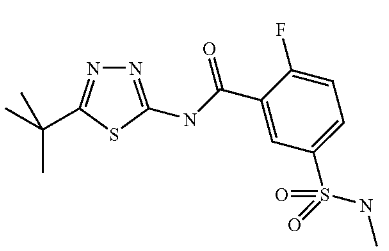 | N-[5-(1,1-dimethylethyl) 1,3,4-thiadiazol-2-yl]-2-fluoro-5-[(methylamino)sulfonyl]-benzamide | 372.8 (1.73) |

TABLE 9-continued

| Example | Structure | Name | LC/MS [M + H]+ (RT, min) |
|---|---|---|---|
| 43 | 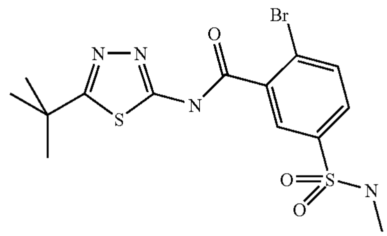 | 2-bromo-N-[5-(1,1-dimethylethyl)-1,3,4-thiadiazol-2-yl]-5-[(methylamino)sulfonyl]benzamide | 433.0 (1.82) |
| 44 | 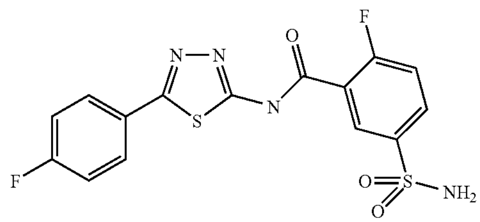 | 5-(aminosulfonyl)-2-fluoro-N-[5-(4-fluorophenyl)-1,3,4-thiadiazol-2-yl]benzamide | 398.2 (1.69) |
| 45 | 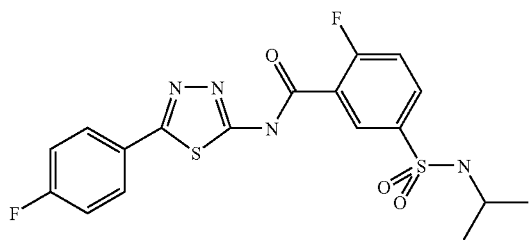 | 2-fluoro-N-[5-(4-fluorophenyl)-1,3,4-thiadiazol-2-yl]-5-{[(1-methylethyl)amino]sulfonyl}-benzamide | 438.8 (2.1) |
| 46 | 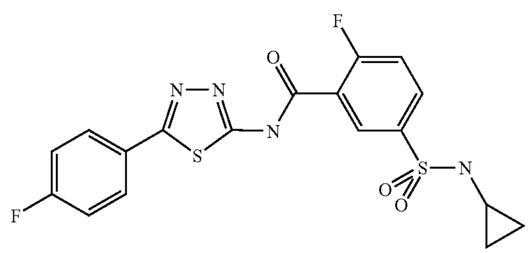 | 5-[(cyclopropylamino)sulfonyl]2-fluoro-N-[5-(4-fluorophenyl)-l-,3,4-thiadiazol-2-yl]benzamide | 437.1 (2.04) |
| 47 | 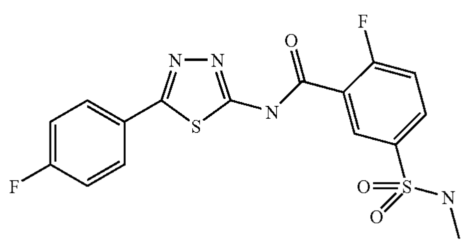 | 2-fluoro-N-[5-(4-fluorophenyl)-1,3,4-thiadiazol-2-yl]-5-[(methylamino)sulfonyl]benzamide | 412.2 (1.87) |
| 48 | 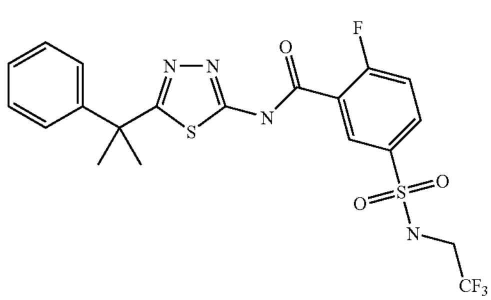 | 2-fluoro-N-[5-(1-methyl-1-phenylethyl)-1,3,4-thiadiazol-trifluoroethyl)amino]sulfonyl}benzamide | 503.0 (2.29) |

TABLE 9-continued

| Example | Structure | Name | LC/MS [M + H]+ (RT, min) |
|---|---|---|---|
| 49 | 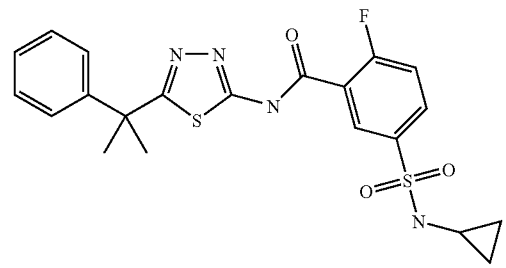 | 5-[(cyclopropylamino)sulfonyl]2-fluoro-N-[5-(1-methyl-1-phenylethyl)-1,3,4-thiadiazol-2-yl]benzamide | 461.3 (2.06) |
| 50 | 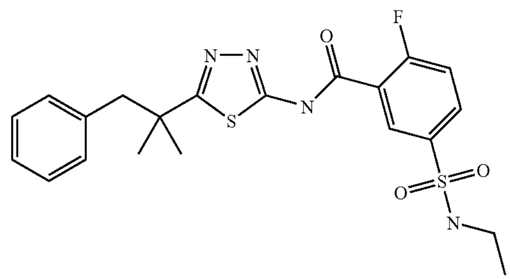 | N-[5-(1,1-dimethyl-2-phenylethyl)-1,3,4-thiadiazol-2-yl]-5-[(ethylamino)sulfonyl]-2-fluorobenzamide | 463.5 (2.23) |
| 51 | 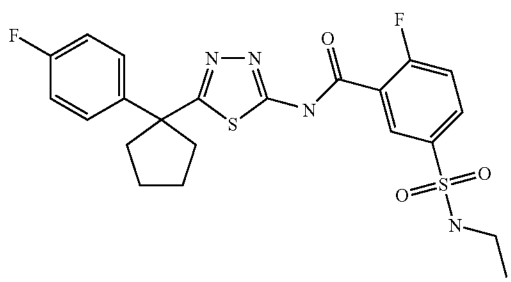 | 5-[(ethylamino)sulfonyl]-2-fluoro-N-{5-[1-(4-fluorophenyl)cyclopentyl]-1,3,4-thiadiazol-2-yl}-benzamide | 493.1 (2.35) |
| 52 | 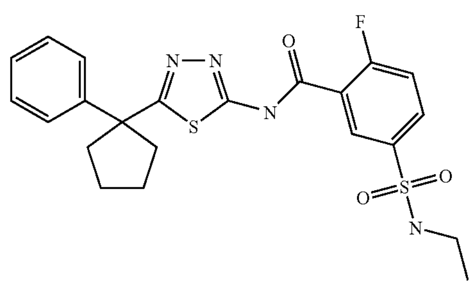 | 5-[(ethylamino)sulfonyl]-2-fluoro-N-[5-(1-phenylcyclopentyl)-1,3,4-thiadiazol-2-yl]benzamide | 475.0 (2.24) |
| 53 | 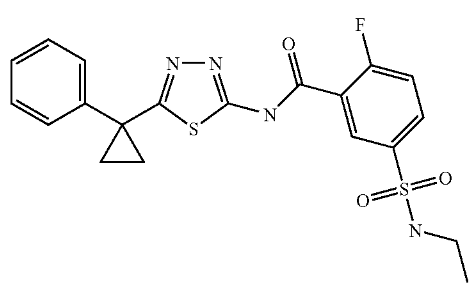 | 5-[(ethylamino)sulfonyl]-2-fluoro-N-[5-(1-phenylcyclopropyl)-1,3,4-thiadiazol-2-yl]benzamide | 447.1 (2.07) |

TABLE 9-continued

| Example | Structure | Name | LC/MS [M + H]+ (RT, min) |
|---|---|---|---|
| 54 | 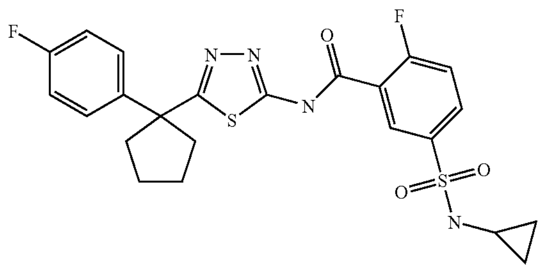 | 5-[(cyclopropylamino)sulfonyl]-2-fluoro-N-{5-[1-(4-fluorophenyl)cyclopentyl]1,3,4-thiadiazol-2-yl}-benzamide | 505.1 (2.39) |
| 55 | 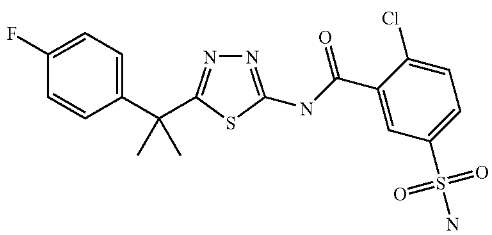 | 5-(aminosulfonyL)-2-chloro-N-{5-[1-(4-fluorophenyl)-1-methylethyl]-1,3,4-thiadiazol-2-yl}benzamide | 455.0 (2.07) |
| 56 | 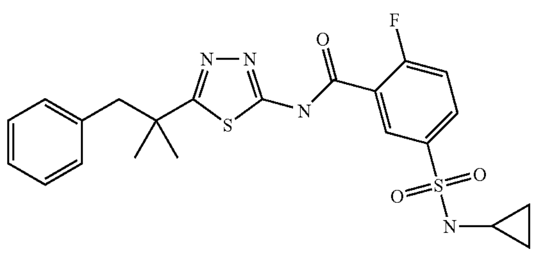 | 5-[(cyclopropylamino)sulfonyl]-N-[5-(1,1-dimethy-2-phenylethyl)-1,3,4-thiadiazol-2-yl]-2-fluorobenzamide | 475.1 (2.28) |
| 57 | 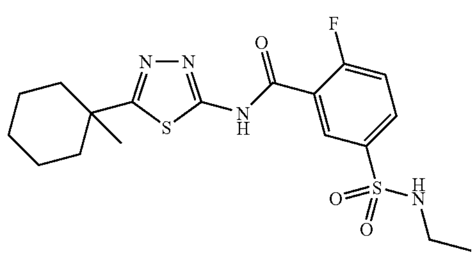 | 5-[(ethylamino)sulfonyl]-2-fluoro-N-[5-(1-methylcyclohexyl)-1,3,4-thiadiazol-2-yl]benzamide | 427.0 (1.45) |
| 58 | 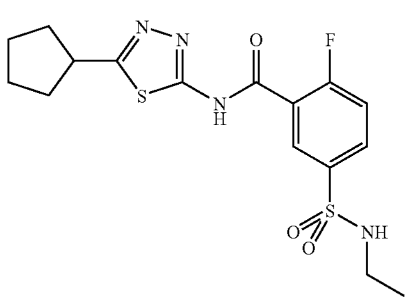 | N-(5-cyclopentyl-1,3,4-thiadiazol-2-yl)-5-[(ethylamino)sulfonyl]-2-fluorobenzamide | 398.8 (0.99) |

TABLE 9-continued

| Example | Structure | Name | LC/MS [M + H]+ (RT, min) |
|---|---|---|---|
| 59 | 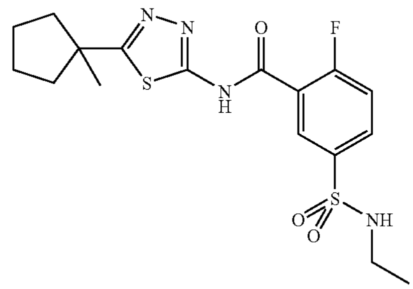 | 5-[(ethylamino)sulfonyl]-2-fluoro-N-[5-(1-methylcyclopentyl)-1,3,4-thiadiazol-2-yl]benzamide | 413.1 (1.05) |
| 60 | 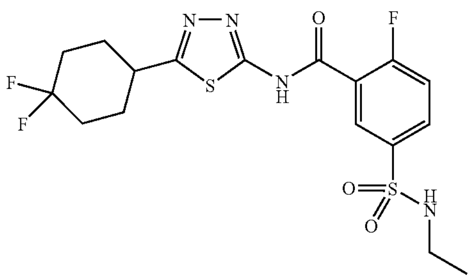 | N-[5-(4,4-difluorocyclohexyl)-1,3,4-thiadiazol-2-yl]-5-[(ethylamino)sulfonyl]-2-fluorobenzamide | 449.2 (1.03) |
| 61 | 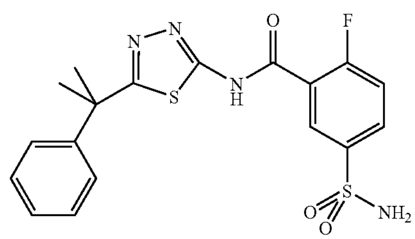 | 5-(aminosulfonyl)-2-fluoro-N-[5-(1-methyl-1-phenylethyl)-1,3,4-thiadiazol-2-yl]-benzamide | 421.2 (1.01) |
| 62 | 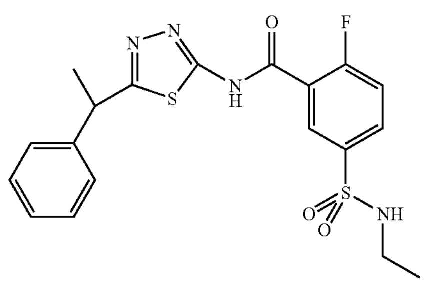 | 5-[(ethylamino)sulfonyl]-2-fluoro-N-[5-(1-phenylethyl)1,3,4-thiadiazol-2-yl]-benzamide | 435.3 (1.06) |
| 63 | 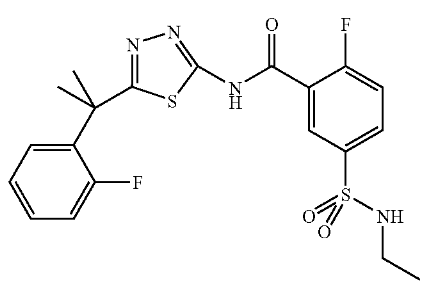 | 5-[(ethylamino)sulfonyl]-2-fluoro-N-{5-[1-(2-fluorophenyl)-1-methylethyl]-1,3,4-thiadiazol-2-yl}-benzamide | 467.2 (1.10) |

TABLE 9-continued

| Example | Structure | Name | LC/MS [M + H]+ (RT, min) |
|---|---|---|---|
| 64 | 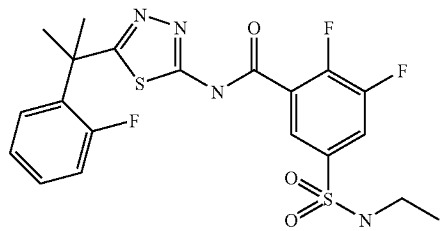 | 5-[(ethylamino)sulfonyl]-2,3-difluoro-N-{5-[1-(2-fluorophenyl)-1-methylethyl]-1,3,4-thiadiazol-2-yl}-benzamide | 484.7 (1.13) |
| 65 | 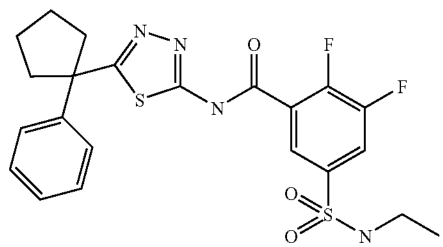 | 5-[(ethylamino)sulfonyl]-2,3-difluoro-N-[5-(1-phenylcyclopentyl)-1,3,4-thiadiazol-2-yl]benzamide | 492.8 (1.27) |
| 66 | 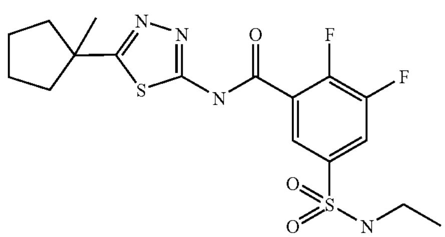 | 5-[(ethylamino)sulfonyl]-2,3-difluoro-N-[5-(1-methylcyclopentyl)-1,3,4-thiadiazol-2-yl]benzamide | 430.8 (1.14) |
| 67 | 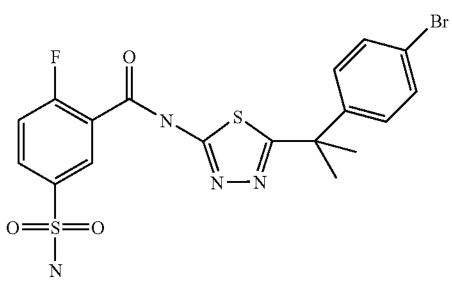 | 5-(aminosulfonyl)-N-{5-[1-(4-bromophenyl)-1-methylethyl]-1,3,4-thiadiazol-2-yl}-2-fluorobenzamide | 498.9, 501.0/ 2.03 |

The examples listed in Table 10 were prepared by amide formation of the appropriate 5-substituted 1,3,4-thiadiazole-2-amines, selected from intermediates 52-71 and the appropriate benzoic acids selected from intermediates 2, 9, 11, 15-41 using General Procedure 4:

TABLE 10

| Example | Structure | Name | LC/MS [M + H]+/ RT |
|---|---|---|---|
| 68 | 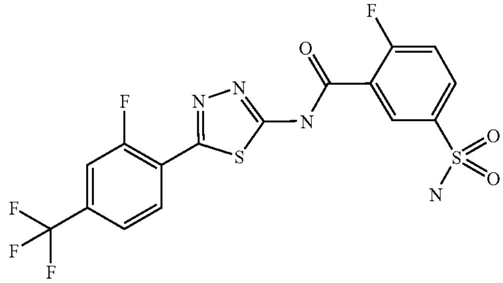 | 5-(aminosulfonyl)-2-fluoro-N-{5-[2-fluoro-4-(trifluoromethyl)phenyl]-1,3,4-thiadiazol-2-yl}benzamide | 465.1/ 1.01 min |

TABLE 10-continued

| Example | Name | LC/MS [M + H]+/ RT |
|---|---|---|
| 69 | 5-(aminosulfonyl)-N-[5-(2-chloro-4-fluorophenyl)-1,3,4-thiadiazol-2-yl]-2-fluorobenzamide | 430.9/ 0.93 min |
| 70 | N-[5-(2-chloro-4-fluorophenyl)-1,3,4-thiadiazol-2-yl]-2-fluoro-5-{[(2,2,2-trifluoroethyl)amino]-sulfonyl}benzamide | 513.1/ 1.12 min |
| 71 | 2-fluoro-N-[5-(2-methyl-3-furanyl)-1,3,4-thiadiazol-2-yl]-5-{[(2,2,2-trifluoroethyl)amino]sulfonyl}benzamide | 465.1/ 0.97 min |
| 72 | 2-fluoro-N-{5-[1-(3-fluorophenyl)-cyclobutyl]-1,3,4-thiadiazol-2-yl}-5-({[(2,2,2-trifluoroethyl)amino]-sulfonyl}benzamide | 533.0/ 1.17 min |
| 73 | 2-fluoro-5-{[(2,2,2-trifluoroethyl)amino]-sulfonyl}-N-{5-[1-(trifluoromethyl)cyclopentyl]-1,3,4-thiadiazol-2-yl}benzamide | 521.1/ 1.15 min |

TABLE 10-continued

| Example | Structure | Name | LC/MS [M + H]+/ RT |
|---|---|---|---|
| 74 | 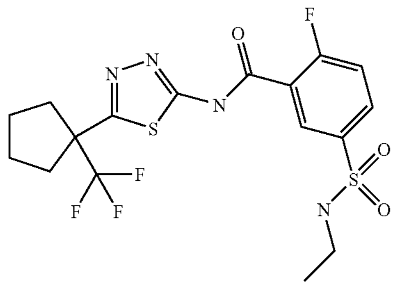 | 5-[(ethylamino)sulfonyl]-2-fluoro-N-{5-[1-(trifluoromethyl)cyclopentyl]-1,3,4-thiadiazol-2-yl}benzamide | 467.8/ 1.08 min |
| 75 | 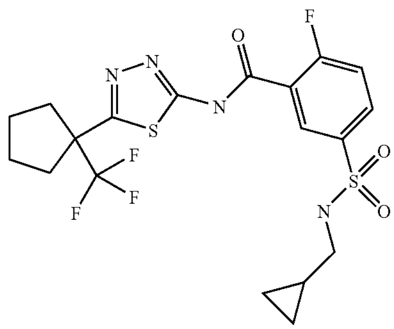 | 5-{[(cyclopropylmethyl)amino]sulfonyl}-2-fluoro-N-{5-[1-(trifluoromethyl)-cyclopentyl]-1,3,4-thiadiazol-2-yl}-benzamide | 493.2/ 1.16 min |
| 76 | 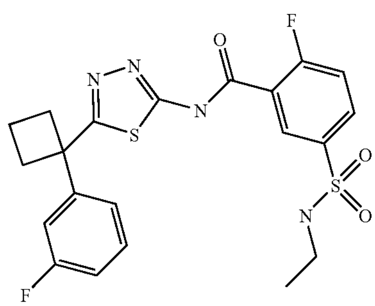 | 5-[(ethylamino)sulfonyl]-2-fluoro-N-{5-[1-(3-fluorophenyl)-cyclobutyl]-1,3,4-thiadiazol-2-yl}-benzamide | 479.0/ 1.10 min |
| 77 | 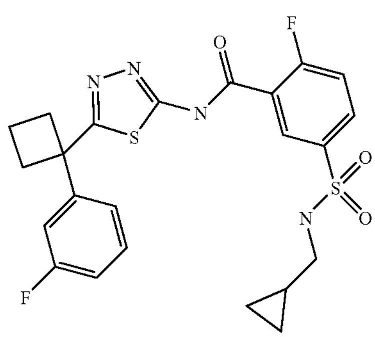 | 5-{[(cyclopropylmethyl)amino]sulfonyl}-2-fluoro-N-{5-[1-(3-fluorophenyl)-cyclobutyl]-1,3,4-thiadiazol-2-yl}-benzamide | 505.2/ 1.16 min |
| 78 | 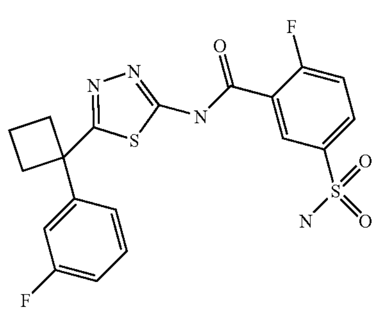 | 5-(aminosulfonyl)-2-fluoro-N-{5-[1-(3-fluorophenyl)-cyclobutyl]-1,3,4-thiadiazol-2-yl}-benzamide | 450.8/ 1.00 min |

TABLE 10-continued

| Example | Structure | Name | LC/MS [M + H]+/ RT |
|---|---|---|---|
| 79 | 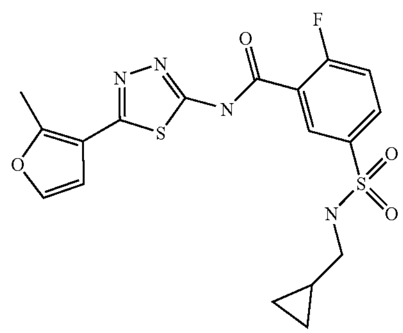 | 5-{[(cyclopropylmethyl)-amino]sulfonyl}-2-fluoro-N-[5-(2-methyl-3-furanyl)-1,3,4-thiadiazol-2-yl]-benzamide | 437.1/ 0.98 min |
| 80 | 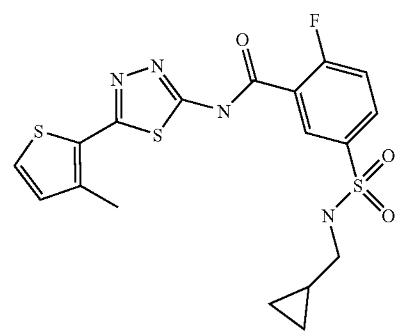 | 5-{[(cyclopropylmethyl)amino]sulfonyl}-2-fluoro-N-[5-(3-methyl-2-thienyl)-1,3,4-thiadiazol-2-yl]-benzamide | 453.0/ 1.02 min |
| 81 | 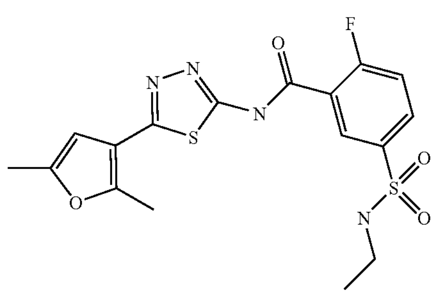 | N-[5-(2,5-dimethyl-3-furanyl)-1,3,4-thiadiazol-2-yl]-5-[(ethylamino)sulfonyl]-2-fluorobenzamide | 425.0/ 0.99 min |
| 82 | 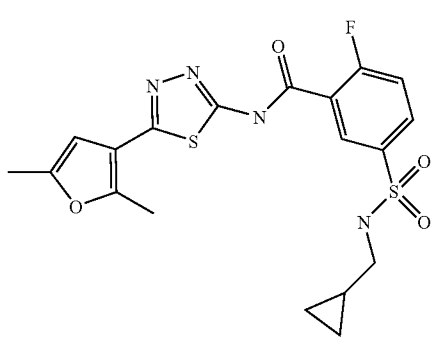 | 5-{[(cyclopropylmethyl)amino]sulfonyl}-N-[5-(2,5-dimethyl-3-furanyl)-1,3,4-thiadiazol-2-yl]-2-fluorobenzamide | 450.8/ 1.06 min |

TABLE 10-continued

| Example | Structure | Name | LC/MS [M + H]+/ RT |
|---|---|---|---|
| 83 | 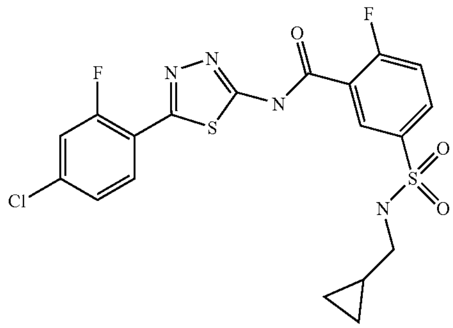 | N-[5-(4-chloro-2-fluorophenyl)-1,3,4-thiadiazol-2-yl]-5-{[(cyclopropylmethyl)-amino]sulfonyl}-2-fluorobenzamide | 485.0/ 2.30 min |
| 84 | 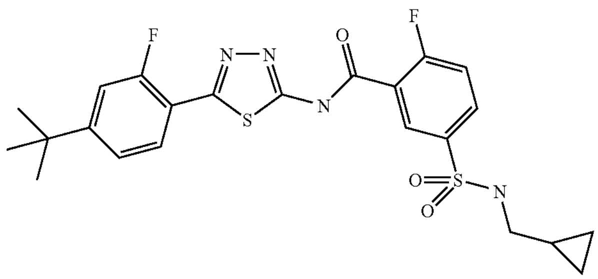 | 5-{[(cyclopropylmethyl)amino]sulfonyl}-2-fluoro-N-{5-[2-fluoro-4-(trifluoromethyl)-phenyl]-1,3,4-thiadiazol-2-yl}-benzamide | 519.2/ 2.53 min |
| 85 | 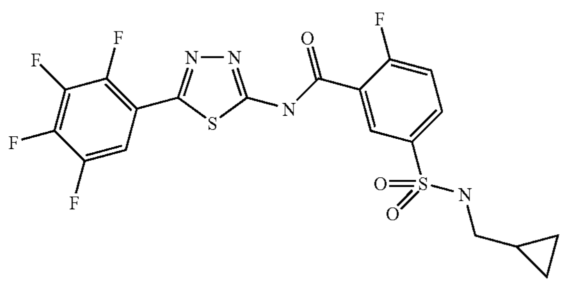 | 5-{[(cyclopropylmethyl)amino]sulfonyl}-2-fluoro-N-[5-(2,3,4,5-tetrafluorophenyl)-1,3,4-thiadiazol-2-yl]-benzamide | 504.9/ 2.31 min |
| 86 | 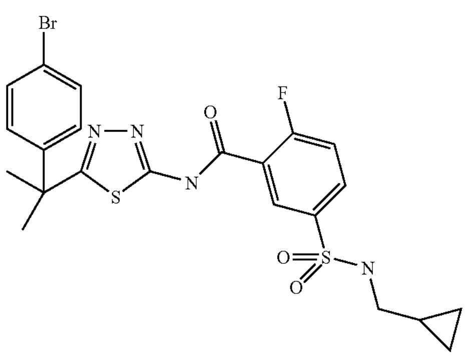 | N-{5-[1-(4-bromophenyl)-1-methylethyl]-1,3,4-thiadiazol-2-yl}-5-{[(cyclopropylmethyl)-amino]sulfonyl}-2-fluorobenzamide | 553.1/ 2.32 min |
| 87 | 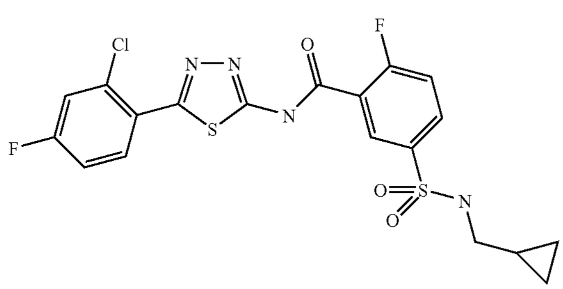 | N-[5-(2-chloro-4-fluorophenyl)-1,3,4-thiadiazol-2-yl]-5-{[(cyclopropylmethyl)-amino]sulfonyl}-2-fluorobenzamide | 484.9/ 2.20 min |

TABLE 10-continued

| Example | Structure | Name | LC/MS [M + H]+/ RT |
|---|---|---|---|
| 88 | 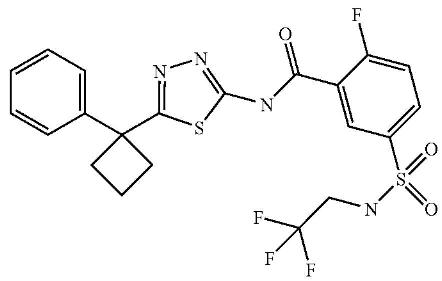 | 2-fluoro-N-[5-(1-phenylcyclobutyl)-1,3,4-thiadiazol-2-yl]-5-{[(2,2,2-trifluoroethyl)amino]sulfonyl}benzamide | 515.2/ 1.16 min |
| 89 | 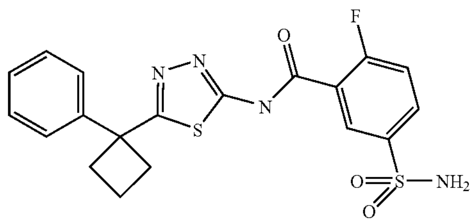 | 5-(aminosulfonyl)-2-fluoro-N-[5-(1-phenylcyclobutyl)-1,3,4-thiadiazol-2-yl]-benzamide | 434.2/ 0.97 min |
| 90 | 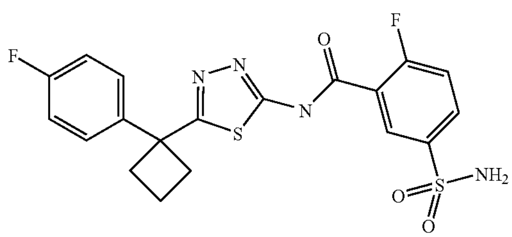 | 5-(aminosulfonyl)-2-fluoro-N-{5-[1-(4-fluorophenyl)cyclobutyl]-1,3,4-thiadiazol-2-yl}-benzamide | 450.8/ 0.97 min |
| 91 | 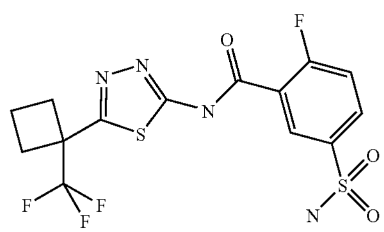 | 5-(aminosulfonyl)-2-fluoroN-{5-[1-(trifluoromethyl)-cyolobutyl]-1,3,4-thiadiazol-2-yl}-benzamide | 424.9/ 0.92 min |
| 92 | 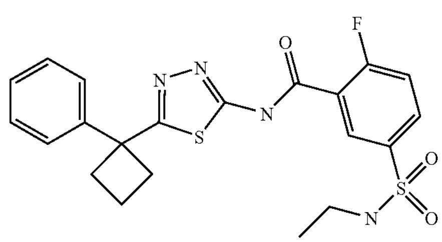 | 5-[(ethylamino)sulfonyl]-2-fluoro-N-[5-(1-phenylcyclobutyl)-1,3,4-thiadiazol-2-yl]-benzamide | 461.1/ 1.09 min |
| 93 | 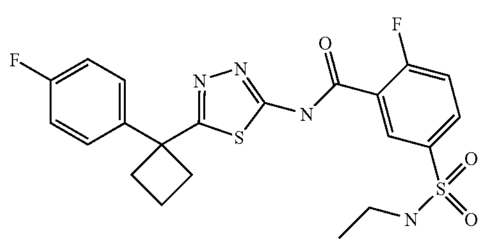 | 5-[(ethylamino)sulfonyl]-2-fluoro-N-{5-[1-(4-fluorophenyl)-cyclobutyl]-1,3,4-thiadiazol-2-yl}benzamide | 479.1/ 1.09 min |

TABLE 10-continued

| Example | Structure | Name | LC/MS [M + H]+/ RT |
|---|---|---|---|
| 94 | 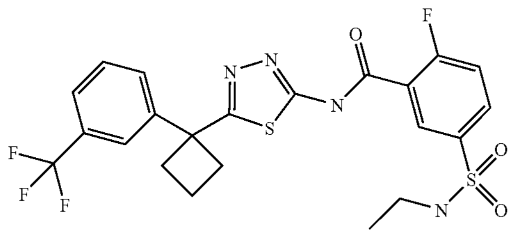 | 5-[(ethylamino)sulfonyl]-2-fluoro-N-(5-{1-[3-(trifluoromethyl)phenyl]cyclobutyl}-1,3,4-thiadiazol-2-yl)-benzamide | 529.1/ 1.21 min |
| 95 | 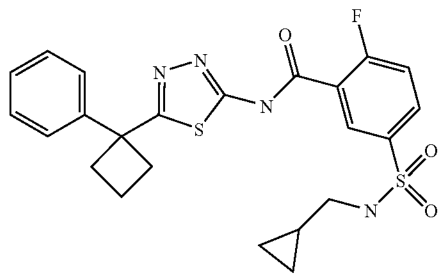 | 5-{[(cyclopropylmethyl)amino]sulfonyl}-2-fluoro-N-[5-(1-phenylcyclobutyl)-1,3,4-thiadiazol-2-yl]-benzamide | 487.4/ 1.16 min |
| 96 | 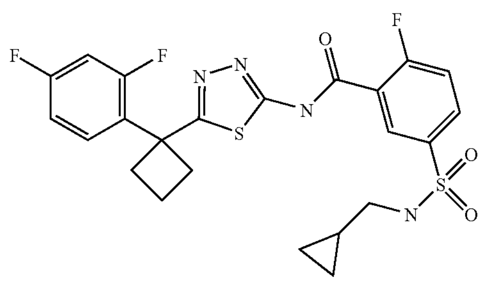 | 5-{[(cyclopropylmethyl)-amino]sulfonyl}-N-{5-[1-(2,4-difluorophenyl)cyclobutyl]-1,3,4-thiadiazol-2-yl}-2-fluorobenzamide | 523.2/ 1.20 min |
| 97 | 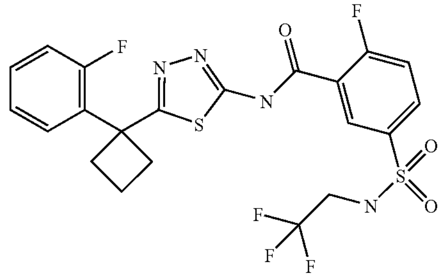 | 2-fluoro-N-{5-[1-(2-fluorophenyl)-cyclobutyl]-1,3,4-thiadiazol-2-yl}-5-{[(2,2,2-trifluoroethyl)amino}benzamide | 533.1/ 1.15 min |
| 98 | 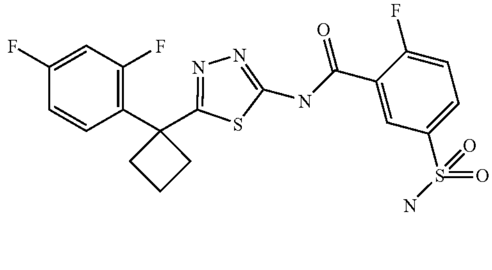 | 5-(aminosulfonyl)-N-{5-[1-(2,4-difluorophenyl)-cyclobutyl]-1,3,4-thiadiazol-2-yl}-2-fluorobenzamide | 469.1/ 1.02 min |

TABLE 10-continued

| Example | Structure | Name | LC/MS [M + H]+/ RT |
|---|---|---|---|
| 99 | 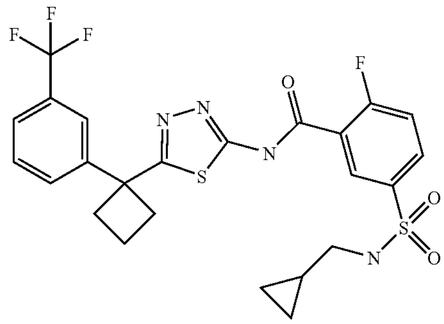 | 5-{[(cyclopropylmethyl)-amino]sulfonyl}-2-fluoro-N-(5-{1-[3-(trifluoromethyl)-phenyl]cyclobutyl}-1,3,4-thiadiazol-2-yl)-benzamide | 555.3/ 1.30 min |
| 100 | 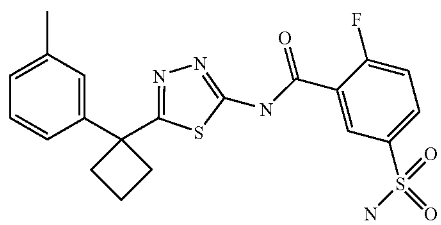 | 5-(aminosulfonyl)-2-fluoro-N-(5-[1-(3-methylphenyl)cyclobutyl]-1,3,4-thiadiazol-2-yl}benzamide | 447.3/ 1.13 min |
| 101 | 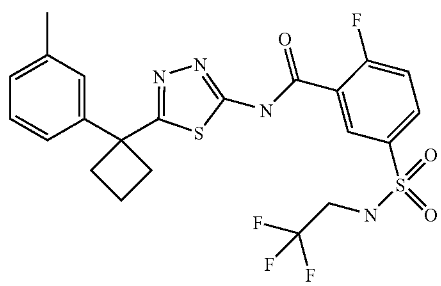 | 2-fluoro-N-{5-[1-(3-methylphenyl)-cyclobutyl]-1,3,4-thiadiazol-2-yl}-5-{[(2,2,2-trifluoroethyl)amino]sulfonyl}benzamide | 529.2/ 1.30 min |
| 102 | 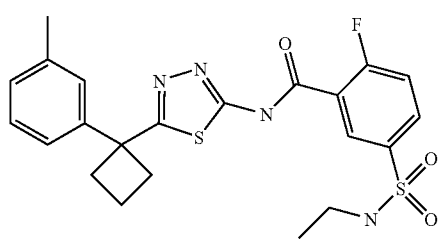 | 5-[(ethylamino)sulfonyl]-2-fluoro-N-{5-[1-(3-methylphenyl)-cyclobutyl]-1,3,4-thiadiazol-2-yl}-benzamide | 475.2/ 1.26 min |
| 103 | 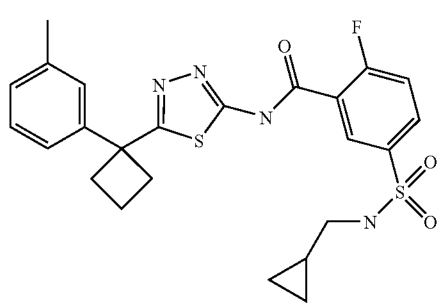 | 5-{[(cyclopropylmethyl)-amino]sulfonyl}-2-fluoro-N-{5-[1-(3-methylphenyl)-cyclobutyl]-1,3,4-thiadiazol-2-yl}-benzamide | 501.3/ 1.31 min |

TABLE 10-continued

| Example | Structure | Name | LC/MS [M + H]+/ RT |
|---|---|---|---|
| 104 | 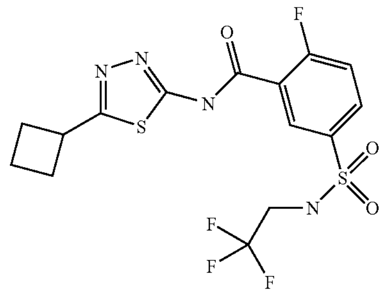 | N-(5-cyclobutyl-1,3,4-thiadiazol-2-yl)-2-fluoro-5-{[(2,2,2-trifluoroethyl)amino]-sulfonyl)benzamide | 439.0/ 0.95 min |
| 105 | 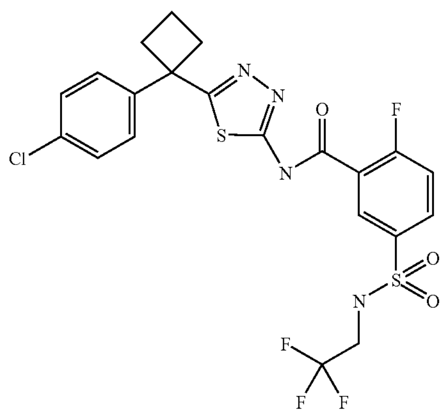 | N-{5-[1-(4-cyclobutyl]-1,3,4-thiadiazol-2-yl)-2-fluoro-5-{[(2,2,2-trifluoroethyl)amino]-sulfonyl}benzamide | 549.4/ 1.24 min |
| 106 | 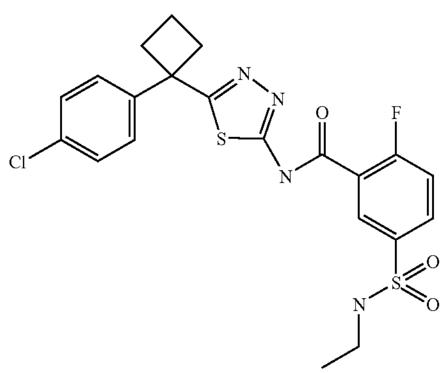 | N-{5-[1-(4-cyclobutyl]-1,3,4-thiadiazol-2-yl}-5-[(ethylamino)sulfonyl]-2-fluorobenzamide | 495.3/ 1.18 min |

General Procedure 13

To a 3 mL T-Vial (t=g) containing 5-(chlorosulfonyl)-2-fluorobenzoic acid (0.035 g, 0.147 mmol) in dichloromethane (1.0 ml) was added 3,3,3-trifluoro-1-propanamine (0.074 g, 0.440 mmol) in dichloromethane (1.0 ml) under stirred condition to give a colorless solution. DIPEA (0.077 ml, 0.440 mmol) was added into the amine solution. The mixture was stirred for 5 minutes and LC-MS was taken to show reaction completion. 1 N HCl (1.0 ml) was added into the solution and stirred overnight to quench the reaction. The organic layers were separated using phase separator and carried to next step without purification.

To a 4 mL T-Vial (t=g) containing 5-(sulfomide)-2-fluorobenzoic acid (0.056 g, 0.15 mmol) in DMF (0.5 ml) was added EDC (0.035 g, 0.180 mmol) and HOBt (0.028 g, 0.180 mmol) solution in N,N-dimethylformamide (0.5 ml) followed with addition of $Et_3N$ (0.025 ml, 0.180 mmol). The mixture was stirred for 10 minutes before the addition of 5-(1-methyl-1-phenylethyl)-1,3,4-thiadiazol-2-amine (0.039 g, 0.180 mmol) in N,N-dimethylformamide (0.5 ml) solution. The mixture was stirred overnight. The solution was evaporated after the LC-MS indicate the completion of reaction and purified by HPLC. The yield was between 5% and 36% for two steps.

The compounds in Table 11 were prepared from Intermediate 3 according to General Procedure 13. In the case of example 108, 2-fluoroethylamine was used in place of 3,3,3-trifluoro-1-propanamine.

TABLE 11

[Structure: 2-fluoro-benzamide with sulfonamide (SO2-NH-Ra) and N-linked to 5-(1-methyl-1-phenylethyl)-1,3,4-thiadiazol-2-yl group]

| Example | Ra | Name | LC/MS [M + H]+/ RT |
|---|---|---|---|
| 107 | (2,2,2-trifluoro-2-methylpropyl group) | 2-fluoro-N-[5-(1-methyl-1-phenylethyl)-1,3,4-thiadiazol-2-yl]-5-{[(2,2,2-trifluoroethyl)amino]-sulfonyl)benzamide | 517.2/ 1.14 min |
| 108 | (2-fluoroethyl-neopentyl group) | 2-fluoro-5-{[(2-fluoroethyl)amino]-sulfonyl}-N-[5-(1-methyl-1-phenylethyl) 1,3,4-thiadiazol-2-yl]-benzamide | 466.9/ 1.97 min |

The compound in Table 12 was prepared according to General Procedure 13 using 5-(4-fluorophenyl)-1,3,4-thiadiazol-2-amine instead of Intermediate 3 and cyclobutylamine in place of 3,3,3-trifluoro-1-propanamine.

TABLE 12

[Structure: 2-fluoro-benzamide with sulfonamide (SO2-NH-Ra) and N-linked to 5-(4-fluorophenyl)-1,3,4-thiadiazol-2-yl group]

| Example | Ra | Name | LC/MS [M + H]+/RT (min) |
|---|---|---|---|
| 109 | (cyclobutyl) | 5-[(cyclobutylamino)sulfonyl]-2-fluoro-N-[5-(4-fluorophenyl)-1,3,4-thiadiazol-2-yl]benzamide | 451/2.1 min |

Method of Treatment

Compounds of Formula (I), or a pharmaceutically acceptable salt thereof can be used in the manufacture of a medicine for the prophylactic or therapeutic treatment of any disease state in a human, or other mammal, which is exacerbated or caused by excessive or unregulated IL-8 cytokine production by such mammal's cell, such as, but not limited to, monocytes and/or macrophages, or other chemokines which bind to the IL-8 α or β receptor, also referred to as the type I or type II receptor.

Accordingly, the present invention provides a method of treating a chemokine mediated disease, wherein the chemokine is one which binds to an IL-8 α or β receptor and which method comprises administering an effective amount of a compound of Formula (I) or a pharmaceutically acceptable salt thereof. In particular, the chemokines are IL-8, GROα, GROβ, GROγ, NAP-2 or ENA-78.

The compounds of Formula (I) are administered in an amount sufficient to inhibit cytokine function, in particular IL-8, GROα, GROβ, GROγ, NAP-2 or ENA-78, such that they are biologically regulated down to normal levels of physiological function, or in some case to subnormal levels, so as to ameliorate the disease state. Abnormal levels of IL-8, GROα, GROβ, GROγ, NAP-2 or ENA-78, for instance, in the context of the present invention, constitute: (i) levels of free IL-8 greater than or equal to 1 picogram per mL; (ii) any cell associated IL-8, GROα, GROβ, GROγ, NAP-2 or ENA-78 above normal physiological levels; or (iii) the presence of IL-8, GROα, GROβ, GROγ, NAP-2 or ENA-78 above basal levels in cells or tissues in which IL-8, GROα, GROβ, GROγ, NAP-2 or ENA-78 respectively, is produced.

There are many disease states in which excessive or unregulated IL-8 production is implicated in exacerbating and/or causing the disease. Chemokine mediated diseases include psoriasis, atopic dermatitis, osteo arthritis, rheumatoid arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis, atherosclerosis, osteoporosis, gingivitis, viral diseases such as rhinovirus or undesired hematopoietic stem cell release. It is contemplated that the Formula (I) compounds may be particularly useful in treating asthma, chronic obstructive pulmonary disease and adult respiratory distress syndrome.

These diseases are primarily characterized by massive neutrophil infiltration, T-cell infiltration, or neovascular growth, and are associated with increased IL-8, GROα, GROβ, GROγ, NAP-2 or ENA-78 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ, NAP-2 or ENA-78 have the unique property of promoting neutrophil chemotaxis, enzyme release including but not limited to elastase release as well as superoxide production and activation. The α-chemokines, but particularly, GROα, GROβ, GROγ, NAP-2 or ENA-78, working through the IL-8 type I or II receptor, can promote the neovascularization of tumors by promoting the directional growth of endothelial cells. Therefore, the inhibition of IL-8 induced chemotaxis or activation would lead to a direct reduction in the neutrophil infiltration. Recent evidence also implicates the role of chemokines in the treatment of HIV infections.

Present evidence also indicates the use of IL-8 inhibitors in the treatment of atherosclerosis. The absence of IL-8 receptors on stem cells (and, therefore, on monocytes/macrophages) leads to a reduction in the development of atherosclerotic plaques in LDL receptor deficient mice.

The present invention also provides for a means of treating CNS injuries by the chemokine receptor antagonist compounds of Formula (I). Such treatment is provided in an acute setting, as well as for prevention of injury in those individuals deemed susceptible to injury.

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this area has been emerging and the present invention provides means for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. Treatment which reduced edema formation was found to improve functional outcome in those animals treated.

Compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formula (I) in the in vitro receptor binding assays which are described herein. Compounds of Formula (I) have been shown to be inhibitors of type II IL-8 receptors.

As used herein, the term "IL-8 mediated disease or disease state" refers to any and all disease states in which IL-8, GROα, GROβ, GROγ, NAP-2 or ENA-78 plays a role, either by production of IL-8, GROα, GROβ, GROγ, NAP-2 or ENA-78 themselves, or by IL-8, GROα, GROβ, GROγ, NAP-2 or ENA-78 causing another monokine to be released, such as but not limited to IL-1, IL-6 or TNF. A disease state in which, for instance, IL-1 is a major component, and whose production or action, is exacerbated or secreted in response to IL-8, would therefore be considered a disease state mediated by IL-8.

As used herein, the term "chemokine mediated disease or disease state" refers to any and all disease states in which a chemokine which binds to an IL-8 α or β receptor plays a role, such as but not limited to IL-8, GRO-α, GRO-β, GROγ, NAP-2 or ENA-78. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to IL-8, GRO-α, GRO-β, GRO-γ, NAP-2, ENA-78, IP-10, MIP-1α, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I) the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

Combinations:

The compound and pharmaceutical formulations according to the invention may be used in combination with or include one or more other therapeutic agents, for example selected from anti-inflammatory agents, anticholinergic agents (such as an $M_1/M_2/M_3$ receptor antagonist), $\beta_2$-adrenoreceptor agonists, antiinfective agents, such as antibiotics, antivirals, or antihistamines. The invention thus provides, in a further aspect, a combination comprising a compound of Formula (I) or a pharmaceutically acceptable salt, solvate or physiologically functional derivative thereof together with one or more other therapeutically active agents, for example selected from an anti-inflammatory agent, such as a corticosteroid or an NSAID, an anticholinergic agent, a $\beta_2$-adrenoreceptor agonist, an antiinfective agent, such as an antibiotic or an antiviral, or an antihistamine. One embodiment of the invention encompasses combinations comprising a compound of Formula (I) or a pharmaceutically acceptable salt, solvate or physiologically functional derivative thereof together with a $\beta_2$-adrenoreceptor agonist, and/or an anticholinergic, and/or a PDE-4 inhibitor, and/or an antihistamine.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of the invention together with a $\beta_2$-adrenoreceptor agonist. Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $\beta_2$-adrenoreceptor agonists are long-acting $\beta_2$-adrenoreceptor agonists, for example, compounds which provide effective bronchodilation for about 12 hours or longer.

Suitable anti-inflammatory agents include corticosteroids. Examples of corticosteroids which may be used in combination with the compounds of the invention are those oral and inhaled corticosteroids and their pro-drugs which have anti-inflammatory activity.

Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolonc acetonide, rofleponidc, ciclesonide (16α,17-[[(R)-cyclohexylmethylenc]bis(oxy)]-11β,21-dihydroxy-pregna-1,4-diene-3,20-dione), butixocort propionate, RPR-106541, and ST-126. In one embodiment corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethylcyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene to synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors.

In one embodiment the invention provides the use of the compounds of Formula (I) in combination with a phosphodiesterase 4 (PDE4) inhibitor, for example in the case of a formulation adapted for inhalation. The PDE4 inhibitor useful in this aspect of the invention may be any compound that is known to or which is discovered to act as a PDE4 inhibitor, e.g. as an inhibitor of PDE4B and/or PDE4D.

PDE4 inhibitory compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms are included.

Examples of anticholinergic agents are those compounds that act as antagonists at the muscarinic receptors, in particular those compounds which are antagonists of the $M_1$ or $M_3$ receptors, dual antagonists of the $M_{1/M3}$ or $M_2/M_3$ receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium.

In one embodiment, the invention provides a combination comprising a compound of Formula (I) or a pharmaceutically acceptable salt thereof together with a CCR5 receptor antagonist, such as 4,4-difluoro-N-((1S)-3-{3-[3-methyl-5-(1-methylethyl)-4H-1,2,4-triazol-4-yl]-8-azabicyclo[3.2.1]oct-8-yl}-1-phenylpropyl)cyclohexanecarboxamide:

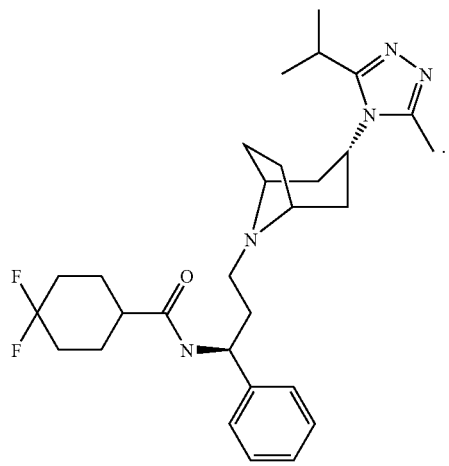

In one embodiment, the invention provides a combination comprising a compound of Formula (I) or a pharmaceutically acceptable salt thereof together with a CXCR3 receptor antagonist such as N-((1R)-1-{3-[4-(ethyloxy)phenyl]-4-oxo-3,4-dihydropyrido[2,3-d]pyrimidin-2-yl}ethyl)-N-(3-pyridinylmethyl)-2-{4-[(trifluoromethyl)oxy]phenyl}acetamide:

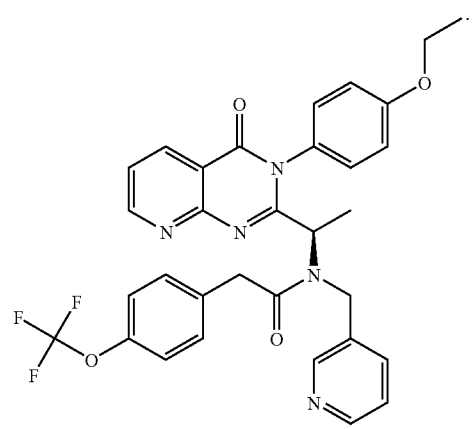

In another embodiment, the invention provides a combination comprising a compound of Formula (I) or a pharmaceutically acceptable salt thereof together with a CCR2 antagonist such as 1,5-anhydro-2,3-dideoxy-4-O-methyl-3-[((1R,3S)-3-(1-methylethyl)-3-{[3-(trifluoromethyl)-7,8-dihydro-1,6-naphthyridin-6(5H)-yl]carbonyl}cyclopentyl)amino]-D-glycero-pentitol:

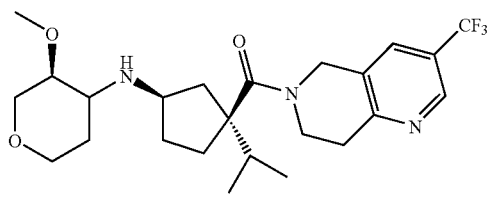

The invention thus provides, in a further aspect, a combination comprising a compound of Formula (I) and/or a pharmaceutically acceptable salt, solvate or physiologically functional derivative thereof together with a PDE4 inhibitor.

The invention thus provides, in a further aspect, a combination comprising a compound of Formula (I) and/or a pharmaceutically acceptable salt, solvate or physiologically functional derivative thereof together with a $\beta_2$-adrenoreceptor agonist.

The invention thus provides, in a further aspect, a combination comprising a compound of Formula (I) and/or a pharmaceutically acceptable salt, solvate or physiologically functional derivative thereof together with a corticosteroid.

The invention thus provides, in a further aspect, a combination comprising a compound of Formula (I) and/or a pharmaceutically acceptable salt, solvate or physiologically functional derivative thereof together with a non-steroidal GR agonist.

The invention thus provides, in a further aspect, a combination comprising a compound of Formula (I) and/or a pharmaceutically acceptable salt, solvate or physiologically functional derivative thereof together with an anticholinergic.

The invention thus provides, in a further aspect, a combination comprising a compound of Formula (I) and/or a pharmaceutically acceptable salt, solvate or physiologically functional derivative thereof together with an antihistamine.

The invention thus provides, in a further aspect, a combination comprising a compound of Formula (I) and/or a pharmaceutically acceptable salt, solvate or physiologically functional derivative thereof together with a PDE4 inhibitor and a $\beta_2$-adrenoreceptor agonist.

The invention thus provides, in a further aspect, a combination comprising a compound of Formula (I) and/or a pharmaceutically acceptable salt, solvate or physiologically functional derivative thereof together with an anticholinergic and a PDE-4 inhibitor.

The invention thus provides, in a further aspect, a combination comprising a compound of Formula (I) and/or a pharmaceutically acceptable salt, solvate or physiologically functional derivative thereof together with a CCR2 inhibitor.

The invention thus provides, in a further aspect, a combination comprising a compound of Formula (I) and/or a pharmaceutically acceptable salt, solvate or physiologically functional derivative thereof together with a CCR5 inhibitor.

The invention thus provides, in a further aspect, a combination comprising a compound of Formula (I) and/or a pharmaceutically acceptable salt, solvate or physiologically functional derivative thereof together with a CXCR3 inhibitor.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention. The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of the invention together with another therapeutically active agent.

The invention thus provides, in a further aspect, a pharmaceutical composition comprising a combination of a compound of the invention together with a PDE4 inhibitor.

The invention thus provides, in a further aspect, a pharmaceutical composition comprising a combination of a compound of the invention together with a $\beta_2$-adrenoreceptor agonist.

The invention thus provides, in a further aspect, a pharmaceutical composition comprising a combination of a compound of the invention together with a corticosteroid.

The invention thus provides, in a further aspect, a pharmaceutical composition comprising a combination of a compound of the invention together with a non-steroidal GR agonist.

The invention thus provides, in a further aspect, a pharmaceutical composition comprising a combination of a compound of the invention together with an anticholinergic.

The invention thus provides, in a further aspect, a pharmaceutical composition comprising a combination of a compound of the invention together with an antihistamine.

The invention thus provides, in a further aspect, a pharmaceutical composition comprising a combination of a compound of the invention together with CXCR3 receptor antagonist.

The invention thus provides, in a further aspect, a pharmaceutical composition comprising a combination of a compound of the invention together with a CCR5 receptor antagonist.

The invention thus provides, in a further aspect, a pharmaceutical composition comprising a combination of a compound of the invention together with a CCR2 receptor antagonist.

The invention will now be described by reference to the following biological examples which are merely illustrative and are not to be construed as a limitation of the scope of the present invention.

BIOLOGICAL EXAMPLES

The IL-8, and GRO-α chemokine inhibitory effects of compounds of the present invention are determined by the following in vitro assay:

Receptor Binding Assays:

[$^{125}$I] IL-8 (human recombinant) was obtained from GE Healthcare, with specific activity 2000 Ci/mmol. All other chemicals were of analytical grade. High levels of recombinant human CXCR1 (IL-8 type α) and CXCR2 (IL-8 type β) receptors were individually expressed in non-adherent Chinese Hamster Ovary (CHO) cells as described previously (Holmes, et al., *Science,* 1991, 253, 1278). The membranes were prepared according to a previously described protocol, Haour, et al., *J. Biol. Chem.,* 249 pp 2195-2205 (1974)), incorporated herein by reference to the extent required to prepare the present membranes, except that the homogenization buffer was modified to 40 mM Tris-HCL (pH 7.5), 1 mM $MgSO_4$, 0.5 mM EGTA (ethylene-glycol-bis(2-aminoethyl-ether)-N,N,N',N' tetra-acetic acid), 1 mM PMSF (α-toluene-sulphonyl fluoride), 2.5 mg/L leupeptin and 0.1 mg/ml aprotinin. Cells were homogenized and centrifuged at 2,000 rpm for 10 min. The supernatant was centrifuged at 100,000×g for 1 hour. Supernatant was discarded and membranes stored at −80° C. Membrane protein concentration was determined using BioRad reagent according to manufactures protocol using bovine serum albumin (BSA) as a standard.

All IL-8 binding was conducted using Scintillation Proximity Assays (SPA) using wheatgerm agglutinin beads in a 96-well plate format. Membranes CHO-CXCR1 or CHO-CXCR2 were preincubated with the beads in the binding buffer for 30 min. for 4° C. Buffer contained 20 mM Bis-Trispropane buffer, pH 8.0, containing 1 mM $MgSO_4$, 0.1 mM EDTA and 25 mM NaCl. Compounds were diluted in DMSO at 20× the final dilution (final compound concentration between 1 nM and 30 uM and final DMSO concentration of 5%). Assay was performed in 96-well plates (optiplate 96, Packard) at room temperature, in 0.1 ml binding buffer with membranes and 0.04% CHAPS (3-[(3-cholamidopropyl) dimethylammonio]-1-propanesulfonate), 0.0025% BSA and 0.23 nM [$^{125}$I] IL-8. Plates were shaken on a platform for 1 hour, at the end of incubation the plates were spun at 2,000 rpm for 5 min and counted in a Top Count counter The recombinant IL-8 Rα, CXCR1 or Type I, receptor is also referred to herein as the non-permissive receptor and the recombinant IL-8 Rβ, CXCR2 or Type II, receptor is referred to as the permissive receptor.

Examples 1,4-7, 20, 22, 23, 27, 30, 36-39, 41, 42, 44-47, 49-51, 59 and 107 exhibited positive inhibitory activity in this assay at $IC_{50}$ levels <10 uM, and would be considered active. The compounds tested represented a range of from about 38 nM to about 7 uM.

Chemotaxis Assay:

The in vitro inhibitory properties of these compounds were determined in a neutrophil chemotaxis assay. Primary human neutrophils were isolated from peripheral whole blood using percoll discontinuous gradient centrifugation, dextran sedimentation and hypotonic lysis. The chemoattractants IL-8 (CXCL8) or GRO-α (CXCL1) were placed in the bottom chamber of a 96 multi-well chamber (ChemoTx System, Neuro Probe, Gaithersburg, Md.). The agonist concentration used was an EC80 concentration. The two chambers are separated by a 5 um polycarbonate membrane. When compounds of this invention were tested, they were preincubated with the cells prior to placement on the top of the filter. Chemotaxis was allowed to proceed for 45 minutes in a humidified incubator at 37° C. with 5% $CO_2$. At the end of the incubation period, the membrane was removed and the migrated cells in the bottom chamber were transferred to a 96-well plate. These cells were measured using a luminescent cell viability assay (Celltiter-Glo, Promega, Madison, Wis.). Each sample was tested in duplicate and each compound repeated at least three times. Positive control cells were cells without compound added and represent the maximum chemotactic response. The negative control (unstimulated) was with no chemokine added to the bottom chamber. The difference between the positive control and the negative control represents the chemotactic activity of the cells.

Examples 1, 6, 18, 20, 22, 27, 29, 36, 39, 44, 49, 57-59, 63, 72, 76-77, 92 and 107 were tested in this assay. A compound is considered active at $IC_{50}$ values <10 uM. The compounds tested represented a range of activity from about 63 nM to about 8 uM.

CD11b Human Whole Blood Assay:

The compounds indicated were tested for their ability to inhibit the GROα-induced expression of the integrin CD11b on neutrophils in human whole blood.

Blood was drawn (9 ml) using a butterfly line and a 10 ml syringe containing 0.2 ml of working Sodium Heparin. The blood was kept at 37° C. until placed on ice in step 5 below. Compound stock solutions were then diluted to 12 times the maximum final concentration, 120 uM. Half Log serial dilutions were then performed in vehicle. Ten microliters of the compound dilutions or vehicle were then added to the appropriate 12×75 polypropylene tubes. One hundred microliters of whole blood was added per tube and incubated for 10 minutes, in a 37° C. water bath with initial (gentle) agitation and again at 5 minutes. The GROα stock was diluted 1:166.66 in 0.1% BSA-DPBS to "12x" concentration of 120 nM and 10 ul of the GROα dilution or 0.1% BSA-DPBS was added to the appropriate tubes so that the final GROα concentration equaled 10 nM. The tubes were incubated for 10 min at 37° C. with gentle hand agitation and again at 5 minutes. Samples were then placed on ice and 250 ul of ice cold CellFix working dilution was added followed by a one minute incubation on ice. 1.5 ml Eppendorf tubes were readied during GROα incubation by adding the appropriate antibodies. Every tube received 10 ul of CD11b-FITC and 5 ul of CD 16-PE, except for the isotype control which received 10 ul of IgG2a-FITC instead of CD11b. Addition of 50 ul of the fixed blood from each tube was added to the appropriate Eppendorf tube. Samples were allowed to then incubate for 20 min at 4° C. in the dark. Addition of the blood/antibody mixtures to 500 ul of cold DPBS were added to the appropriately labeled 12×75 polystyrene tube. The resulting mixture was kept on ice. LDS stock (10 ul) was added and the mixture was incubated for 10 min at 4° C. before flow analysis. Samples were kept in a darkened environment. The LDS addition was staggered as the samples were collected on the flow cytometer so that all samples were run ~10-20 minutes post-LDS addition.

Medium flow rate was used for flow collection and FL3 threshold increased to eliminate red blood cells from analysis using the LDS signal. The color compensation was properly set using unlabeled samples and one-color samples to subtract LDS spill into PE and the PE spill into FITC and FITC into PE. For the BD LSR cytometer, LDS=FL3, PE=FL2, FITC=FL1. A minimum of 2000-3000 events that satisfy the granulocyte gate by SSC vs. FSC and were CD16 positive by the FL2 signal were collected.

Exemplified compounds of Formula (I), Examples 28, 52, 61 and 107 exhibited positive inhibitory activity in this assay at $IC_{50}$ values of <5 uM, and would be considered active. The tested compounds had an $IC_{50}$ value from about 0.5 uM to about 4 uM.

Calcium Mobilization in CHO-K1 Cells Stably Expressing CXCR2 and Gα16:

CHO-K1 cells stably expressing CXCR2 and Gα16 were grown to 80% confluency in DMEM/F12 (HAM's)1:1, w/10% FCS (heat inactivated), w/2 mM L-glutamine, w/0.4 mg/ml G418 while maintained at 37° C. in a 5% $CO_2$ incubator. Twenty four hours previous to assay, cells were harvested and plated, 40,000 cells per well, in a 96 well, black wall, clear bottom plate (Packard View) and returned to $CO_2$ incubator. On the day of assay, compounds were serially diluted in 100% DMSO to 300× the desired assay concentration. Growth media is aspirated off cells and replaced with 100 ul of load media (EMEM with Earl's salts w/L-Glutamine, 0.1% BSA, (Bovuminar Cohen Fraction V from Seriologicals Corp.), 4 uM Fluo-4-acetoxymethyl ester fluorescent indicator dye (Fluo-4 AM, from Molecular Probes), and 2.5 mM probenecid) and incubated for 1 hour at 37° C. in $CO_2$ incubator. Load media was aspirated and replaced with 100 uL of EMEM with Earl's salts w/L-Glutamine, 0.1% gelatin, and 2.5 mM probenecid and incubated for an additional 10 min. Serially diluted compound (3 ul) in DMSO at 300× was transferred to a 96 well plate containing 297 micro liters of KRH (120 mM NaCl, 4.6mM KCl, 1.03 mM $KH_2PO_4$, 25 mM $NaHCO_3$, 1.0 mM $CaCl_2$, 1.1 mM $MgCl_2$, 11 mM Glucose, 20 mM HEPES (pH 7.4)) w/2.5 mM probenecid and 0.1% gelatin (compound now at 3×). Media was aspirated off cells, and cells washed 3 times with KRH w/2.5 mM probenecid, w/0.1% gelatin. KRH (100 ul) w/2.5 mM probenecid with 0.1% gelatin was added to wells then 50 ul of 3× compound in KRH w/2.5 mM probenecid and 0.1% gelatin was added to wells (compound now at 1×) and incubated at 37° C. in $CO_2$ incubator for 10 min. Plates were placed onto FLIPR (Fluorometric Imaging Plate Reader, Molecular Devices, Sunnyvale Calif.) for analysis as described previously (Sarau et al., 1999). The percent of maximal human IL-8 induced $Ca^{2+}$ mobilization induced by 1.0 nM IL-8, an $EC_{80}$ conc. for CXCR2, was determined for each concentration of compound and the $IC_{50}$ calculated as the concentration of test compound that inhibits 50% of the maximal response induced by 1.0 nM IL-8. Examples 1-109 exhibited positive inhibitory activity in this assay at $IC_{50}$) values of <10 uM and would be considered active. The compounds tested by the above assay had an $IC_{50}$ from about 3 uM to about 8 nM.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:
1. A compound of Formula (I):

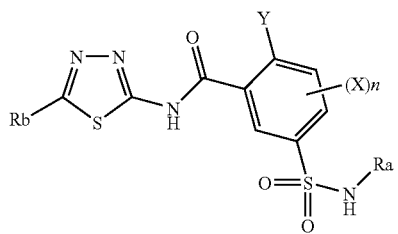

(I)

wherein:
Y is halogen;
n is 0, 1 or 2;
X is halogen;
Ra is selected from the group consisting of hydrogen, $C_{1-4}$alkyl, $C_{3-6}$cycloalkyl, $C_{3-6}$cycloalkyl$C_{1-4}$alkyl, and phenyl, wherein all moieties, except hydrogen, are optionally substituted, one to three times, by halogen, $CF_3$, OH or $C_{1-4}$alkyl; and
Rb is selected from the group consisting of phenyl, $C_{1-4}$alkyl, phenyl$C_{1-4}$alkyl, $C_{3-6}$cycloalkyl, phenyl$C_{3-6}$cycloalkyl and heteroaryl, wherein all moieties are optionally substituted, one to four times, by halogen, $CF_3$ or $C_{1-4}$alkyl;
or a pharmaceutically acceptable salt thereof.

2. A compound according to claim 1 wherein Y is F.
3. A compound according to claim 1 wherein n is 0.
4. A compound according to claim 1 wherein n is 1 and the X substituent is at the 3-or 4-position on the phenyl ring.
5. A compound according to claim 1 wherein n is 2 and the X substituent is at the 3- and 4-position on the phenyl ring.
6. A compound according to claim 1 wherein Ra is hydrogen.
7. A compound according to claim 1 wherein Ra is $C_{1-4}$alkyl or $C_{1-4}$alkyl substituted once by $CF_3$, halogen or $C_{1-4}$alkyl.
8. A compound according to claim 1 wherein Ra is $C_{3-6}$cycloalkyl or $C_{3-6}$cycloalkyl$C_{1-4}$alkyl.
9. A compound according to claim 1 wherein Ra is phenyl or phenyl substituted, independently, one to four times, by Cl or F.
10. A compound according to claim 1 wherein Rb is alkyl.
11. A compound according to claim 1 wherein Rb is phenyl$C_{1-4}$alkyl or phenyl$C_{1-4}$alkyl wherein the phenyl ring is substituted once by halogen.
12. A compound according to claim 1 wherein Rb is $C_{3-6}$cycloalkyl or $C_{3-6}$cycloalkyl substituted, independently, once or twice, by halogen, methyl or $CF_3$.
13. A compound according to claim 1 wherein Rb is phenyl$C_{3-6}$cycloalkyl, wherein the phenyl ring is optionally substituted, once or twice, independently, by methyl, halogen or $CF_3$.
14. A compound according to claim 1 wherein Rb is heteroaryl, optionally substituted, once or twice by methyl.
15. A compound according to claim 1 selected from the group consisting of
5-[(ethylamino)sulfonyl]-2-fluoro-N-[5-(1-methyl-1-phenylethyl)-1,3,4-thiadiazol-2-yl]benzamide;
5-(aminosulfonyl)-2-chloro-N-(5-cyclohexyl-1,3,4-thiadiazol-2-yl)benzamide;
2-fluoro-N-{5-[1-(4-fluorophenyl)-1-methylethyl]-1,3,4-thiadiazol-2-yl}-5-{[(2,2,2-trifluoroethyl)amino]sulfonyl}benzamide;
5-(aminosulfonyl)-2-chloro-N-[5-(4-fluorophenyl)-1,3,4-thiadiazol-2-yl]benzamide;
5-(aminosulfonyl)-2,3-dichloro-N-[5-(4-fluorophenyl)-1,3,4-thiadiazol-2-yl]benzamide;
5-[(ethylamino)sulfonyl]-2,3-difluoro-N-[5-(4-fluorophenyl)-1,3,4-thiadiazol-2-yl]benzamide;
5-[(ethylamino)sulfonyl]-2-fluoro-N-[5-(4-fluorophenyl)-1,3,4-thiadiazol-2-yl]benzamide;
5-(aminosulfonyl)-N-(5-cyclopentyl-1,3,4-thiadiazol-2-yl)-2-fluorobenzamide;
N-[5-(1,1-dimethylethyl)-1,3,4-thiadiazol-2-yl]-5-[(ethylamino)sulfonyl]-2-iodobenzamide;
3-chloro-5-[(ethylamino)sulfonyl]-2,4-difluoro-N-[5-(1-methyl-1-phenylethyl)-1,3,4-thiadiazol-2-yl]benzamide;
3-chloro-N-[5-(1,1-dimethylethyl)-1,3,4-thiadiazol-2-yl]-5-[(ethylamino)sulfonyl]-2,4-difluorobenzamide;
3-chloro-5-[(ethylamino)sulfonyl]-2,4-difluoro-N-[5-(4-fluorophenyl)-1,3,4-thiadiazol-2-yl]benzamide;
5-[(ethylamino)sulfonyl]-2,3,4-trifluoro-N-[5-(1-methyl-1-phenylethyl)-1,3,4-thiadiazol-2-yl]benzamide;
3-chloro-5-[(ethylamino)sulfonyl]-2-fluoro-N-[5-(1-methyl-1-phenylethyl)-1,3,4-thiadiazol-2-yl]benzamide;
3-chloro-N-[5-(1,1-dimethylethyl)-1,3,4-thiadiazol-2-yl]-5-[(ethylamino)sulfonyl]-2-fluorobenzamide;

N-(5-cyclopentyl-1,3,4-thiadiazol-2-yl)-5-[(ethylamino) sulfonyl]-2,4-difluorobenzamide;
3-[(ethylamino)sulfonyl]-2,6-difluoro-N-[5-(4-fluorophenyl)-1,3,4-thiadiazol-2-yl]benzamide;
2-fluoro-N-[5-(4-fluorophenyl)-1,3,4-thiadiazol-2-yl]-5-{[(2-methylpropyl)amino]sulfonyl}benzamide;
5-[(butylamino)sulfonyl]-2-fluoro-N-[5-(4-fluorophenyl)-1,3,4-thiadiazol-2-yl]benzamide;
2-fluoro-N-[5-(4-fluorophenyl)-1,3,4-thiadiazol-2-yl]-5-[(propylamino)sulfonyl]benzamide;
2-chloro-5-[(ethylamino)sulfonyl]-3-fluoro-N-[5-(4-fluorophenyl)-1,3,4-thiadiazol-2-yl]benzamide;
2,3-difluoro-N-[5-(4-fluorophenyl)-1,3,4-thiadiazol-2-yl]-5-[(propylamino)sulfonyl]benzamide;
3-chloro-5-[(ethylamino)sulfonyl]-2-fluoro-N-[5-(4-fluorophenyl)-1,3,4-thiadiazol-2-yl]benzamide;
N-[5-(1,1-dimethylethyl)-1,3,4-thiadiazol-2-yl]-2-fluoro-5-{[(2,2,2-trifluoroethyl) amino] sulfonyl}benzamide;
2-fluoro-N-[5-(4-fluorophenyl)-1,3,4-thiadiazol-2-yl]-5-{[(2,2,2-trifluoroethyl) amino]sulfonyl}benzamide;
N-[5-(1,1-dimethylethyl)-1,3,4-thiadiazol-2-yl]-5-[(ethylamino)sulfonyl]-2,3-difluorobenzamide;
N-[5-(1,1-dimethylethyl)-1,3,4-thiadiazol-2-yl]-5-[(ethylamino)sulfonyl]-2-fluorobenzamide;
5-[(ethylamino)sulfonyl]-2,3-difluoro-N-[5-(1-methyl-1-phenylethyl)-1,3,4-thiadiazol-2-yl]benzamide;
2-fluoro-N-[5-(4-fluorophenyl)-1,3,4-thiadiazol-2-yl]-5-[(phenylamino)sulfonyl]benzamide;
5-(aminosulfonyl)-4-chloro-2-fluoro-N-[5-(4-fluorophenyl)-1,3,4-thiadiazol-2-yl]benzamide;
2,3-dichloro-5-[(ethylamino)sulfonyl]-N-[5-(1-methyl-1-phenylethyl)-1,3,4-thiadiazol-2-yl]benzamide;
2,3-dichloro-N-[5-(1,1-dimethylethyl)-1,3,4-thiadiazol-2-yl]-5-[(ethylamino)sulfonyl]benzamide;
2,3-dichloro-5-[(ethylamino)sulfonyl]-N-[5-(4-fluorophenyl)-1,3,4-thiadiazol-2-yl]benzamide;
2-bromo-5-[(ethylamino)sulfonyl]-N-[5-(4-fluorophenyl)-1,3,4-thiadiazol-2-yl]benzamide;
2-bromo-N-[5-(4-fluorophenyl)-1,3,4-thiadiazol-2-yl]-5-[(propylamino)sulfonyl]benzamide;
5-(aminosulfonyl)-2,3-dichloro-N-[5-(1-methyl-1-phenylethyl)-1,3,4-thiadiazol-2-yl]benzamide;
5-(aminosulfonyl)-2-chloro-N-[5-(1-methyl-1-phenylethyl)-1,3,4-thiadiazol-2-yl]benzamide;
5-(aminosulfonyl)-4-chloro-2-fluoro-N-[5-(4-fluorophenyl)-1,3,4-thiadiazol-2-yl]benzamide;
5-(aminosulfonyl)-2,4-dichloro-N-[5-(4-fluorophenyl)-1,3,4-thiadiazol-2-yl]benzamide;
5-(aminosulfonyl)-N-[5-(1,1-dimethylethyl)-1,3,4-thiadiazol-2-yl]-2-fluorobenzamide;
N-[5-(1,1-dimethylethyl)-1,3,4-thiadiazol-2-yl]-2-fluoro-5-{[(1-methylethyl)amino]sulfonyl}benzamide;
5-[(cyclopropylamino)sulfonyl]-N-[5-(1,1-dimethylethyl)-1,3,4-thiadiazol-2-yl]-2-fluorobenzamide;
N-[5-(1,1-dimethylethyl)-1,3,4-thiadiazol-2-yl]-2-fluoro-5-[(methylamino)sulfonyl]benzamide;
2-bromo-N-[5-(1,1-dimethylethyl)-1,3,4-thiadiazol-2-yl]-5-[(methylamino)sulfonyl]benzamide;
5-(aminosulfonyl)-2-fluoro-N-[5-(4-fluorophenyl)-1,3,4-thiadiazol-2-yl]benzamide;
2-fluoro-N-[5-(4-fluorophenyl)-1,3,4-thiadiazol-2-yl]-5-{[(1-methylethyl)amino]sulfonyl}benzamide;
5-[(cyclopropylamino)sulfonyl]-2-fluoro-N-[5-(4-fluorophenyl)-1,3,4-thiadiazol-2-yl]benzamide;
2-fluoro-N-[5-(4-fluorophenyl)-1,3,4-thiadiazol-2-yl]-5-[(methylamino)sulfonyl]benzamide;

2-fluoro-N-[5-(1-methyl-1-phenylethyl)-1,3,4-thiadiazol-2-yl]-5-{[(3,3,3-trifluoropropyl) amino] sulfonyl}benzamide;
5-[(cyclopropylamino)sulfonyl]-2-fluoro-N-[5-(1-methyl-1-phenylethyl)-1,3,4-thiadiazol-2-yl]benzamide;
N-[5-(1,1-dimethyl-2-phenylethyl)-1,3,4-thiadiazol-2-yl]-5-[(ethylamino)sulfonyl]-2-fluorobenzamide;
5-[(ethylamino)sulfonyl]-2-fluoro-N-{5-[1-(4-fluorophenyl)cyclopentyl]-1,3,4-thiadiazol-2-yl}benzamide;
5-[(ethylamino)sulfonyl]-2-fluoro-N-[5-(1-phenylcyclopentyl)-1,3,4-thiadiazol-2-yl]benzamide;
5-[(ethylamino)sulfonyl]-2-fluoro-N-[5-(1-phenylcyclopropyl)-1,3,4-thiadiazol-2-yl]benzamide;
5-[(cyclopropylamino)sulfonyl]-2-fluoro-N-{5-[1-(4-fluorophenyl)cyclopentyl]-1,3,4-thiadiazol-2-yl}benzamide;
5-(aminosulfonyl)-2-chloro-N-{5-[1-(4-fluorophenyl)-1-methylethyl]-1,3,4-thiadiazol-2-yl}benzamide;
5-[(cyclopropylamino)sulfonyl]-N-[5-(1,1-dimethyl-2-phenylethyl)-1,3,4-thiadiazol-2-yl]-2-fluorobenzamide;
5-[(ethylamino)sulfonyl]-2-fluoro-N-[5-(1-methylcyclohexyl)-1,3,4-thiadiazol-2-yl]benzamide;
N-(5-cyclopentyl-1,3,4-thiadiazol-2-yl)-5-[(ethylamino) sulfonyl]-2-fluorobenzamide;
5-[(ethylamino)sulfonyl]-2-fluoro-N-[5-(1-methylcyclopentyl)-1,3,4-thiadiazol-2-yl]benzamide;
N-[5-(4,4-difluorocyclohexyl)-1,3,4-thiadiazol-2-yl]-5-[(ethylamino)sulfonyl]-2-fluorobenzamide;
5-(aminosulfonyl)-2-fluoro-N-[5-(1-methyl-1-phenylethyl)-1,3,4-thiadiazol-2-yl]benzamide;
5-[(ethylamino)sulfonyl]-2-fluoro-N-[5-(1-phenylethyl)-1,3,4-thiadiazol-2-yl]benzamide;
5-[(ethylamino)sulfonyl]-2-fluoro-N-{5-[1-(2-fluorophenyl)-1-methylethyl]-1,3,4-thiadiazol-2-yl}benzamide;
5-[(ethylamino)sulfonyl]-2,3-difluoro-N-{5-[1-(2-fluorophenyl)-1-methylethyl]-1,3,4-thiadiazol-2-yl}benzamide;
5-[(ethylamino)sulfonyl]-2,3-difluoro-N-[5-(1-phenylcyclopentyl)-1,3,4-thiadiazol-2-yl]benzamide;
5-[(ethylamino)sulfonyl]-2,3-difluoro-N-[5-(1-methylcyclopentyl)-1,3,4-thiadiazol-2-yl]benzamide;
5-(aminosulfonyl)-N-{5-[1-(4-bromophenyl)-1-methylethyl]-1,3,4-thiadiazol-2-yl}-2-fluorobenzamide;
5-(aminosulfonyl)-2-fluoro-N-{5-[2-fluoro-4-(trifluoromethyl)phenyl]-1,3,4-thiadiazol-2-yl}benzamide;
5-(aminosulfonyl)-N-[5-(2-chloro-4-fluorophenyl)-1,3,4-thiadiazol-2-yl]-2-fluorobenzamide;
N-[5-(2-chloro-4-fluorophenyl)-1,3,4-thiadiazol-2-yl]-2-fluoro-5-{[(2,2,2-trifluoroethyl)amino] sulfonyl}benzamide;
2-fluoro-N-[5-(2-methyl-3-furanyl)-1,3,4-thiadiazol-2-yl]-5-{[(2,2,2-trifluoroethyl)amino] sulfonyl}benzamide;
2-fluoro-N-{5-[1-(3-fluorophenyl)cyclobutyl]-1,3,4-thiadiazol-2-yl}-5-{[(2,2,2-trifluoroethyl)amino] sulfonyl}benzamide;
2-fluoro-5-{[(2,2,2-trifluoroethyl)amino]sulfonyl}-N-{5-[1-(trifluoromethyl)cyclopentyl]-1,3,4-thiadiazol-2-yl}benzamide;
5-[(ethylamino)sulfonyl]-2-fluoro-N-{5-[1-(trifluoromethyl)cyclopentyl]-1,3,4-thiadiazol-2-yl}benzamide;
5-{[(cyclopropylmethyl)amino]sulfonyl}-2-fluoro-N-{5-[1-(trifluoromethyl)cyclopentyl]-1,3,4-thiadiazol-2-yl}benzamide;
5-[(ethylamino)sulfonyl]-2-fluoro-N-{5-[1-(3-fluorophenyl)cyclobutyl]-1,3,4-thiadiazol-2-yl}benzamide;

5-{[(cyclopropylmethyl)amino]sulfonyl}-2-fluoro-N-{5-[1-(3-fluorophenyl)cyclobutyl]-1,3,4-thiadiazol-2-yl}benzamide;

5-(aminosulfonyl)-2-fluoro-N-{5-[1-(3-fluorophenyl)cyclobutyl]-1,3,4-thiadiazol-2-yl}benzamide;

5-{[(cyclopropylmethyl)amino]sulfonyl}-2-fluoro-N-[5-(2-methyl-3-furanyl)-1,3,4-thiadiazol-2-yl]benzamide;

5-{[(cyclopropylmethyl)amino]sulfonyl}-2-fluoro-N-[5-(3-methyl-2-thienyl)-1,3,4-thiadiazol2-yl]benzamide;

N-[5-(2,5-dimethyl-3-furanyl)-1,3,4-thiadiazol-2-yl]-5-[(ethylamino)sulfonyl]-2-fluorobenzamide;

5-{[(cyclopropylmethyl)amino]sulfonyl}-N-[5-(2,5-dimethyl-3-furanyl)-1,3,4-thiadiazol-2-yl]-2-fluorobenzamide;

N-[5-(4-chloro-2-fluorophenyl)-1,3,4-thiadiazol-2-yl]-5-{[(cyclopropylmethyl)amino]sulfonyl}-2-fluorobenzamide;

5-{[(cyclopropylmethyl)amino]sulfonyl}-2-fluoro-N-{5-[2-fluoro-4-(trifluoromethyl)phenyl]-1,3,4-thiadiazol-2-yl}benzamide;

5-{[(cyclopropylmethyl)amino]sulfonyl}-2-fluoro-N-[5-(2,3,4,5-tetrafluorophenyl)-1,3,4-thiadiazol-2-yl]benzamide;

N-{5-[1-(4-bromophenyl)-1-methylethyl]-1,3,4-thiadiazol-2-yl}-5-{[(cyclopropylmethyl)amino]sulfonyl}-2-fluorobenzamide;

N-[5-(2-chloro-4-fluorophenyl)-1,3,4-thiadiazol-2-yl]-5-{[(cyclopropylmethyl)amino]sulfonyl}-2-fluorobenzamide;

2-fluoro-N-[5-(1-phenylcyclobutyl)-1,3,4-thiadiazol-2-yl]-5-{[(2,2,2-trifluoroethyl)amino]sulfonyl}benzamide;

5-(aminosulfonyl)-2-fluoro-N-[5-(1-phenylcyclobutyl)-1,3,4-thiadiazol-2-yl]benzamide;

5-(aminosulfonyl)-2-fluoro-N-{5-[1-(4-fluorophenyl)cyclobutyl]-1,3,4-thiadiazol-2-yl}benzamide;

5-(aminosulfonyl)-2-fluoro-N-{5-[1-(trifluoromethyl)cyclobutyl]-1,3,4-thiadiazol-2-yl}benzamide;

5-[(ethylamino)sulfonyl]-2-fluoro-N-[5-(1-phenylcyclobutyl)-1,3,4-thiadiazol-2-yl]benzamide;

5-[(ethylamino)sulfonyl]-2-fluoro-N-{5-[1-(4-fluorophenyl)cyclobutyl]-1,3,4-thiadiazol-2-yl}benzamide;

5-[(ethylamino)sulfonyl]-2-fluoro-N-(5-{1-[3-(trifluoromethyl)phenylcyclobutyl]-1,3,4-thiadiazol-2-yl}benzamide;

5-{[(cyclopropylmethyl)amino]sulfonyl}-2-fluoro-N-[5-(1-phenylcyclobutyl)-1,3,4-thiadiazol-2-yl]benzamide;

5-{[(cyclopropylmethyl)amino]sulfonyl}-N-{5-[1-(2,4-difluorophenyl)cyclobutyl]-1,3,4-thiadiazol-2-yl}-2-fluorobenzamide;

2-fluoro-N-{5-[1-(2-fluorophenyl)cyclobutyl]-1,3,4-thiadiazol-2-yl}-5-{[(2,2,2-trifluoroethyl)amino]sulfonyl}benzamide;

5-(aminosulfonyl)-N-{5-[1-(2,4-difluorophenyl)cyclobutyl]-1,3,4-thiadiazol-2-yl}-2-fluorobenzamide;

5-{[(cyclopropylmethyl)amino]sulfonyl}-2-fluoro-N-(5-{1-[3-(trifluoromethyl)phenyl]cyclobutyl}-1,3,4-thiadiazol-2-yl)benzamide;

5-(aminosulfonyl)-2-fluoro-N-{5-[1-(3-methylphenyl)cyclobutyl]-1,3,4-thiadiazol-2-yl}benzamide;

2-fluoro-N-{5-[1-(3-methylphenyl)cyclobutyl]-1,3,4-thiadiazol-2-yl}-5-{[(2,2,2-trifluoroethyl)amino]sulfonyl}benzamide;

5-[(ethylamino)sulfonyl]-2-fluoro-N-{5-[1-(3-methylphenyl)cyclobutyl]-1,3,4-thiadiazol-2-yl}benzamide;

5-{[(cyclopropylmethyl)amino]sulfonyl}-2-fluoro-N-{5-[1-(3-methylphenyl)cyclobutyl]-1,3,4-thiadiazol-2-yl}benzamide;

N-(5-cyclobutyl-1,3,4-thiadiazol-2-yl)-2-fluoro-5-{[(2,2,2-trifluoroethyl)amino]sulfonyl}benzamide;

N-{5-[1-(4-chlorophenyl)cyclobutyl]-1,3,4-thiadiazol-2-yl}-2-fluoro-5-{[(2,2,2-trifluoroethyl)amino]sulfonyl}benzamide;

N-{5-[1-(4-chlorophenyl)cyclobutyl]-1,3,4-thiadiazol-2-yl}-5-[(ethylamino)sulfonyl]-2-fluorobenzamide;

2-fluoro-N-[5-(1-methyl-1-phenylethyl)-1,3,4-thiadiazol-2-yl]-5-{[(2,2,2-trifluoroethyl)amino]sulfonyl}benzamide;

2-fluoro-5-{[(2-fluoroethyl)amino]sulfonyl}-N-[5-(1-methyl-1-phenylethyl)-1,3,4-thiadiazol-2-yl]benzamide; and 5-[(cyclobutylamino)sulfonyl]-2-fluoro-N-[5-(4-fluorophenyl)-1,3,4-thiadiazol-2-yl]benzamide;

or a pharmaceutically acceptable salt thereof.

16. A pharmaceutical composition comprising a compound according to claim 1 and a pharmaceutically acceptable carrier or diluent.

* * * * *